US012497348B2

(12) United States Patent
Han et al.

(10) Patent No.: US 12,497,348 B2
(45) Date of Patent: Dec. 16, 2025

(54) LIGHT EMITTING ELEMENT AND AMINE COMPOUND FOR THE SAME

(71) Applicant: Samsung Display Co., Ltd., Yongin-si (KR)

(72) Inventors: Sanghyun Han, Hwaseong-si (KR); Dongjun Kim, Suwon-si (KR); Minji Kim, Hwaseong-si (KR); Hankyu Pak, Suwon-si (KR); Eunjae Jeong, Hwaseong-si (KR); Sohee Jo, Cheonan-si (KR); Ilsoo Oh, Seoul (KR); Illhun Cho, Seoul (KR)

(73) Assignee: Samsung Display Co., Ltd., Yongin-si (KR)

( * ) Notice: Subject to any disclaimer, the term of this patent is extended or adjusted under 35 U.S.C. 154(b) by 865 days.

(21) Appl. No.: 17/588,041

(22) Filed: Jan. 28, 2022

(65) Prior Publication Data

US 2022/0255003 A1 Aug. 11, 2022

(30) Foreign Application Priority Data

Feb. 3, 2021 (KR) ........................ 10-2021-0015237

(51) Int. Cl.

| | |
|---|---|
| ***C07C 211/61*** | (2006.01) |
| ***H10K 85/60*** | (2023.01) |
| *H10K 50/15* | (2023.01) |
| *H10K 59/12* | (2023.01) |

(52) U.S. Cl.

CPC .......... *C07C 211/61* (2013.01); *H10K 85/622* (2023.02); *H10K 85/624* (2023.02); *H10K 85/626* (2023.02); *H10K 85/633* (2023.02); *H10K 85/636* (2023.02); *H10K 85/6572* (2023.02); *H10K 85/6574* (2023.02); *H10K 85/6576* (2023.02); *H10K 50/156* (2023.02); *H10K 59/12* (2023.02)

(58) Field of Classification Search

None

See application file for complete search history.

(56) References Cited

U.S. PATENT DOCUMENTS

| | | | | |
|---|---|---|---|---|
| 4,720,432 | A | 1/1988 | VanSlyke et al. | |
| 5,061,569 | A | 10/1991 | VanSlyke et al. | |
| 6,242,115 | B1 | 6/2001 | Thomson et al. | |
| 8,021,764 | B2 | 9/2011 | Hwang et al. | |
| 9,139,522 | B2 | 9/2015 | Yabunouchi et al. | |
| 10,941,108 | B2 | 3/2021 | Jeong et al. | |
| 2012/0319091 | A1 | 12/2012 | Kato | |
| 2019/0165273 | A1 | 5/2019 | Takada et al. | |
| 2021/0005814 | A1* | 1/2021 | Watabe | H10K 85/633 |
| 2022/0173346 | A1* | 6/2022 | Ko | H10K 50/156 |
| 2022/0306567 | A1* | 9/2022 | Ma | H10K 85/654 |
| 2025/0031567 | A1* | 1/2025 | Kim | C07D 409/04 |
| 2025/0057038 | A1* | 2/2025 | Kang | H10K 85/636 |

FOREIGN PATENT DOCUMENTS

| | | | | |
|---|---|---|---|---|
| CN | 110183332 A | 8/2019 | | |
| CN | 110317141 A | 10/2019 | | |
| CN | 110845394 A | 2/2020 | | |
| CN | 111018721 A | 4/2020 | | |
| CN | 111 393 308 A | 7/2020 | | |
| CN | 113651785 A | * 11/2021 | | C07B 59/002 |
| EP | 4174055 A1 | 5/2023 | | |
| JP | H 06-314594 A | 11/1994 | | |
| JP | H 08-291115 A | 11/1996 | | |
| JP | H 11-144873 A | 5/1999 | | |
| JP | 2000-302756 A | 10/2000 | | |
| JP | 2000-309566 A | 11/2000 | | |
| JP | 2006-151979 A | 6/2006 | | |
| KR | 10-2012-0052765 A | 5/2012 | | |
| KR | 10-1516062 B1 | 4/2015 | | |
| KR | 10-2017-0023370 A | 3/2017 | | |
| KR | 10-1790321 B1 | 10/2017 | | |
| KR | 10-2019 0063368 A | 6/2019 | | |
| KR | 10-2019-0109691 A | 9/2019 | | |

OTHER PUBLICATIONS

Machine translation of CN-113651785-A, translation generated Feb. 2025, 34 pages. (Year: 2025).*
Machine translation of CN-110845394, translation generated Feb. 2025, 21 pages. (Year: 2025).*
Extended European Search Report dated Jul. 14, 2022, in corresponding EP Application No. 22154923.1-1110 (6 pages).
Chinese Office Action dated May 9, 2025, issued in corresponding Chinese Patent Application No. 202210100886.1, 7 pages.

* cited by examiner

*Primary Examiner* — Robert S Loewe
(74) *Attorney, Agent, or Firm* — Womble Bond Dickinson (US) LLP

(57) ABSTRACT

A light-emitting element includes a first electrode, a second electrode, and at least one functional layer disposed between the first electrode and the second electrode and including an amine compound represented by Formula 1. The light-emitting element may exhibit high emission efficiency and improved service life characteristics:

Formula 1

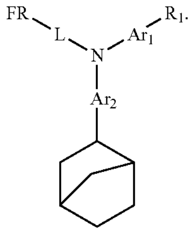

20 Claims, 7 Drawing Sheets

LIGHT EMITTING ELEMENT AND AMINE COMPOUND FOR THE SAME

CROSS-REFERENCE TO RELATED APPLICATION

This application claims priority to and the benefit of Korean Patent Application No. 10-2021-0015237, filed on Feb. 3, 2021, the entire content of which is incorporated herein by reference.

BACKGROUND

One or more aspects of embodiments of the present disclosure relate to a light-emitting element and an amine compound utilized therein, and for example to an amine compound utilized in a hole transport region and a light-emitting element including the same.

Organic electroluminescence display devices are actively being developed as image display devices. An organic electroluminescence display device is a display device including so-called a self-luminescent light-emitting element, in which holes and electrons respectively injected from a first electrode and a second electrode recombine in an emission layer, and a light-emitting material in the emission layer emits light to attain display.

For application of a light-emitting element to a display device, a reduced driving voltage, increased emission efficiency, and/or increased service life are desired, and development of materials for a light-emitting element capable of stably attaining such requirements are desired.

To achieve a high-efficiency light-emitting element, materials for a hole transport region for inhibiting diffusion of exciton energy in an emission layer are being developed.

SUMMARY

One or more aspects of embodiments of the present disclosure are directed toward a light-emitting element exhibiting excellent or suitable emission efficiency and long service life characteristics.

One or more aspects of embodiments of the present disclosure are directed toward an amine compound which is a material for a light-emitting element having high efficiency and long service life characteristics.

One or more embodiments of the present disclosure provide an amine compound represented by Formula 1:

Formula 1

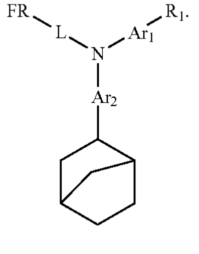

In Formula 1, $R_1$ may be an adamantyl group, a cyclohexyl group, or a bicycloheptyl group, and $Ar_1$ and $Ar_2$ may each independently be a substituted or unsubstituted arylene group having 6 to 30 ring-forming carbon atoms. L may be a direct linkage, a substituted or unsubstituted arylene group having 6 to 30 ring-forming carbon atoms, or a substituted or unsubstituted heteroarylene group having 2 to 30 ring-forming carbon atoms, and FR may be represented by Formula 2:

Formula 2

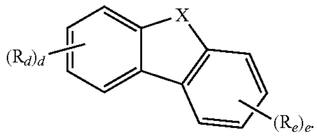

In Formula 2, X may be $CR_aR_b$, N, $NR_c$, O, or S, and $R_a$ to $R_c$ may each independently be a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring. d and e may each independently be an integer of 0 to 4, and $R_d$ and $R_e$ may each independently be a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring.

Formula 1 may be represented by Formula 1-1 or Formula 1-2:

Formula 1-1

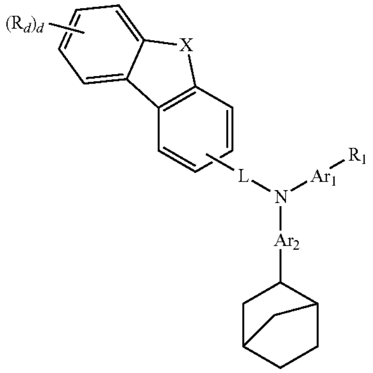

Formula 1-2

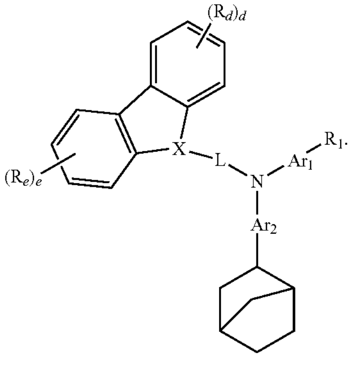

In Formula 1-1 and Formula 1-2, $R_1$, L, $Ar_1$, and $Ar_2$ may each independently be the same as defined in Formula 1, and X, $R_d$, $R_e$, d, and e may each independently be the same as defined in Formula 2.

Formula 1-2 may be represented by Formula 1-2A.

Formula 1-2A

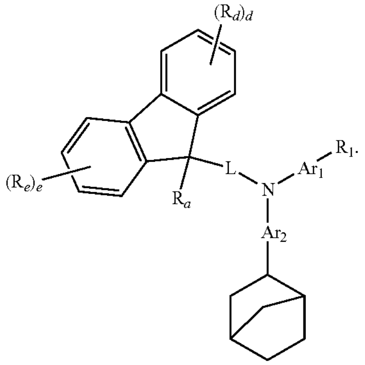

In Formula 1-2A, $R_1$, L, $Ar_1$, and $Ar_2$ may each independently be the same as defined in Formula 1, and $R_a$, $R_d$, $R_e$, d, and e may each independently be the same as defined in Formula 2.

In Formula 1, $Ar_1$ and $Ar_2$ may be a substituted or unsubstituted phenylene group.

Formula 1 may be represented by Formula 1A:

Formula 1A

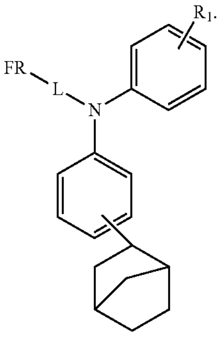

In Formula 1A, $R_1$, L, and FR may each independently be the same as defined in Formula 1.

Formula 1A may be represented by Formula 1A-1:

Formula 1A-1

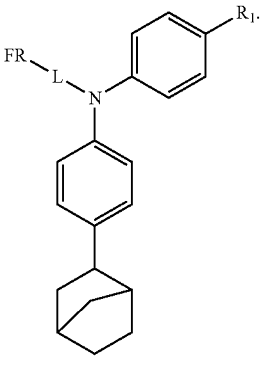

In Formula 1A-1, $R_1$, L, and FR may each independently be the same as defined in Formula 1.

One or more embodiments of the present disclosure provide a light-emitting element including a first electrode, a second electrode disposed on the first electrode, and at least one functional layer disposed between the first electrode and the second electrode and including the amine compound according to an embodiment described above.

The at least one functional layer may include an emission layer, a hole transport region disposed between the first electrode and the emission layer, and an electron transport region disposed between the emission layer and the second electrode, and the hole transport region may include the amine compound.

The hole transport region may include a hole injection layer disposed on the first electrode, and a hole transport layer disposed on the hole injection layer, and the hole transport layer may include the amine compound.

The at least one functional layer may include an emission layer, a first hole transport layer disposed between the first electrode and the emission layer, a second hole transport layer disposed between the first hole transport layer and the emission layer; and an electron transport region disposed between the emission layer and the second electrode, and the first hole transport layer may include the amine compound.

The second hole transport layer may include an amine derivative compound represented by Formula 3:

Formula 3

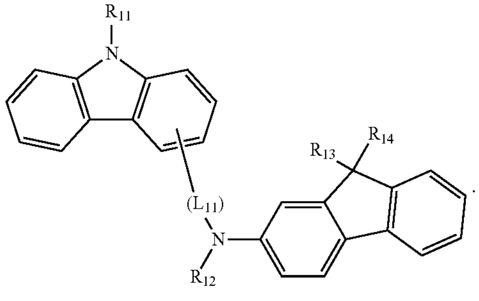

In Formula 3, $L_{11}$ may be a direct linkage, a substituted or unsubstituted arylene group having 6 to 30 ring-forming carbon atoms, or a substituted or unsubstituted heteroarylene group having 2 to 30 ring-forming carbon atoms, and $R_{11}$ to $R_{14}$ may each independently be a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring.

Formula 3 may be represented by Formula 3-1 or Formula 3-2:

Formula 3-1

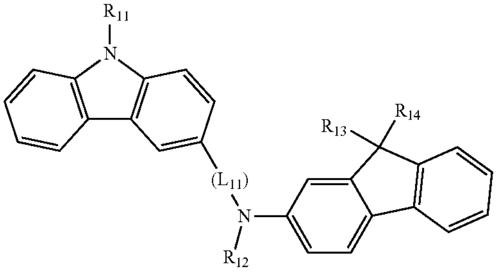

Formula 3-2

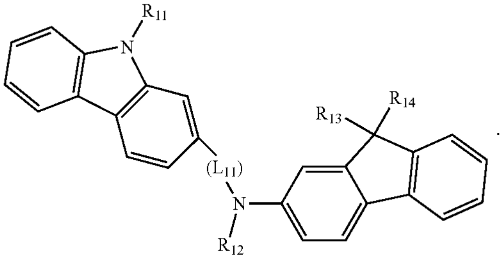

In Formula 3-1 and Formula 3-2, $L_{11}$, and $R_{11}$ to $R_{14}$ may each independently be the same as defined in Formula 3.

BRIEF DESCRIPTION OF THE FIGURES

The accompanying drawings are included to provide a further understanding of the present disclosure, and are incorporated in and constitute a part of this specification. The drawings illustrate embodiments of the present disclosure and, together with the description, serve to explain principles of the present disclosure. In the drawings.

DETAILED DESCRIPTION

Figure 1:
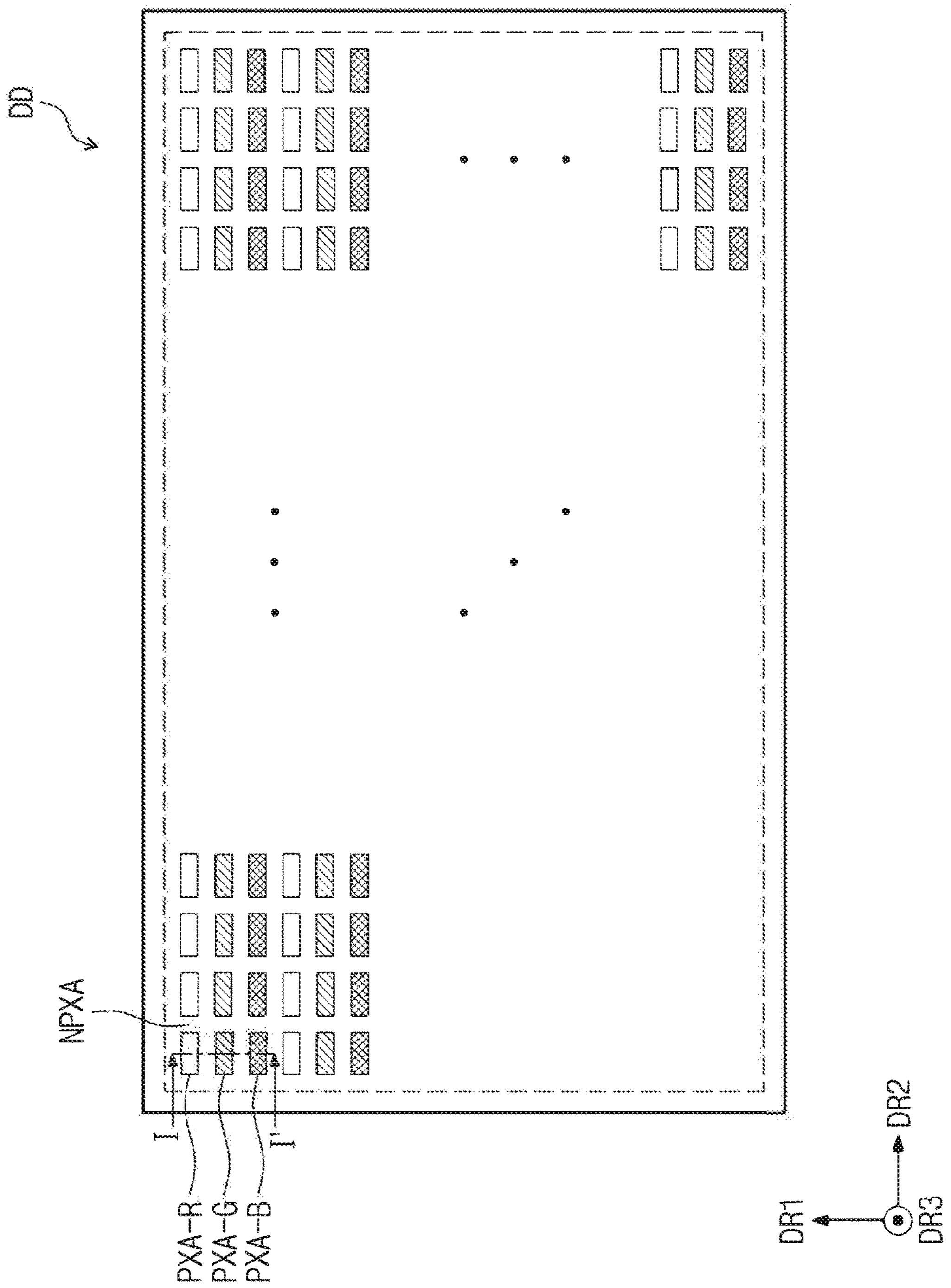
FIG. 1 is a plan view illustrating a display device according to an embodiment.

Embodiments of the present disclosure are compatible with various suitable modifications and alternative forms, and selected embodiments thereof are illustrated by way of example in the drawings and will be described herein in more detail.

However, it should be understood that the present present disclosure is not intended to be limited by the specific form disclosed, and all modifications, equivalents, and alternatives are included within the spirit and scope of the present present disclosure.

In describing the drawings, like reference numerals are used for like components, and duplicative descriptions thereof may not be provided. In the accompanying drawings, the dimensions of structures may be shown at enlarged scale for clarity of illustration. It will be understood that, although the terms first, second, etc. may be used herein to describe various components, these components should not be limited by these terms. These terms are only used to distinguish one component from another component. For example, a first component may be alternatively termed a second component without departing from the scope of the present disclosure, and similarly, a second component may be alternatively termed a first component. Singular forms such as "a", "an" and "the" are intended to include the plural forms as well, unless the context clearly indicates otherwise.

It will be further understood that the terms "include," "comprise," and/or "have," etc., when used in this application, specify the presence of stated features, integers, steps, operations, components, or parts, but do not preclude the presence or addition of one or more other features, integers, steps, operations, components, parts, or combination thereof.

As used herein, the terms "use," "using," and "used" may be considered synonymous with the terms "utilize," "utilizing," and "utilized," respectively. As used herein, expressions such as "at least one of," "one of," and "selected from," when preceding a list of elements, modify the entire list of elements and do not modify the individual elements of the list.

As used herein, the term "and/or" includes any and all combinations of one or more of the associated listed items. Further, the use of "may" when describing embodiments of the present disclosure refers to "one or more embodiments of the present disclosure".

In this application, when a part such as a layer, a film, a region, a plate is referred to as being "on" or "above" the other part, it may be "directly on" the other part, or an intervening part may also be present. When a part such as a layer, a film, a region, a plate is referred to as being "under" or "below" the other part, it may be "directly under" the other part, or an intervening part may also be present. In contrast, when an element is referred to as being "directly on," "directly under," another part, there are no intervening elements present. Further, when a part is referred to as being disposed "on" the other part, it may be disposed on the upper part or the lower part as well (e.g., when viewed from a different perspective).

In the present specification, the term "substituted or unsubstituted" indicates a state of being unsubstituted, or substituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. In some embodiments, each of the example substituents may be further substituted or unsubstituted. For example, a biphenyl group may be interpreted as a named aryl group, or as a phenyl group substituted with a phenyl group.

In the present specification, the term "bonded to an adjacent group to form a ring" may refer to being bonded to an adjacent group to form a substituted or unsubstituted hydrocarbon ring, or a substituted or unsubstituted heterocycle. The term "hydrocarbon ring" includes an aliphatic hydrocarbon ring and an aromatic hydrocarbon ring. The term "heterocycle" includes an aliphatic heterocycle and an aromatic heterocycle. The hydrocarbon ring and heterocycle may each independently be a monocycle or a polycycle. In some embodiments, the ring formed by groups being bonded to each other may be further connected to another ring to form a spiro structure.

In the present specification, the term "adjacent group" may refer to a substituent on the same atom or point, a substituent on an atom that is directly connected to the base atom or point, or a substituent sterically positioned (e.g., within intramolecular bonding distance) to the corresponding substituent. For example, in 1,2-dimethylbenzene, two methyl groups may be interpreted as mutually "adjacent groups", and in 1,1-diethylcyclopentane, two ethyl groups may be interpreted as mutually "adjacent groups". Further, in 4,5-dimethylphenanthrene, two methyl groups may be interpreted as mutually "adjacent groups".

In the present specification, examples of the halogen atom may include a fluorine atom, a chlorine atom, a bromine atom, or an iodine atom.

In the present specification, an alkyl group may be a linear, branched, or cyclic group. The number of carbon atoms of the alkyl group may be 1 to 50, 1 to 30, 1 to 20, 1 to 10, or 1 to 6. Examples of the alkyl group may include, but are not limited to, a methyl group, an ethyl group, an n-propyl group, an isopropyl group, an n-butyl group, a s-butyl group, a t-butyl group, an i-butyl group, a 2-ethylbutyl group, a 3,3-dimethylbutyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-t-butylcyclohexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantyl group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldocecyl group, a 2-octyldodecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-heneicosyl group, an n-docosyl group, an-tricosyl group, an n-tetracosyl group, an n-pentacosyl group, an n-hexacosyl group, an n-heptacosyl group, an n-octacosyl group, an n-nonacosyl group, an n-triacontyl group, and/or the like.

In the present specification, the term "hydrocarbon ring group" refers to an optional functional group or substituent derived from an aliphatic hydrocarbon ring or an aromatic hydrocarbon ring. The hydrocarbon ring group may be a saturated hydrocarbon ring group having 5 to 20 ring-forming carbon atoms.

In the present specification, the term "aryl group" refers to any functional group or substituent derived from an aromatic hydrocarbon ring. The aryl group may be a monocyclic aryl group or a polycyclic aryl group. The number of ring-forming carbon atoms of the aryl group may be 6 to 30, 6 to 20, or 6 to 15. Examples of the aryl group may include, but are not limited to, a phenyl group, a naphthyl group, a fluorenyl group, an anthracenyl group, a phenanthryl group, a biphenyl group, a terphenyl group, a quaterphenyl group, a quinquephenyl group, a sexiphenyl group, a triphenylenyl group, a pyrenyl group, a benzofluoranthenyl group, a chrysenyl group, and/or the like.

In some embodiments, the fluorenyl group may be substituted (e.g., at the 9H position), and two substituents may be bonded to each other to form a spiro structure. Examples of the case where the fluorenyl group is substituted are as follows. However, embodiments of the present disclosure are not limited thereto:

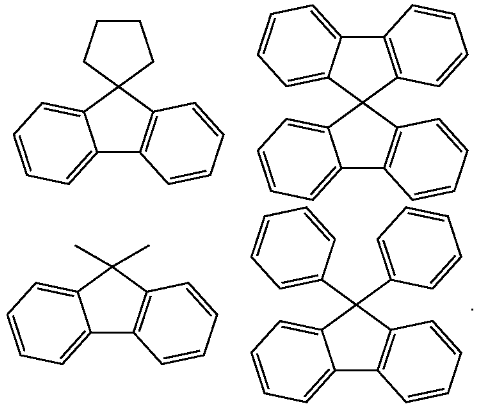

In the present specification, the term "heterocyclic group" refers to any functional group or substituent derived from a ring including at least one of boron (B), oxygen (O), nitrogen (N), phosphorus (P), silicon (Si) or sulfur (S) as a heteroatom. The term "heterocyclic group" includes an aliphatic heterocyclic group and an aromatic heterocyclic group. The aromatic heterocyclic group may be a heteroaryl group. The aliphatic heterocycle and the aromatic heterocycle may be a monocycle or a polycycle.

In the present specification, the heterocyclic group may include at least one of B, O, N, P, Si of S as a heteroatom. When the heterocyclic group includes two or more heteroatoms, the two or more heteroatoms may be the same as or different from each other. The heterocyclic group may be a monocyclic heterocyclic group or a polycyclic heterocyclic group, and has a concept including a heteroaryl group. The number of ring-forming carbon atoms of the heterocyclic group may be 2 to 30, 2 to 20, or 2 to 10.

In the present specification, the aliphatic heterocyclic group may include at least one of B, O, N, P, Si or S as a heteroatom. The number of ring-forming carbon atoms of the aliphatic heteroaryl group may be 2 to 30, 2 to 20, or 2 to 10. Examples of the aliphatic heterocyclic group may include, but are not limited to, an oxirane group, a thiirane group, a pyrrolidine group, a piperidine group, a tetrahydrofuran group, a tetrahydrothiophene group, a thiane group, a tetrahydropyran group, a 1,4-dioxane group, and/or the like.

In the present specification, the heteroaryl group may include at least one of B, O, N, P, Si or S as a heteroatom. When the heteroaryl group includes two or more heteroatoms, the two or more heteroatoms may be the same as or different from each other. The heteroaryl group may be a monocyclic heterocyclic group or a polycyclic heterocyclic group. The number of ring-forming carbon atoms of the heteroaryl group may be 2 to 30, 2 to 20, or 2 to 10. Examples of the heteroaryl group may include, but are not limited to a thiophene group, a furan group, a pyrrole group, imidazole group, a triazole group, a pyridine group, a bipyridine group, a pyrimidine group, a triazine group, a triazole group, an acridyl group, a pyridazine group, a pyrazinyl group, a quinoline group, a quinazoline group, a quinoxaline group, a phenoxazine group, a phthalazine group, a pyrido pyrimidine group, a pyrido pyrazine group, a pyrazino pyrazine group, an isoquinoline group, an indole group, a carbazole group, an N-arylcarbazole group, an N-heteroarylcarbazole group, an N-alkylcarbazole group, a benzoxazole group, a benzimidazole group, a benzothiazole group, a benzocarbazole group, a benzothiophene group, a dibenzothiophene group, a thienothiophene group, a benzofuran group, a phenanthroline group, a thiazole group, a isoxazole group, an oxazole group, an oxadiazole group, a thiadiazole group, a phenothiazine group, a dibenzosilole group, a dibenzofuran group, and/or the like.

In the present specification, the same description regarding the aryl group stated above may be applied to the arylene group, except that the arylene group is a divalent group. The same description about the heteroaryl group may be applied to the heteroarylene group, except that the heteroarylene group is a divalent group.

In the present specification, the term "silyl group" includes an alkyl silyl group and an aryl silyl group. Examples of the silyl group may include, but are not limited to, a trimethylsilyl group, a triethylsilyl group, a t-butyldimethylsilyl group, a propyldimethylsilyl group, a triphenylsilyl group, a diphenylsilyl group, a phenylsilyl group, and/or the like.

In the present specification, the number of carbon atoms of the amino group may be 1 to 30, but is not particularly limited thereto. The amino group may include an alkyl amino group, an aryl amino group, or a heteroaryl amino group. Examples of the amino group may include, but are not limited to, a methylamino group, a dimethylamino group, a phenylamino group, a diphenylamino group, a naphthylamino group, a 9-methyl-anthracenylamino group, and/or the like.

In the present specification, the number of carbon atoms of the carbonyl group is not particularly limited, but may be 1 to 40, 1 to 30, or 1 to 20. For example, the carbonyl group may have the following structure, but embodiments of the present disclosure are not limited thereto.

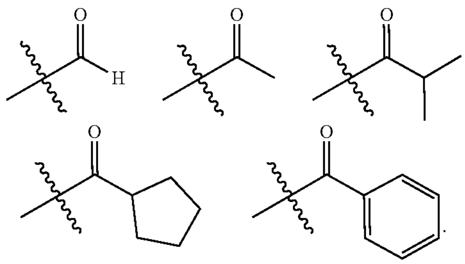

In the present specification, the number of carbon atoms of the sulfinyl group or sulfonyl group may be 1 to 30, but is not particularly limited thereto. The term "sulfinyl group" may include an alkyl sulfinyl group and an aryl sulfinyl group. The term "sulfonyl group" may include an alkyl sulfonyl group and an aryl sulfonyl group.

In the present specification, the term "thio group" may include an alkyl thio group and an aryl thio group. The term "thio group" may refer to a group in which a sulfur atom is bonded to an alkyl group or an aryl group defined as above. Examples of the thio group may include, but are not limited to, a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group.

In the present specification, the term "oxy group" may refer to a group in which an oxygen atom is bonded to an alkyl group or an aryl group defined as above. The oxy group may include an alkoxy group and aryl oxy group. The alkoxy group may be a linear, branched, or cyclic group. The number of carbon atoms of the alkoxy group may be, for example, 1 to 20 or 1 to 10, but is not particularly limited. Examples of the oxy group may include, but are not limited to methoxy, ethoxy, n-propoxy, isopropoxy, butoxy, pentyloxy, hexyloxy, octyloxy, nonyloxy, decyloxy, benzyloxy, and/or the like.

In the present specification, the term "boron group" may refer to a group in which a boron atom is bonded to an alkyl group or an aryl group defined above. The term "boron group" includes an alkyl boron group and an aryl boron group. Examples of the boron group may include, but are not limited to, a trimethyl boron group, a triethyl boron group, a t-butyldimethyl boron group, a triphenyl boron group, a diphenyl boron group, and a phenyl boron group, and/or the like.

In the present specification, the term "alkenyl group" may be linear or branched. The number of carbon atoms is not particularly limited, but may be 2 to 30, 2 to 20, or 2 to 10. Examples of the alkenyl group may include, but are not limited to, a vinyl group, a 1-butenyl group, a 1-pentenyl group, a 1,3-butadienyl aryl group, a styrenyl group, a styrylvinyl group, and/or the like.

In the present specification, the number of carbon atoms of the amine group may be 1 to 30, but is not particularly limited thereto The term "amine group" may include an alkyl amine group and an aryl amine group. Examples of the amine group may include, but are not limited to a methylamine group, a dimethylamine group, a phenylamine group, a diphenylamine group, a naphthylamine group, a 9-methylanthracenylamine group, and/or the like.

In the present specification, the alkyl group in an alkylthio group, an alkyl sulfonyl group, an alkylaryl group, an alkyl amino group, an alkyl boron group, an alkyl silyl group, and/or an alkyl amine group may be the same as the examples of the alkyl group described above.

In the present specification, the aryl group in an aryloxy group, an arylthio group, an aryl sulfonyl group, an arylamino group, an aryl boron group, an aryl silyl group, and an aryl amine group is substantially the same as the examples of the aryl group described above.

In the present specification, the term "direct linkage" may refer to a single bond.

In some embodiments, in the present specification

" 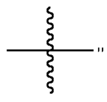 " and "——*"

refer to a position to be connected.

Hereinafter, embodiments of the present disclosure will be explained with reference to the drawings.

Figure 2:
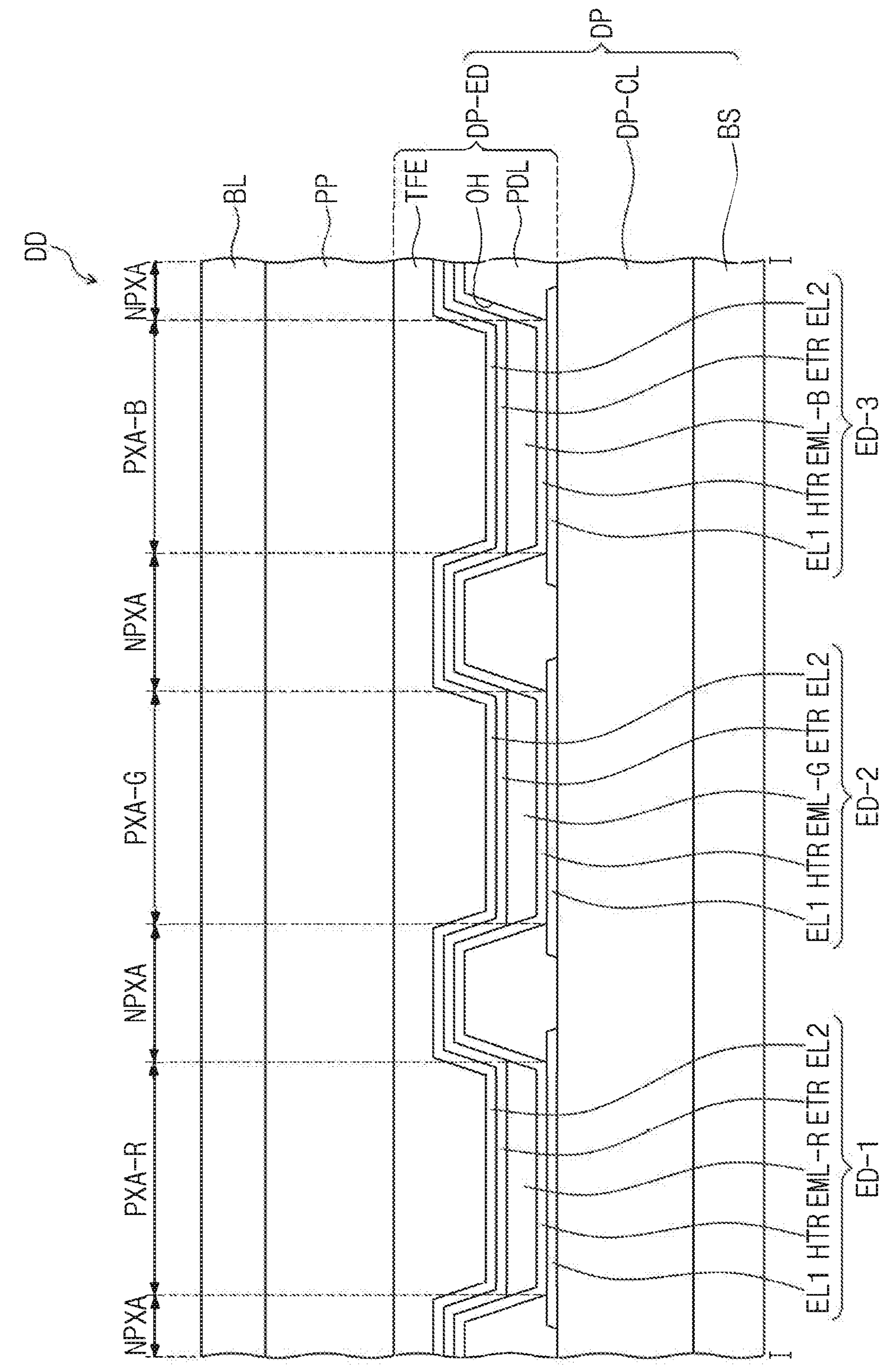
FIG. 2 is a cross-sectional view of a display device according to an embodiment.

FIG. 1 is a plan view illustrating an embodiment of a display device DD. FIG. 2 is a cross-sectional view of a display device DD according to an embodiment. FIG. 2 is a cross-sectional view illustrating a portion taken along line I-I' in FIG. 1.

The display device DD may include a display panel DP and an optical layer PP disposed on the display panel DP. The display panel DP includes light-emitting elements ED-1, ED-2, and ED-3. The display device DD may include a plurality of light-emitting elements ED-1, ED-2, and ED-3. The optical layer PP may be disposed on the display panel DP and control the reflected light by external light on the display panel DP. The optical layer PP may include, for example, a polarization layer or a color filter layer. In some embodiments, the optical layer PP may not be provided in the display device DD according to an embodiment.

A base substrate BL may be disposed on the optical layer PP. The base substrate BL may be a member that provides a base surface on which the optical layer PP is disposed. The base substrate BL may be a glass substrate, a metal substrate, a plastic substrate, and/or the like. However, embodiments of the present disclosure are not limited thereto, and the base substrate BL may be an inorganic layer, an organic layer, or a composite material layer. In some embodiments, the base substrate BL may not be provided in an embodiment.

The display device DD according to an embodiment may further include a filling layer. The filling layer may be disposed between the display element layer DP-ED and the base substrate BL. The filling layer may be an organic material layer. The filling layer may include at least one of acrylic resins, silicon resins, or epoxy resins.

The display panel DP may include a base layer BS, and a circuit layer DP-CL and a display element layer DP-ED, which are provided on the base layer BS. The display element layer DP-ED may include pixel-defining films PDL, light-emitting elements ED-1, ED-2, and ED-3 disposed between the pixel-defining films PDL, and an encapsulating layer TFE disposed on the light-emitting elements ED-1, ED-2, and ED-3.

The base layer BS may be a member that provides a base surface on which the display element layer DP-ED is disposed. The base layer BS may be a glass substrate, a metal substrate, a plastic substrate, and/or the like. However, embodiments of the present disclosure are not limited thereto, and the base layer BS may be an inorganic layer, an organic layer, or a composite material layer.

In an embodiment, the circuit layer DP-CL is disposed on the base layer BS, and the circuit layer DP-CL may include a plurality of transistors. The transistors may each include a control electrode, an input electrode, and an output electrode. For example, the circuit layer DP-CL may include a switching transistor and a driving transistor for driving the light-emitting elements ED-1, ED-2, and ED-3 of the display element layer DP-ED.

Each of the light-emitting elements ED-1, ED-2, and ED-3 may have a structure of a light-emitting element ED of an embodiment according to FIGS. 3 to 7 to be described later. Each of the light-emitting elements ED-1, ED-2, and ED-3 may include a first electrode EL1, a hole transport region HTR, emission layers EML-R, EML-G, and EML-B, an electron transport region ETR, and a second electrode EL2.

In FIG. 2, the emission layers EML-R, EML-G, and EML-B of the light-emitting elements ED-1, ED-2, and ED-3 are disposed in openings OH defined in the pixel-defining films PDL, and the hole transport region HTR, the electron transport region ETR, and the second electrode EL2 may be provided as common layers in all of the light-emitting elements ED-1, ED-2, and ED-3. However, embodiments of the present disclosure are not limited thereto. In some embodiments, the hole transport region HTR and the electron transport region ETR may be patterned and provided in (e.g., only in) the openings OH defined in the pixel-defining films PDL. For example, in an embodiment, the hole transport region HTR, the emission layers EML-R, EML-G, and EML-B, and the electron transport region ETR, etc., of the light-emitting elements ED-1, ED-2, and ED-3 may be patterned and provided through an inkjet printing method.

The encapsulating layer TFE may cover the light-emitting elements ED-1, ED-2, and ED-3. The encapsulating layer TFE may seal the display element layer DP-ED. The encapsulating layer TFE may be a thin-film encapsulating layer. The encapsulating layer TFE may be a single layer or a plurality of layers being stacked. The encapsulating layer TFE includes at least one insulating layer. The encapsulating layer TFE according to an embodiment may include at least one inorganic film (hereinafter, an encapsulating inorganic film). In some embodiments, the encapsulating layer TFE according to an embodiment may include at least one organic film (hereinafter, an encapsulating organic film) and at least one encapsulating inorganic film.

The encapsulating inorganic film protects the display element layer DP-ED from moisture/oxygen, and the encapsulating organic film protects the display element layer DP-ED from foreign materials (such as dust particles). The encapsulating inorganic film may include silicon nitride, silicon oxy nitride, silicon oxide, titanium oxide, aluminum oxide, and/or the like, but embodiments of the present disclosure are not particularly limited thereto. The encapsulating organic film may include an acrylic compound, an epoxy-based compound, and/or the like. The encapsulating organic film may include a photopolymerizable organic material, but embodiments of the present disclosure are not particularly limited thereto.

The encapsulating layer TFE may be disposed on the second electrode EL2 and may be disposed while filling the opening OH.

Referring to FIG. 1 and FIG. 2, the display device DD may include a non-light-emitting region NPXA and light-emitting regions PXA-R, PXA-G, and PXA-B. The light-emitting regions PXA-R, PXA-G, and PXA-B may respectively correspond to regions in which lights generated from the light-emitting elements ED-1, ED-2, and ED-3 are emitted. The light-emitting regions PXA-R, PXA-G, and PXA-B may be spaced apart from each other on a plane (e.g., in a plan view).

The light-emitting regions PXA-R, PXA-G, and PXA-B may be separated by the pixel-defining films PDL. The non-light-emitting regions NPXA may be regions disposed between the neighboring light-emitting regions PXA-R, PXA-G, and PXA-B, and corresponding to the pixel-defining films PDL. In the present specification, the light-emitting regions PXA-R, PXA-G, and PXA-B may respectively correspond to pixels. The pixel-defining films PDL may separate the light-emitting elements ED-1, ED-2 and ED-3. The emission layers EML-R, EML-G and EML-B of the light-emitting elements ED-1, ED-2 and ED-3 may be disposed and separated in the openings OH defined in the pixel-defining films PDL.

The light-emitting regions PXA-R, PXA-G, and PXA-B may be classified into a plurality of groups according to the color of light generated from the light-emitting elements ED-1, ED-2, and ED-3. In the display device DD according to an embodiment, illustrated in FIGS. 1 and 2, three light-emitting regions PXA-R, PXA-G, and PXA-B may respectively be to emit red light, green light, and blue light, and are illustrated by way of example. For example, the display device DD according to an embodiment may include a red light-emitting region PXA-R, a green light-emitting region PXA-G, and a blue light-emitting region PXA-B, which are distinguished from each other.

In the display device DD according to an embodiment, a plurality of light-emitting elements ED-1, ED-2, and ED-3 may be to emit light having different wavelength ranges. For example, in an embodiment, the display device DD may include a first light-emitting element ED-1 to emit red light, a second light-emitting element ED-2 to emit green light, and a third light-emitting element ED-3 to emit blue light. For example, the red light-emitting region PXA-R, the green light-emitting region PXA-G, and the blue light-emitting region PXA-B of the display device DD may correspond to the first light-emitting element ED-1, the second light-emitting element ED-2, and the third light-emitting element ED-3, respectively.

However, embodiments of the present disclosure are not limited thereto, and the first to third light-emitting elements ED-1, ED-2, and ED-3 may be to emit light of substantially the same wavelength range, or at least one thereof may be to emit light of a different wavelength range. For example, all of the first to third light-emitting elements ED-1, ED-2, and ED-3 may be to emit blue light.

The light-emitting regions PXA-R, PXA-G, and PXA-B in the display device DD according to an embodiment may be arranged in a stripe shape. Referring to FIG. 1, a plurality of red light-emitting regions PXA-R may be arranged with each other along a second direction axis DR2, a plurality of green light-emitting regions PXA-G may be arranged with each other along the second direction axis DR2, and a plurality of blue light-emitting regions PXA-B may be arranged with each other along the second direction axis DR2. In some embodiments, the red light-emitting region PXA-R, the green light-emitting region PXA-G, and the blue light-emitting region PXA-B may be alternatingly arranged with each other along a first direction axis DR1.

FIG. 1 and FIG. 2 illustrate that all the light-emitting regions PXA-R, PXA-G, and PXA-B have similar areas, but embodiments of the present disclosure are not limited thereto. The areas (e.g., planar areas) of the light-emitting regions PXA-R, PXA-G, and PXA-B may be different from each other depending on the wavelength range of the emitted light. In some embodiments, the areas of the light-emitting regions PXA-R, PXA-G, and PXA-B may indicate (be) areas as viewed on a plane defined by the first direction axis DR1 and the second direction axis DR2 (e.g., in a plan view).

The arrangement of the light-emitting regions PXA-R, PXA-G, and PXA-B is not limited to the configuration illustrated in FIG. 1, and in some embodiments, the red light-emitting region PXA-R, the green light-emitting region PXA-G, and the blue light-emitting region PXA-B may be provided (arranged) in one or more suitable combinations or patterns, depending on the characteristics of display quality required for the display device DD. For example, the light-emitting regions PXA-R, PXA-G, and PXA-B may be arranged in a PENTILE® configuration or a diamond configuration.

In some embodiments, the areas of the light-emitting regions PXA-R, PXA-G, and PXA-B may be different from each other. For example, in an embodiment, the area of the green light-emitting region PXA-G may be smaller than the area of the blue light-emitting region PXA-B, but embodiments of the present disclosure are not limited thereto.

Hereinafter, FIGS. 3 to 7 are cross-sectional views schematically illustrating light-emitting elements according to an embodiment. The light-emitting element ED according to an embodiment may include a first electrode EL1, a second electrode EL2 facing the first electrode EL1, and at least one functional layer disposed between the first electrode EL1 and the second electrode EL2. The at least one functional layer may include a hole transport region HTR, an emission layer EML, and an electron transport region ETR, which are sequentially stacked. For example, the light-emitting element ED according to an embodiment may include a first electrode EL1, a hole transport region HTR, an emission layer EML, an electron transport region ETR, and a second electrode EL2, which are sequentially stacked.

Figure 3:
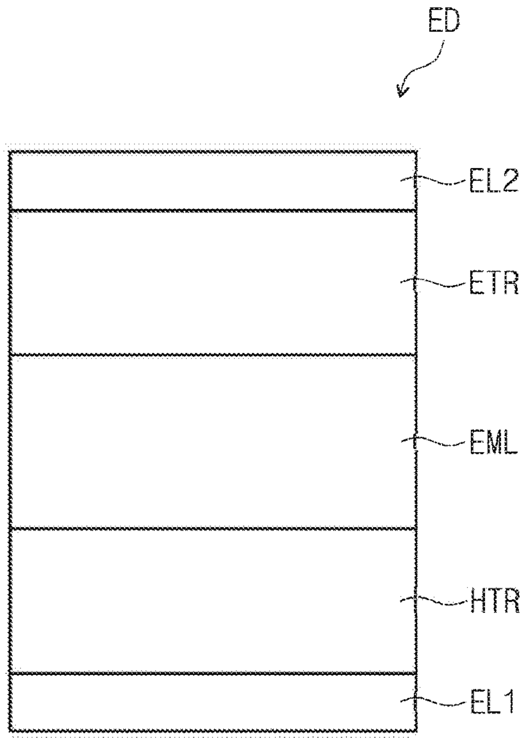
FIG. 3 is a cross-sectional view schematically illustrating a light-emitting element according to an embodiment.
Figure 4:
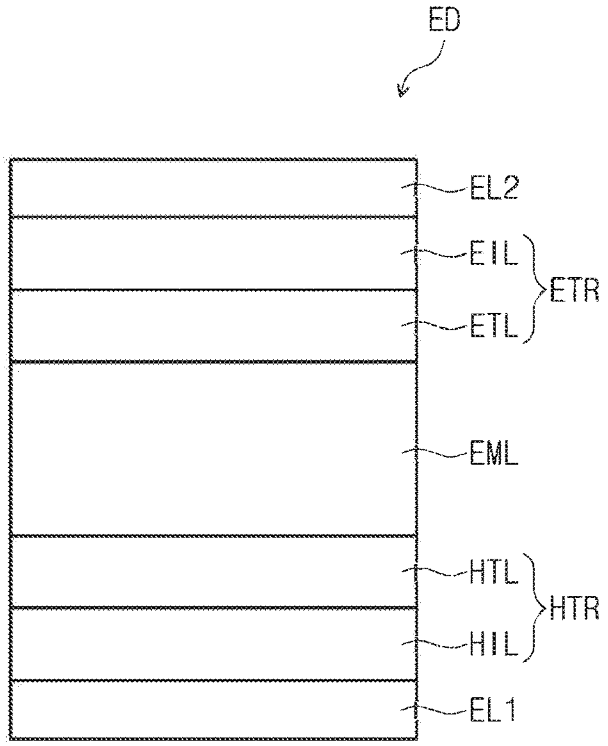
FIG. 4 is a cross-sectional view schematically illustrating a light-emitting element according to an embodiment.
Figure 5:
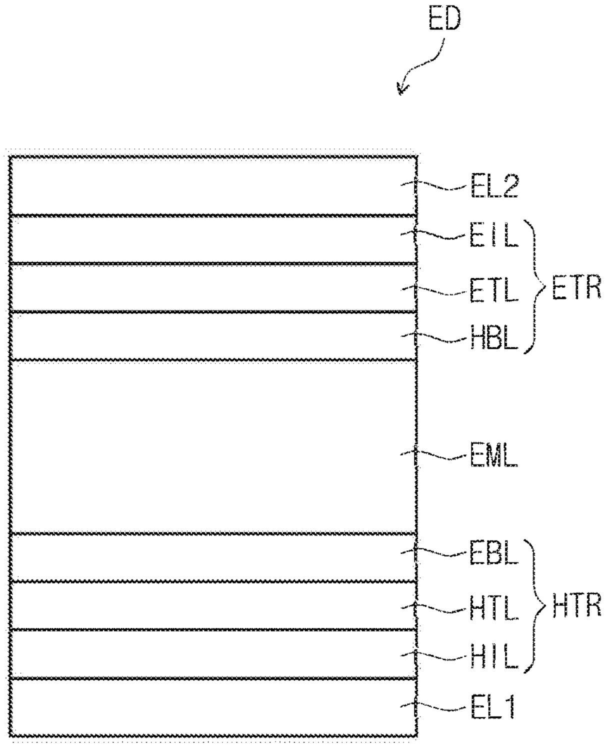
FIG. 5 is a cross-sectional view schematically illustrating a light-emitting element according to an embodiment.
Figure 6:
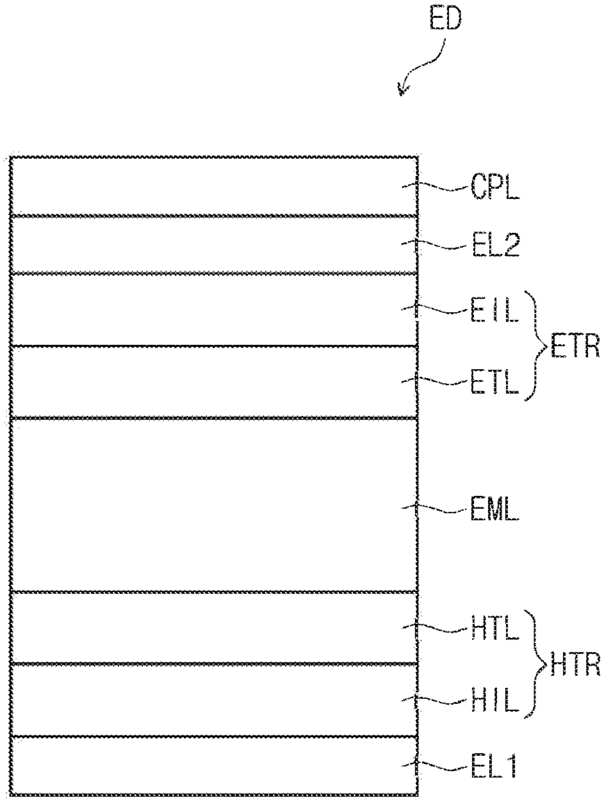
FIG. 6 is a cross-sectional view schematically illustrating a light-emitting element according to an embodiment.
Figure 7:
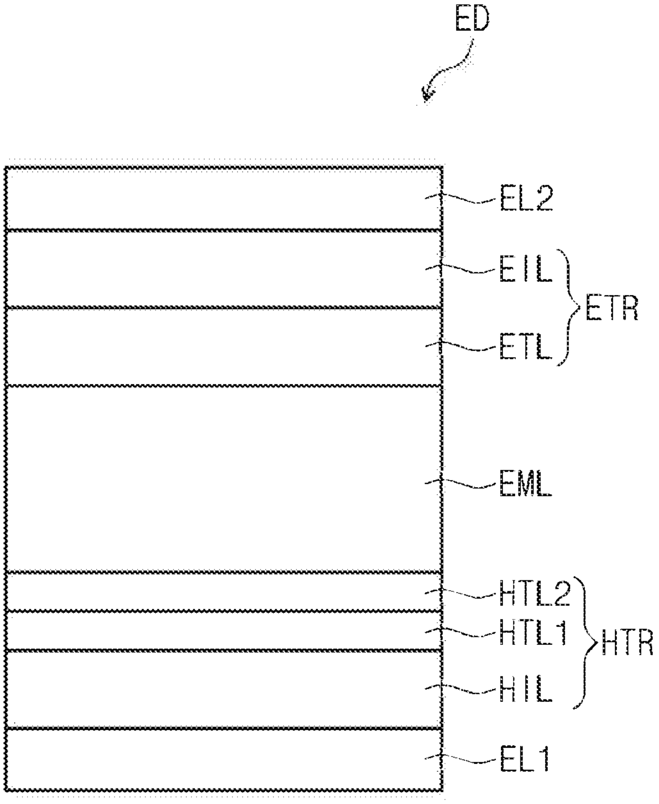
FIG. 7 is a cross-sectional view schematically illustrating a light-emitting element according to an embodiment.

Compared with FIG. 3, FIG. 4 illustrates a cross-sectional view of a light-emitting element ED according to an embodiment, in which a hole transport region HTR includes a hole injection layer HIL and a hole transport layer HTL, and an electron transport region ETR includes an electron injection layer EIL and an electron transport layer ETL. Compared with FIG. 3, FIG. 5 illustrates a cross-sectional view of a light-emitting element ED according to an embodiment, in which a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. Compared with FIG. 4, FIG. 6 illustrates a cross-sectional view of a light-emitting element ED according to an embodiment, in which a capping layer CPL disposed on (e.g., outside) the second electrode EL2 is provided. Compared with FIG. 4, FIG. 7 illustrates a cross-sectional view of a light-emitting element ED according to an embodiment, in which a hole transport region HTR includes a plurality of hole transport layers HTL1 and HTL2.

The light-emitting element ED according to an embodiment may include an amine compound (to be described later) in at least one functional layer (such as a hole transport region HTR, an emission layer EML, and/or an electron transport region ETR).

In the light-emitting element ED according to an embodiment, a first electrode EL1 has conductivity. The first electrode EL1 may be formed of a metal material, a metal alloy, and/or a conductive compound. The first electrode EL1 may be an anode or a cathode. However, embodiments of the present disclosure are not limited thereto. In some embodiments, the first electrode EL1 may be a pixel electrode. The first electrode EL1 may be a transmissive electrode, a transflective electrode, or a reflective electrode. When the first electrode EL1 is a transmissive electrode, the first electrode EL1 may include a transparent metal oxide (such as indium tin oxide (ITO), indium zinc oxide (IZO), zinc oxide (ZnO), indium tin zinc oxide (ITZO), and/or the like). When the first electrode EL1 is a transflective electrode or a reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/Al, molybdenum (Mo), titanium (Ti), tungsten (W), or a compound or mixture thereof (for example, a mixture of Ag and Mg). In some embodiments, the first electrode EL1 may have a multilayered structure including a reflective film or a transflective film formed of the above-described materials and a transparent conductive film formed of indium tin oxide (ITO), indium zinc oxide (IZO), zinc oxide (ZnO), indium tin zinc oxide (ITZO), and/or the like. For example, the first electrode EL1 may have a three-layer structure of ITO/Ag/ITO, but embodiments of the present disclosure are not limited thereto. In some embodiments, the first electrode EL1 may include the above-described metal material, a combination of two or more metal materials selected from the above-described metal materials, or one or more oxides of the above-described metal materials. The thickness of the first electrode EL1 may be about 700 Å to about 10000 Å. For example, the thickness of the first electrode EU may be about 1000 Å to about 3000 Å.

The hole transport region HTR is provided on the first electrode EL1. The hole transport region HTR may include at least one of a hole injection layer HIL, a hole transport layer HTL, a buffer layer or light-emitting auxiliary layer, or an electron blocking layer EBL. A thickness of the hole transport region HTR may be, for example, about 50 Å to about 15,000 Å.

The hole transport region HTR may have a single layer formed of a single material, a single layer structure formed of a plurality of different materials, or a multilayer structure having a plurality of layers formed of a plurality of different materials.

For example, the hole transport region HTR may have a structure of a single layer of a hole injection layer HIL or a hole transport layer HTL, or may have a structure of a single layer formed of a hole injection material and a hole transport material. Furthermore, the hole transport region HTR may have a structure of a single layer formed of a plurality of different materials, or a structure in which a hole injection layer HIL/a hole transport layer HTL, a hole injection layer HIL/a hole transport layer HTL/a buffer layer, a hole injection layer HIL/a buffer layer, a hole transport layer HTL/a buffer layer, or a hole injection layer HIL/a hole transport layer HTL/an electron blocking layer EBL are stacked in order from the first electrode EL1. However, embodiments of the present disclosure are not limited thereto.

In some embodiments, the hole transport region HTR may have a stacked structure of a plurality of hole transport layers. For example, the hole transport region HTR may have a structure of a hole injection layer HIL/a first hole transport layer HTL1/a second hole transport layer HTL2. However, embodiments of the present disclosure are not limited thereto.

The hole transport region HTR may be formed by utilizing one or more suitable methods (such as a vacuum deposition method, a spin coating method, a cast method, a Langmuir-Blodgett (LB) method, an inkjet printing method, a laser printing method, and/or a laser induced thermal imaging (LITI) method).

In the light-emitting element ED according to an embodiment, the hole transport region HTR may include an amine compound represented by Formula 1. In the light-emitting element ED according to an embodiment, the hole transport layer HTL may include the amine compound represented by Formula 1, and for example, in the light-emitting element ED according to an embodiment, the first hole transport layer HTL1 may include the amine compound represented by Formula 1:

Formula 1

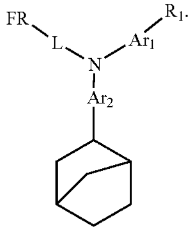

In Formula 1, $R_1$ may be an adamantyl group, a cyclohexyl group, or a bicycloheptyl group, and FR may be represented by Formula 2:

Formula 2

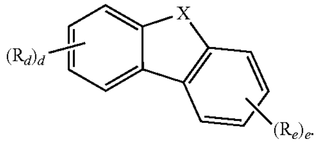

For example, the amine compound according to an embodiment may include: a first substituent of (e.g., that is) a bicycloheptyl group; a second substituent selected from an adamantyl group, a cyclohexyl group, and a bicycloheptyl group; and a third substituent selected from a fluorenyl group and a dibenzoheterole group, each substituent being bonded to an N atom (e.g., the central N atom). For example, the bicycloheptyl group utilized as a substituent in the amine compound according to an embodiment may be an unsubstituted bicyclo[2,2,1]heptyl group (e.g., a norbornyl group). For example, in the amine compound according to an embodiment, $R_1$ may be an unsubstituted adamantyl group, an unsubstituted cyclohexyl group, or an unsubstituted bicyclo[2,2,1]heptyl group.

In some embodiments, "FR" represented by Formula 2 may be bonded to L of Formula 1 or the N atom of the amine compound (e.g., when L is a direct linkage) via position X or via any one of the ring-forming carbon atoms of the benzene ring, as represented by Formula 2A or Formula 2B. In Formula 2A and Formula 2B, "——*" refers to a position to be connected.

Formula 2A

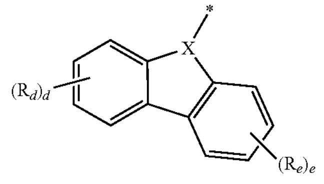

Formula 2B

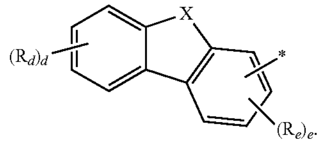

In Formula 1, $Ar_1$ and $Ar_2$ may each independently be a substituted or unsubstituted arylene group having 6 to 30 ring-forming carbon atoms. For example, $Ar_r$ and $Ar_2$ may each independently be a substituted or unsubstituted phenylene group. For example, in an embodiment, $Ar_1$ and $Ar_2$ may each be an unsubstituted phenylene group.

In Formula 1, L may be a direct linkage, a substituted or unsubstituted arylene group having 6 to 30 ring-forming carbon atoms, or a substituted or unsubstituted heteroarylene group having 2 to 30 ring-forming carbon atoms. When L is a direct linkage, the nitrogen atom (N) of the amine and "FR" group in Formula 1 may be directly bonded to each other via a single bond. In some embodiments, L may be a substituted or unsubstituted phenylene.

In Formula 2, X may be $CR_aR_b$, N, $NR_c$, O, or S. For example, the "FR" group represented by Formula 2 may be a substituted or unsubstituted fluorene derivative, a substituted or unsubstituted carbazole derivative, a substituted or unsubstituted dibenzofuran derivative, or a substituted or unsubstituted dibenzothiophene derivative.

In Formula 2, $R_a$ to $R_c$ may each independently be a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring.

In Formula 2, d and e may each independently be an integer of 0 to 4. In some embodiments, in Formula 2, $R_d$ and $R_e$ may each independently be a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring.

In Formula 2, when d is 0, $R_d$ is not substituted in Formula 2 (e.g., Formula 2 does not include any $R_d$ substituents), and when e is 0, $R_e$ is not substituted in Formula 2 (e.g., Formula 2 does not include any $R_e$ substituents). For example, when both (e.g., simultaneously) d and e are 0 in Formula 2, the benzene rings of Formula 2 may be unsubstituted. When d is an integer of 2 or more in Formula 2, all the plurality of $R_d$ may be the same, or at least one thereof may be different from the others. In some embodiments, when e is an integer of 2 or more, the plurality of $R_e$ may be the same or at least one thereof may be different from the others.

In some embodiments, when X is represented by $CR_aR_b$ in Formula 2, $R_a$ and $R_b$ may each independently be a linear alkyl group, a cyclic alkyl group, or an aryl group, and/or the like. In some embodiments, $R_a$ and $R_b$ may be bonded to each other to form a ring. $R_a$ and $R_b$ may be bonded to a fluorene ring, and "FR" represented by Formula 2 may have a spiro structure.

In some embodiments, when "FR" is represented by Formula 2 in which X is $CR_aR_b$, $R_a$ or $R_b$ may be directly bonded to L, or $R_a$ or $R_b$ may directly bonded to the nitrogen atom (N) of the amine (e.g., when L is a direct linkage).

In an embodiment, the amine compound represented by Formula 1 may be represented by Formula 1-1 or Formula 1-2. In Formula 1-1 and Formula 1-2, $R_1$, L, $Ar_1$, and $Ar_2$ may each independently be the same as described for Formula 1, and X, $R_d$, $R_e$, d, and e may each independently be the same as described for Formula 2:

Formula 1-1

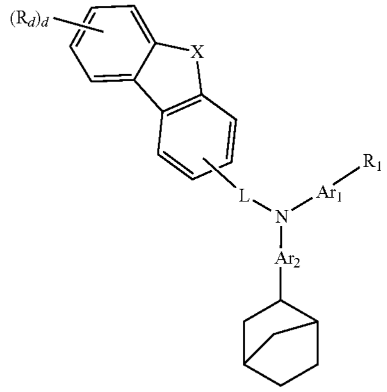

Formula 1-2

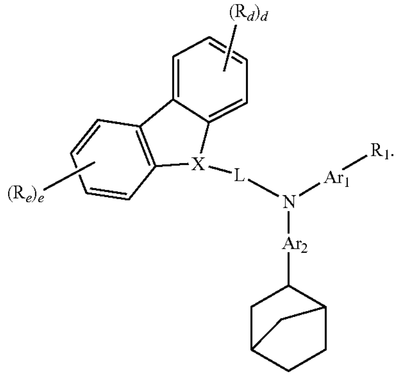

In some embodiments, the amine compound represented by Formula 1-2 may be represented by Formula 1-2A. In Formula 1-2A, $R_1$, L, $Ar_1$, and $Ar_2$ may each independently be the same as described for Formula 1, and $R_a$, $R_d$, $R_e$, d, and e may each independently be the same as described for Formula 2:

Formula 1-2A

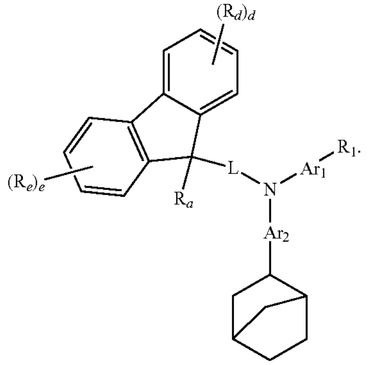

In some embodiments, the amine compound represented by Formula 1 may be represented by Formula 1A. For example, in the amine compound represented by Formula 1 according to an embodiment, both $Ar_1$ and $Ar_2$ may be an unsubstituted phenylene group (e.g., simultaneously):

Formula 1A

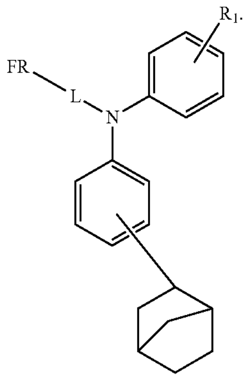

In some embodiments, the amine compound represented by Formula 1A may be represented by Formula 1A-1. For example, in the amine compound represented by Formula 1 according to an embodiment, a bicycloheptyl group (e.g., bicyclo[2,2,1]heptyl group) and a substituent represented by R1 may respectively be bonded to the nitrogen atom (N) via a phenylene linker at a para position to the amine. However, embodiments of the present disclosure are not limited thereto.

Formula 1A-1

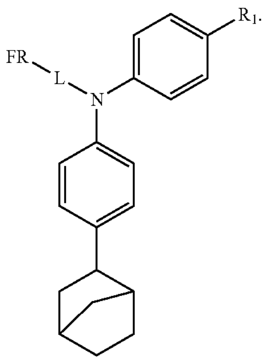

In some embodiments, in Formula 1A and Formula 1A-1, $R_1$, L, and, FR may each independently be the same as described for Formula 1.

The amine compound represented by Formula 1 according to an embodiment may be represented by any one of the compounds in Compound Group 1. The hole transport region HTR of the light-emitting element ED according to an embodiment may include at least one of the amine compounds disclosed in Compound Group 1.

Compound Group 1

1

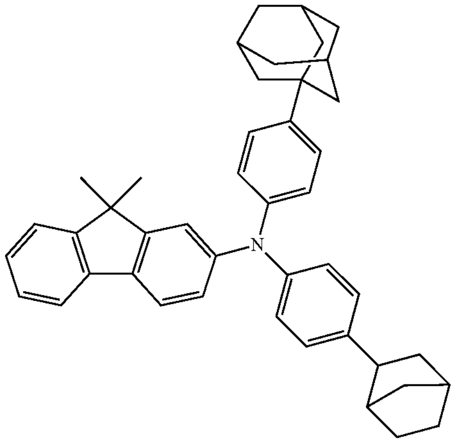

2

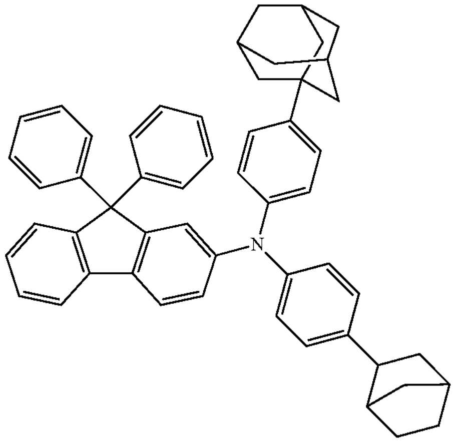

3

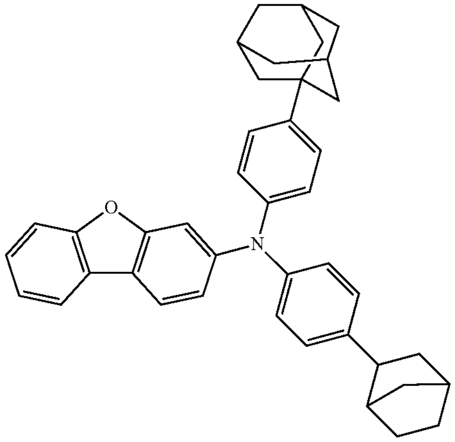

-continued
4
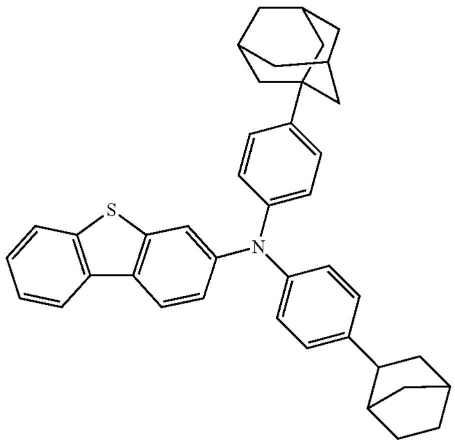
5
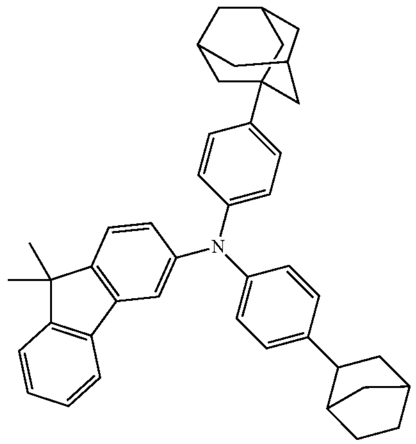
6
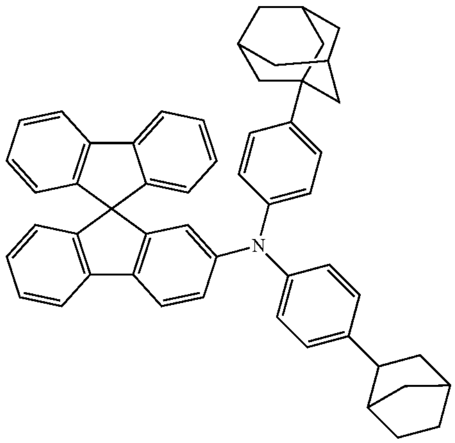
-continued
7
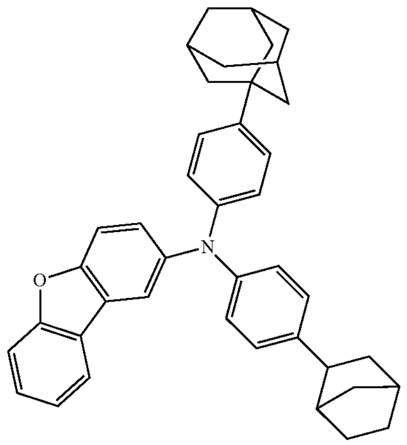
8
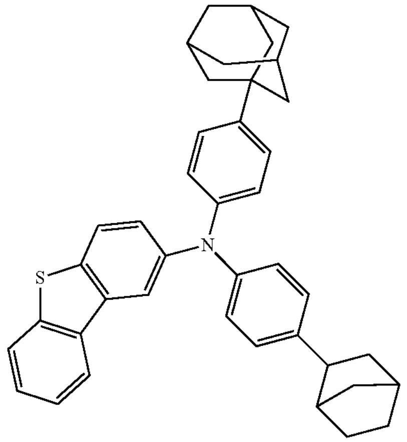
9
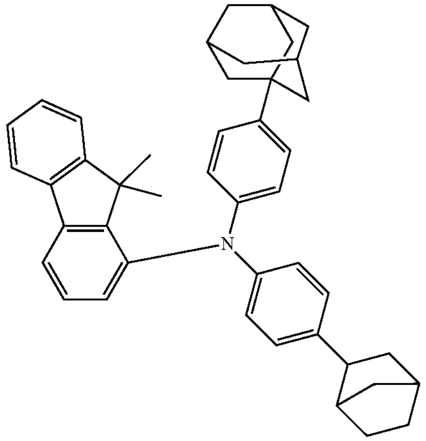

-continued
10
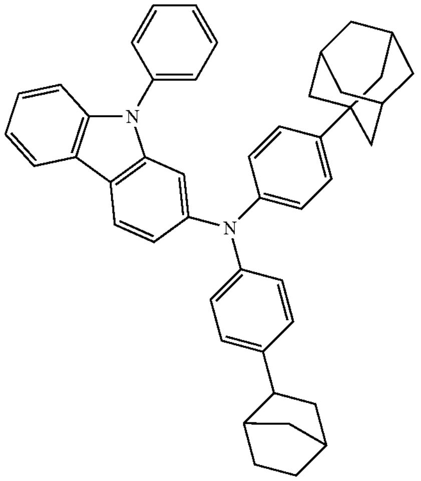
11
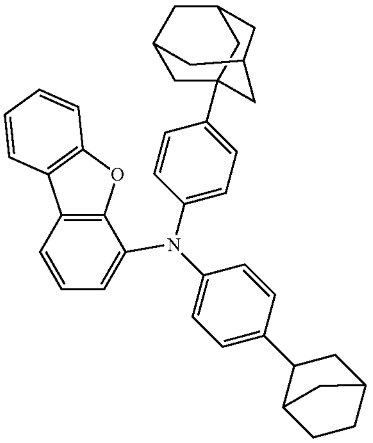
12
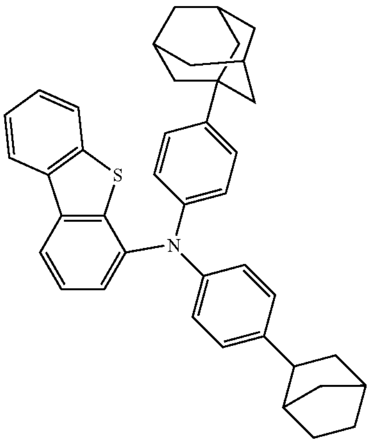
-continued
13
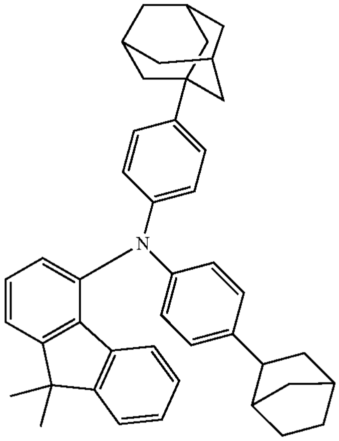
14
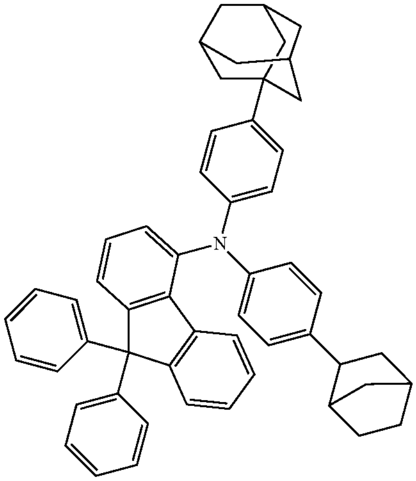
15
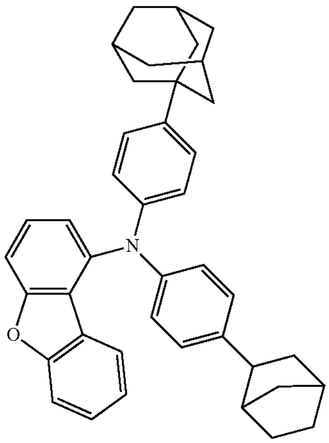

-continued
16
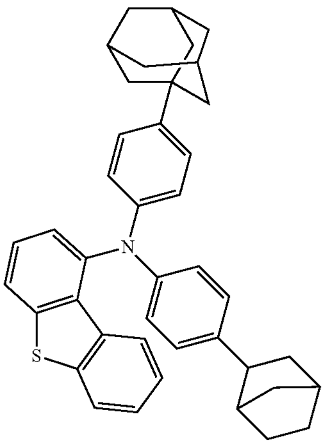
17
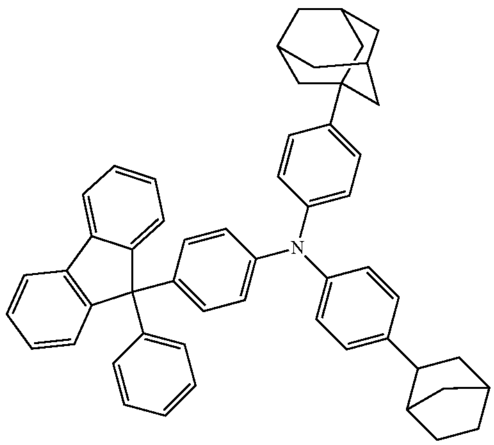
18
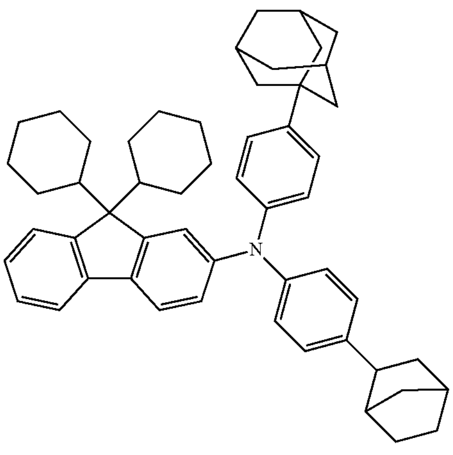
-continued
19
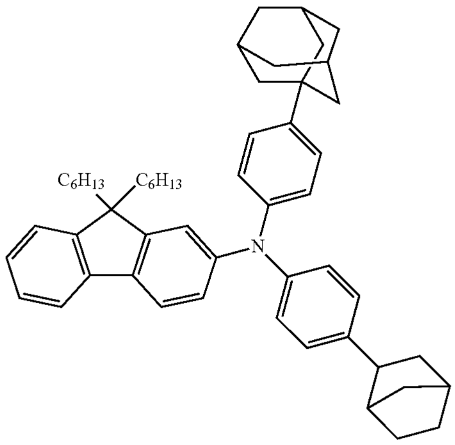
20
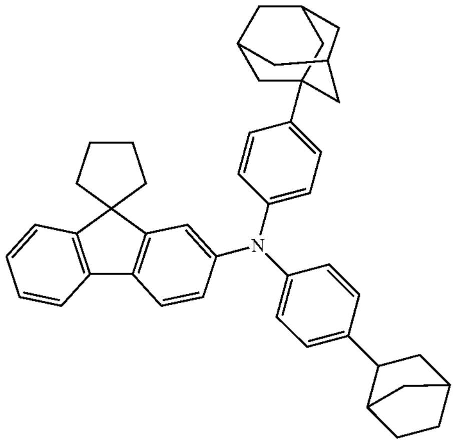
21
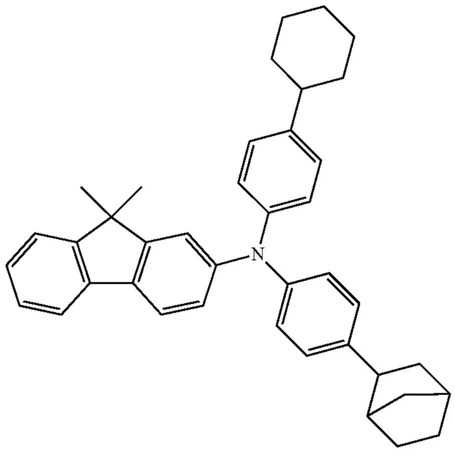

-continued
22
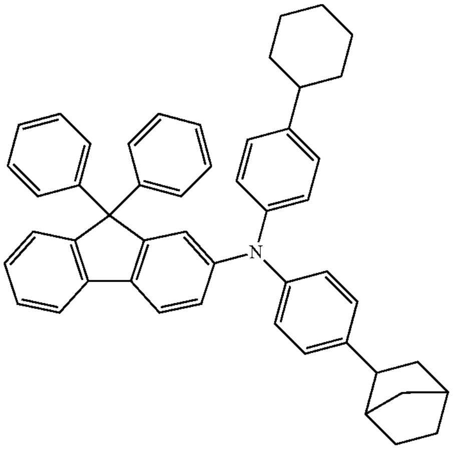
23
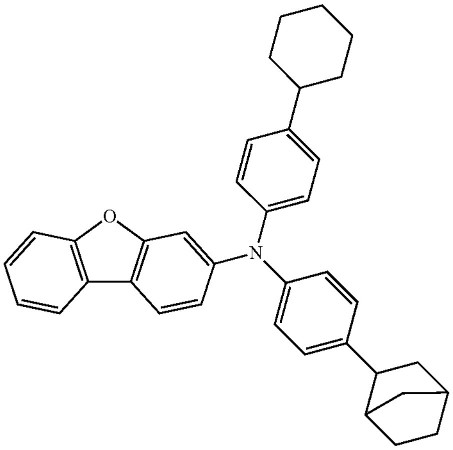
24
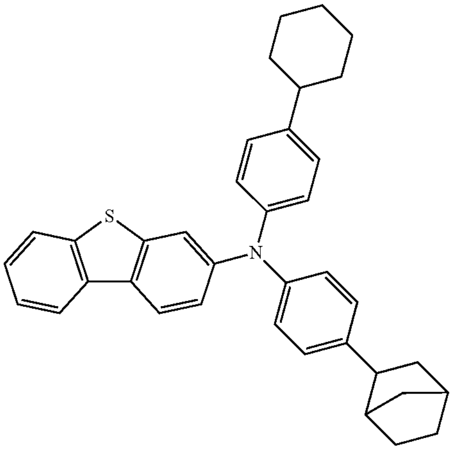
-continued
25
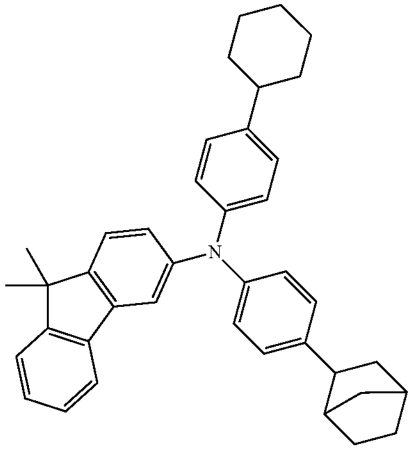
26
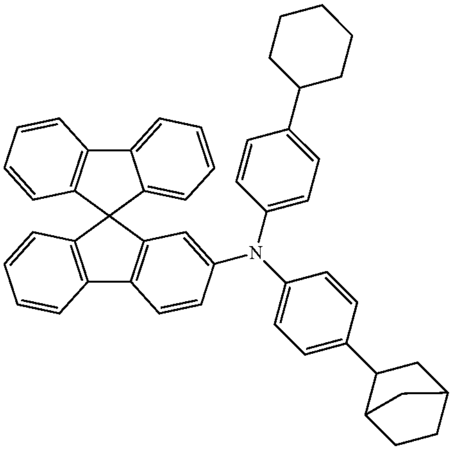
27
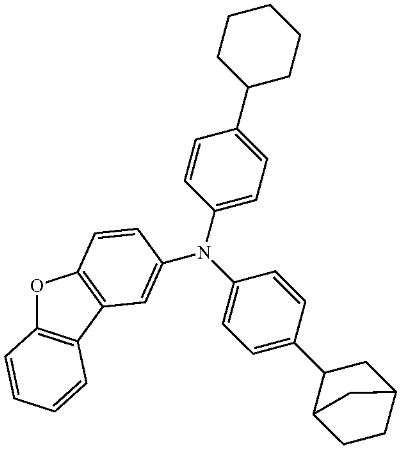

-continued
28
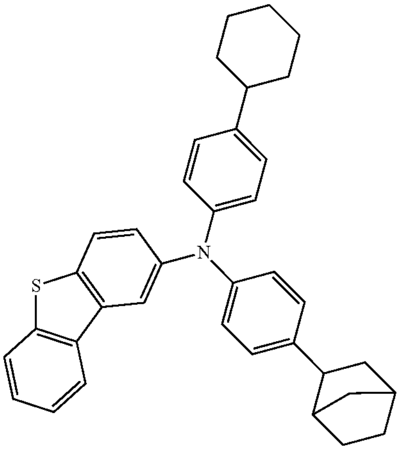
29
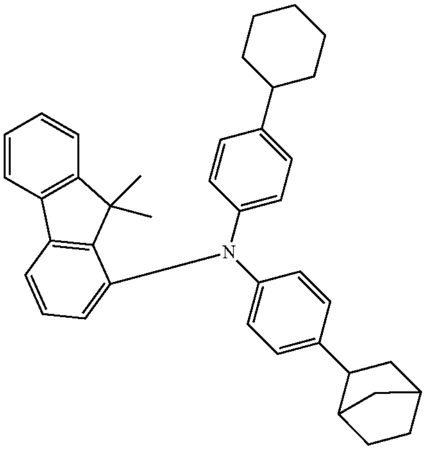
30
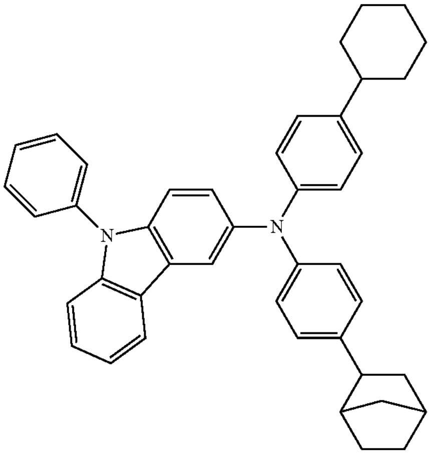
-continued
31
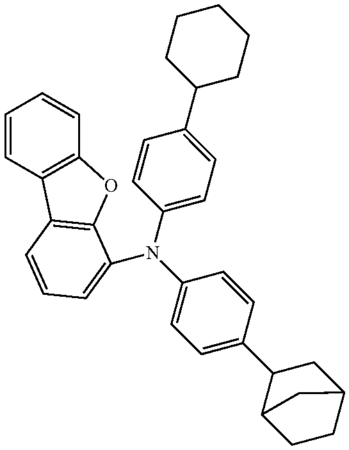
32
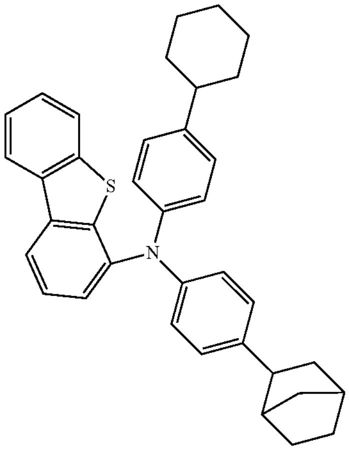
33
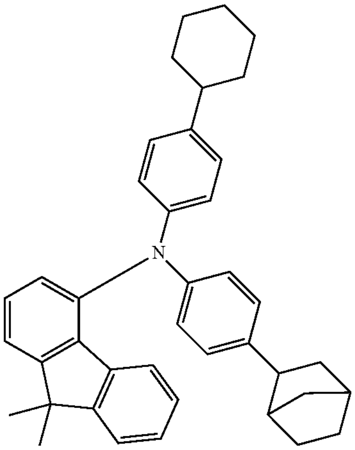

-continued
34
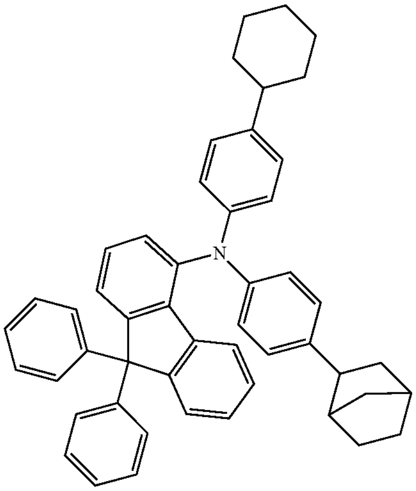
35
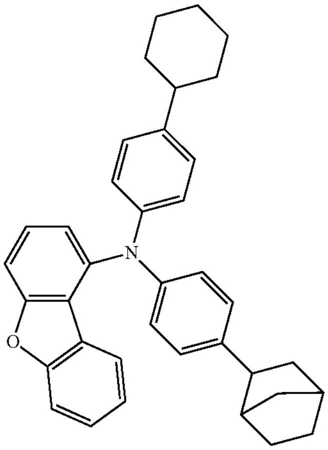
36
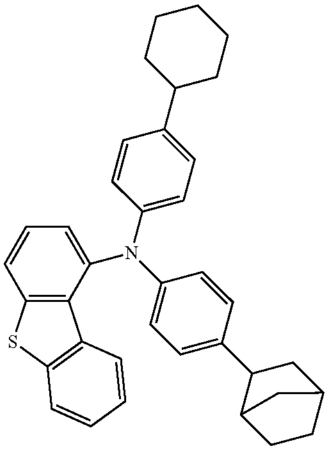
-continued
37
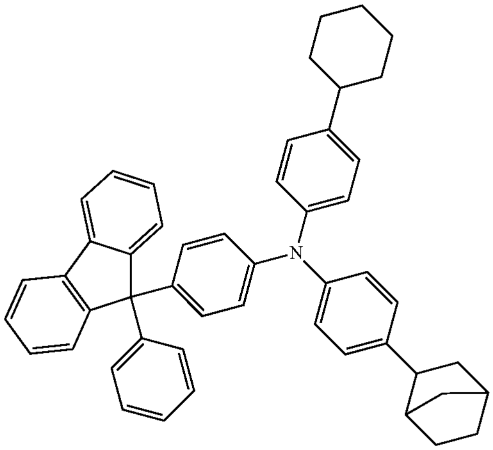
38
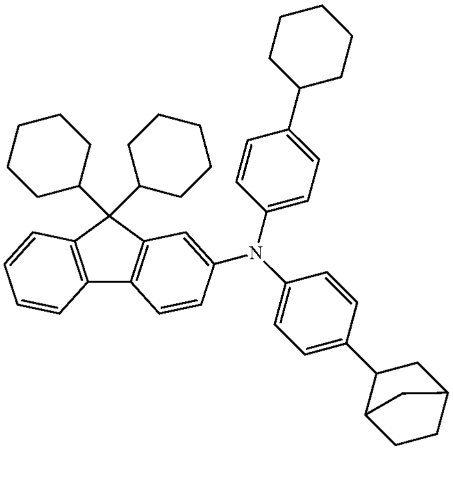
39
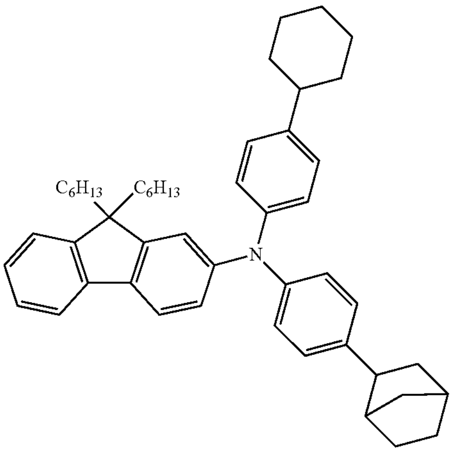

-continued
40
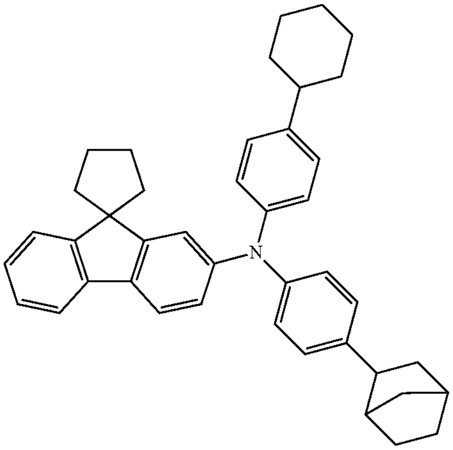
41
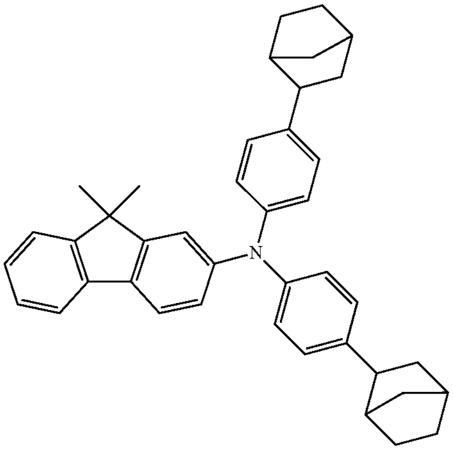
42
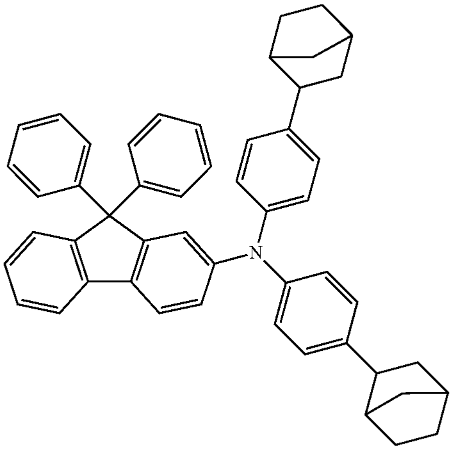
-continued
43
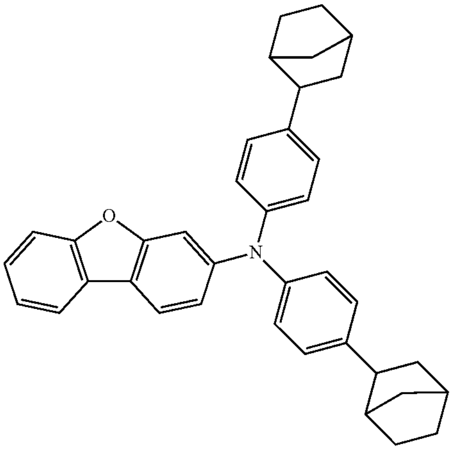
44
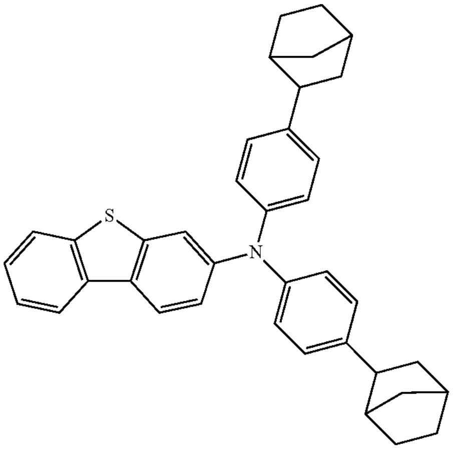
45
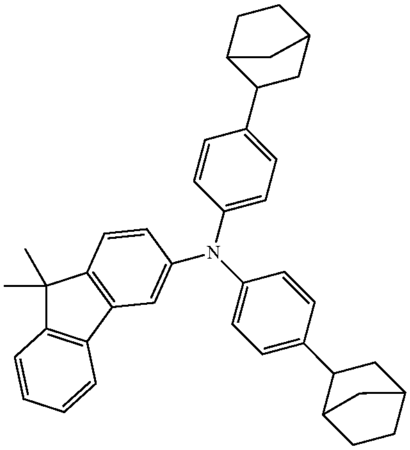

-continued
46
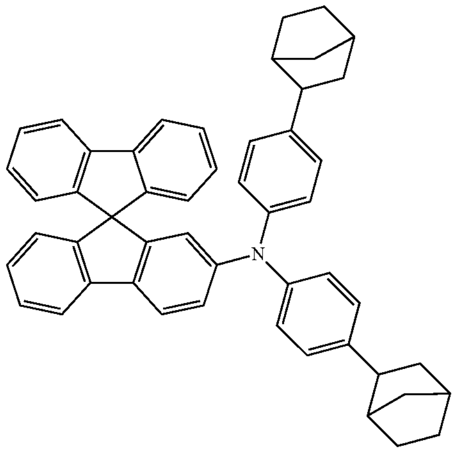
47
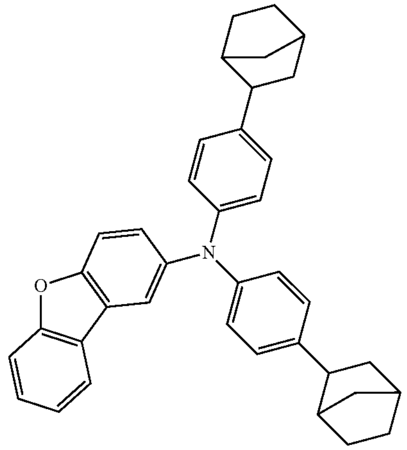
48
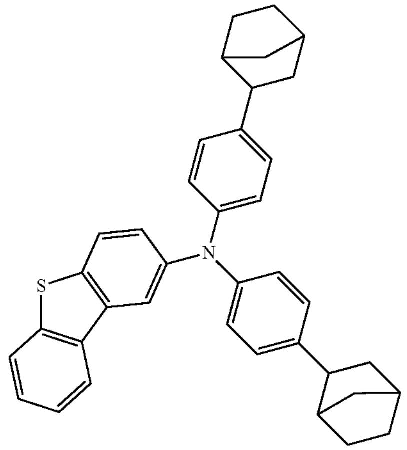
-continued
49
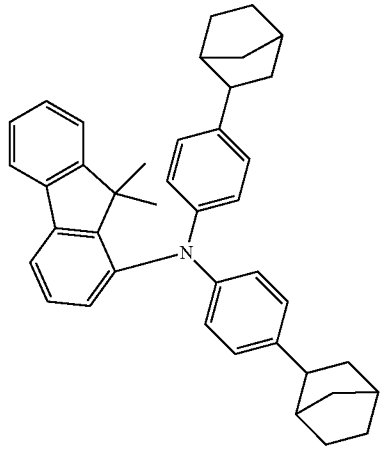
50
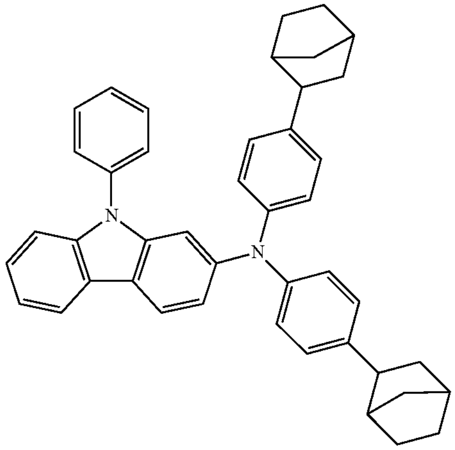
51
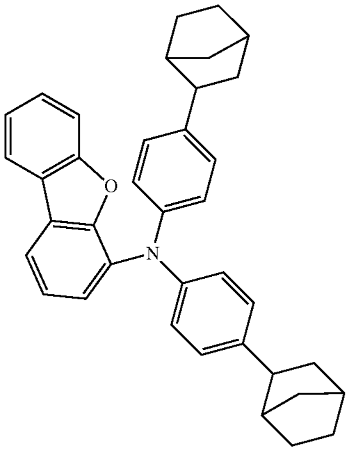

52
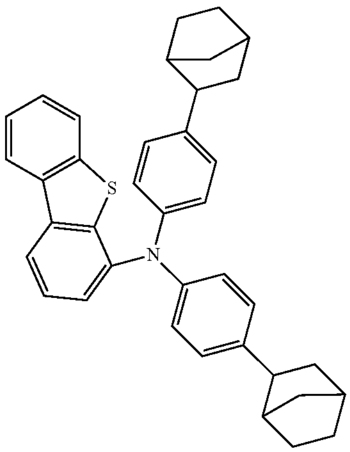
53
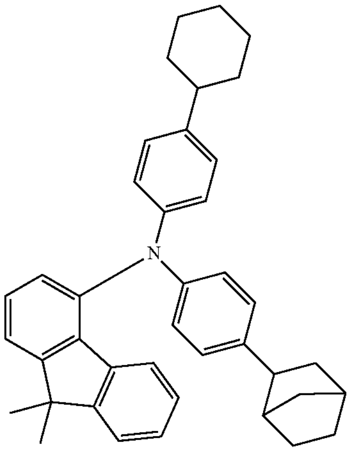
54
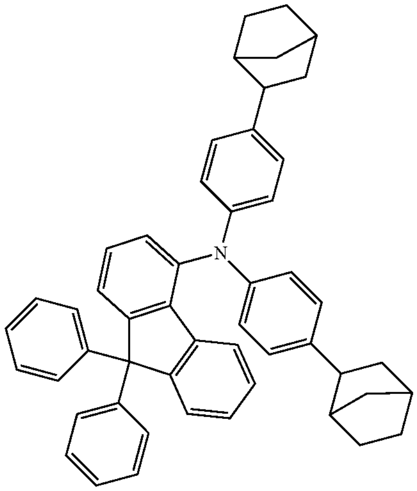
55
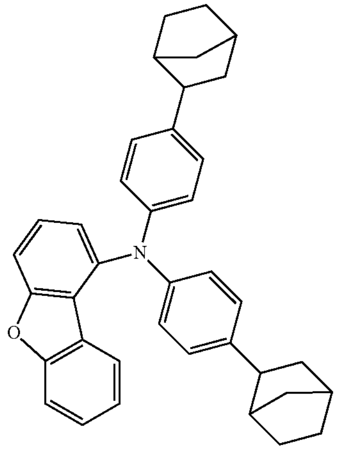
56
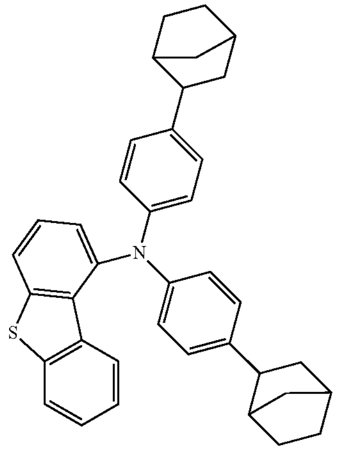
57
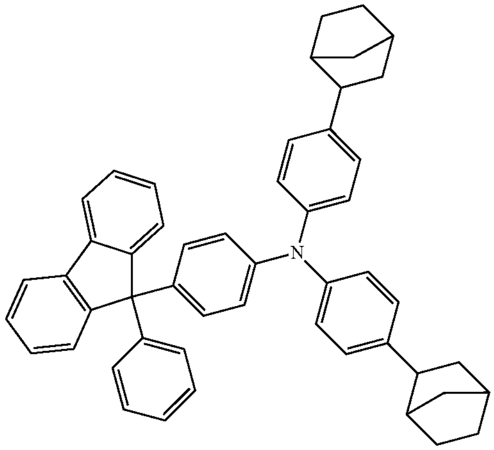

-continued
58
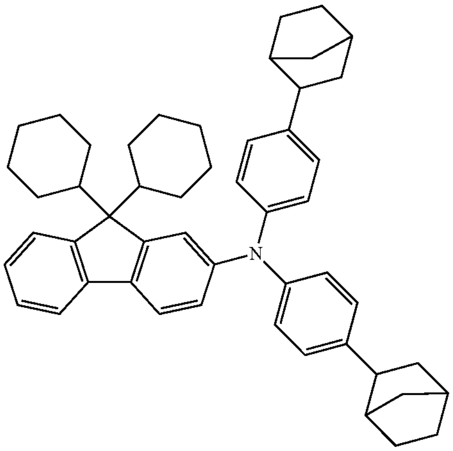
59
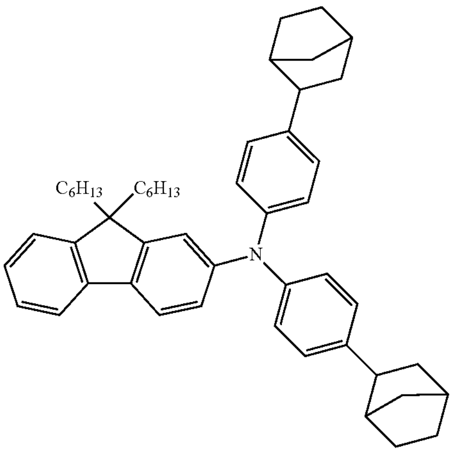
60
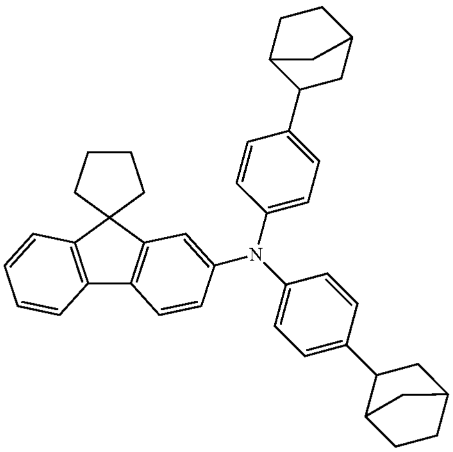
-continued
61
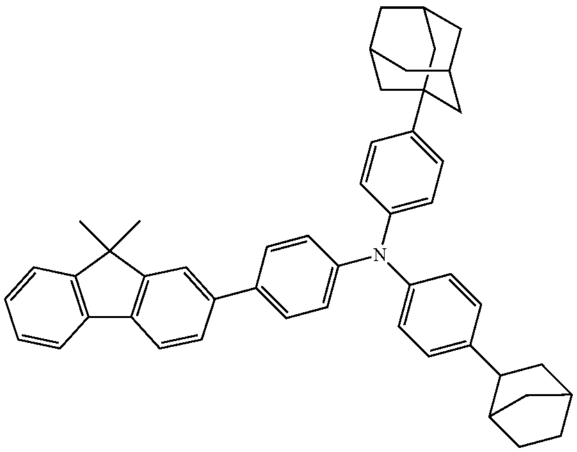
62
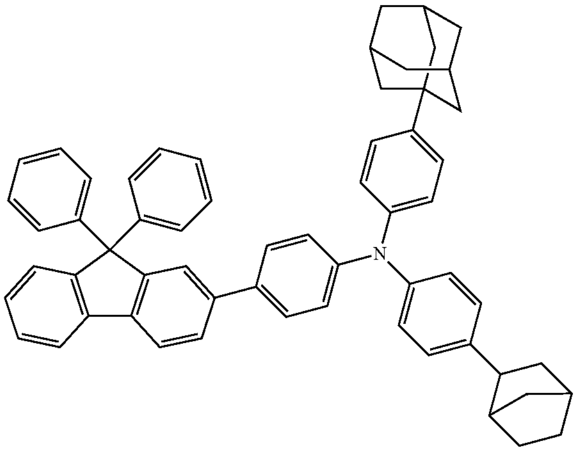
63
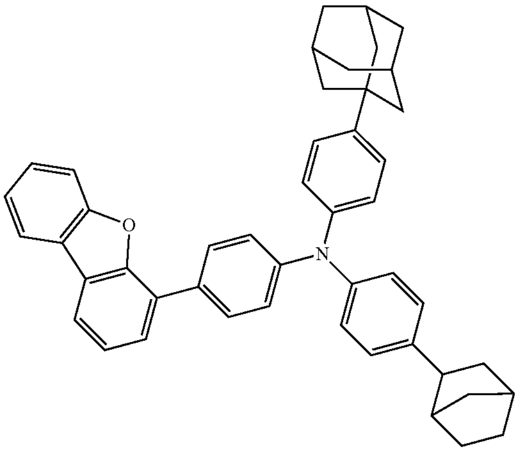

-continued
64
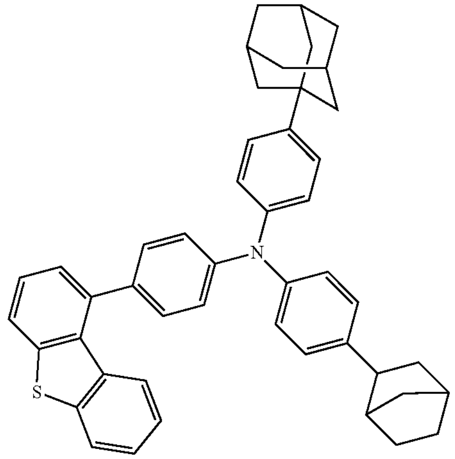
65
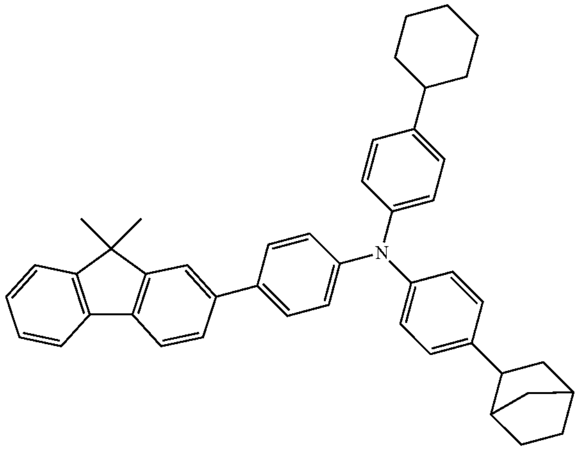
66
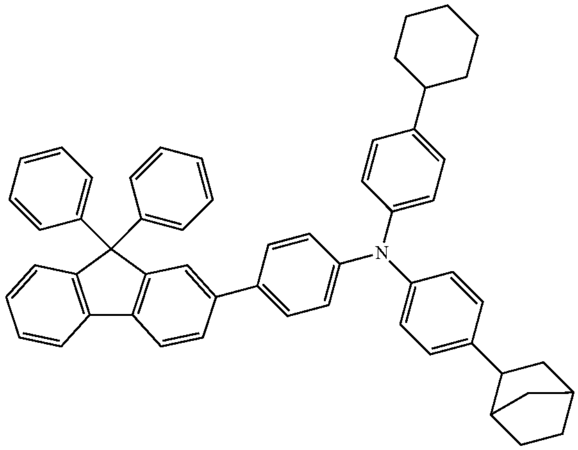
-continued
67
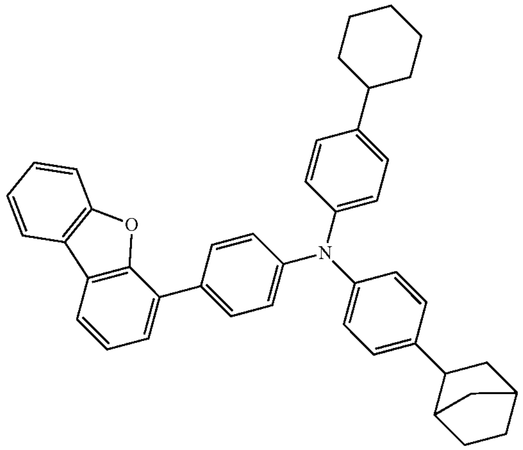
68
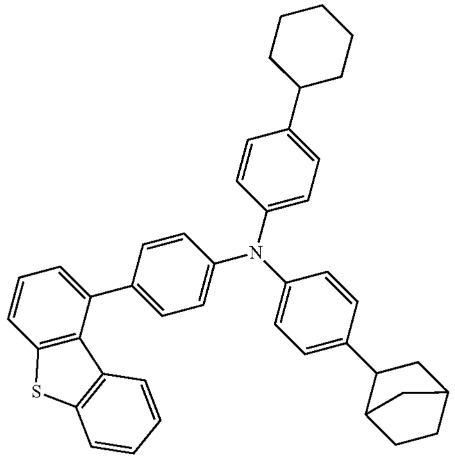
69
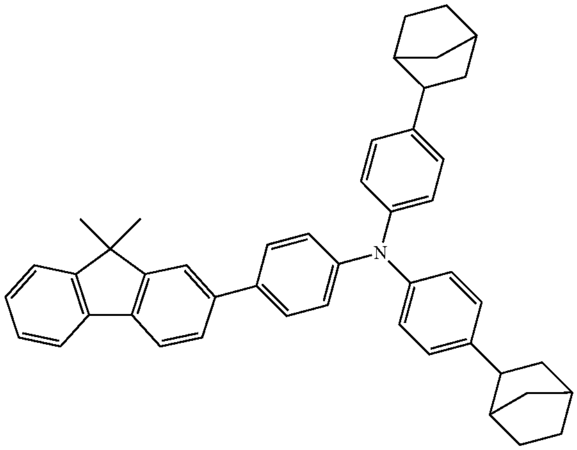

-continued

70

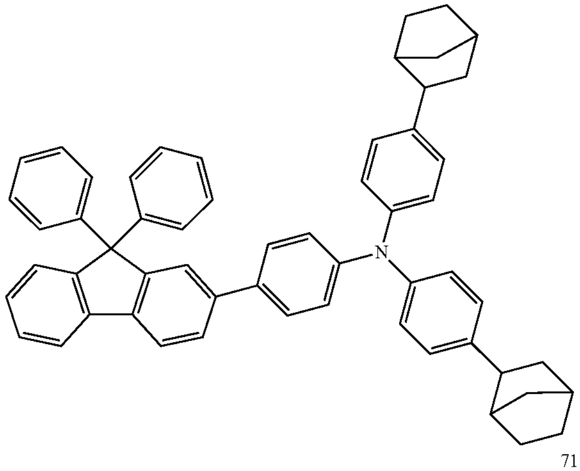

71

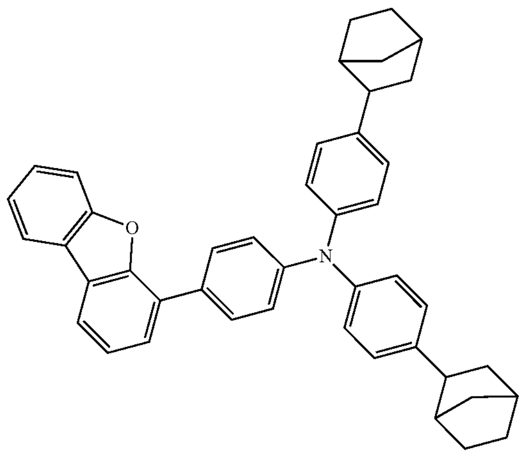

72

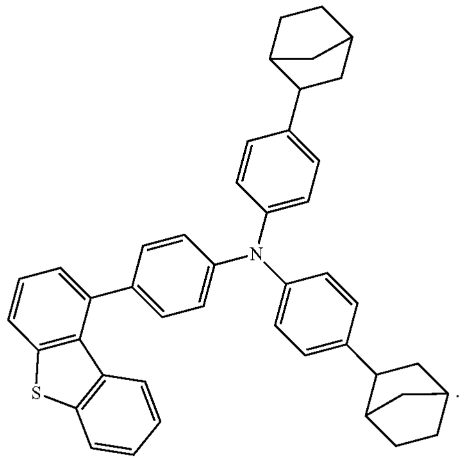

The amine compound represented by Formula 1 according to an embodiment has a substituent structure essentially containing one bicycloheptyl group, and further essentially containing one of a bicycloheptyl group, a cyclohexyl group, or an adamantyl group, and may thereby have a high glass transition temperature characteristics. Such high glass transition temperature characteristics may lead to excellent or suitable heat resistance and/or durability. In some embodiments, the substituent structure of the presented amine compound may facilitate a lower deposition temperature in a deposition process to form a film, and thus productivity of the process for forming a film may be increased.

When the amine compound according to an embodiment is utilized in the hole transport region, the external quantum efficiency of the device may be increased by changing a light extraction mode and/or a refractive index variation between the first electrode and the second electrode. Accordingly, use of the amine compound according to an embodiment in the hole transport region may increase the emission efficiency of the light-emitting element and improve the service life of the light-emitting element. In some embodiments, the service life and/or emission efficiency of the light-emitting element according to an embodiment may be improved by including, as a material for light-emitting element, the amine compound according to an embodiment, which has excellent or suitable heat resistance and/or durability.

In some embodiments, when the light-emitting element ED according to an embodiment includes a plurality of a hole transport layers HTL1 and HTL2, a first hole transport layer HTL1 adjacent to a first electrode EL1 may include the amine compound represented by Formula 1 described according to an embodiment. In some embodiments, a second hole transport layer HTL2 disposed on the first a hole transport layer HTL1, and adjacent to the emission layer EML may include an amine derivative compound represented by Formula 3.

Formula 3

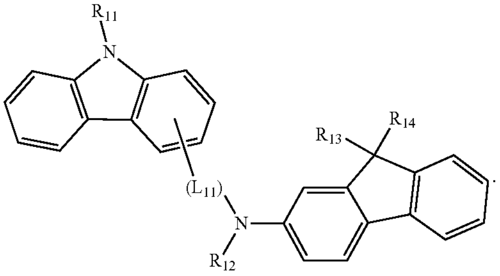

In Formula 3, $L_{11}$ may be a direct linkage, a substituted or unsubstituted arylene group having 6 to 30 ring-forming carbon atoms, or a substituted or unsubstituted heteroarylene group having 2 to 30 ring-forming carbon atoms. In some embodiments, in Formula 3, $R_{11}$ to $R_{14}$ may each independently be a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring.

For example, $L_{11}$ may be a direct linkage or a substituted or unsubstituted phenylene group. In some embodiments, $R_{11}$ may be a substituted or unsubstituted phenyl group. However, embodiments of the present disclosure are not limited thereto.

In an amine derivative represented by Formula 3, $R_{12}$ may be an aryl group or a heteroaryl group. For example, $R_{12}$ may be a substituted or unsubstituted phenyl group, a substituted or unsubstituted naphthyl group, a substituted or unsubstituted biphenyl group, a substituted or unsubstituted dibenzofuran group, or a substituted or unsubstituted dibenzothiophene group.

The amine derivative represented by Formula 3 may be represented by Formula 3-1 or Formula 3-2. In Formula 3-1 and Formula 3-2, $L_{11}$, and $R_{11}$ to $R_{14}$ may each independently be the same as described for Formula 3:

Formula 3-1

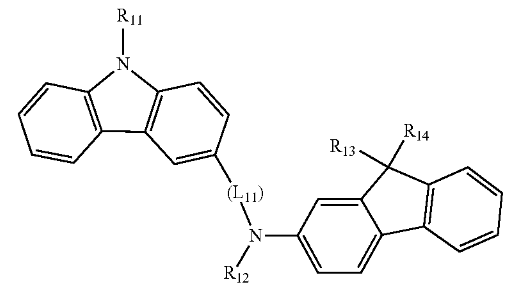

Formula 3-2

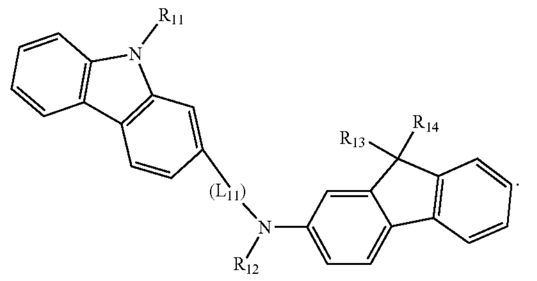

The light-emitting element ED according to an embodiment may include the amine compound according to an embodiment described above in a first hole transport layer HTL1, and the amine derivative represented by Formula 3-1 or the amine derivative represented by Formula 3-2 in a second hole transport layer HTL2.

The amine derivative represented by Formula 3-1 may be represented by any one of the compounds represented in Compound Group 2-1. For example, the second hole transport layer HTL2 may include any one of the compounds represented in Compound Group 2-1:

Compound Group 2-1

73

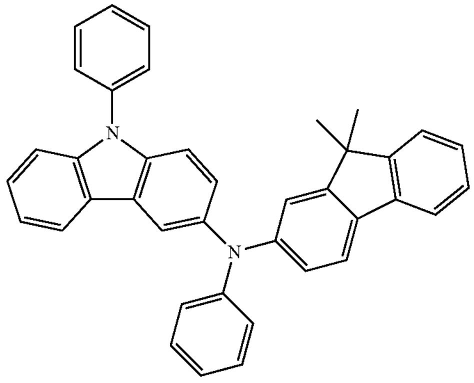

-continued

74

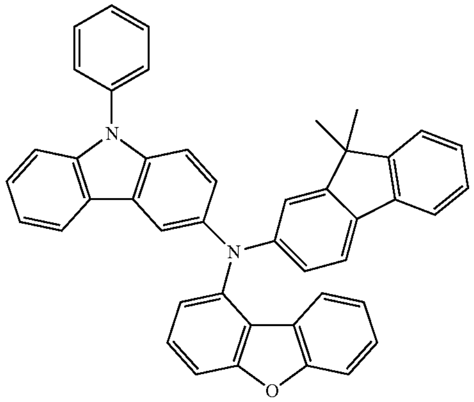

75

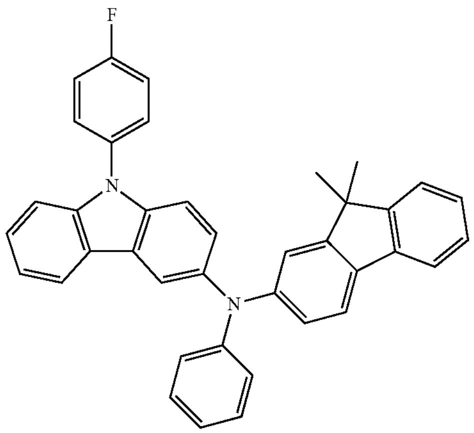

76

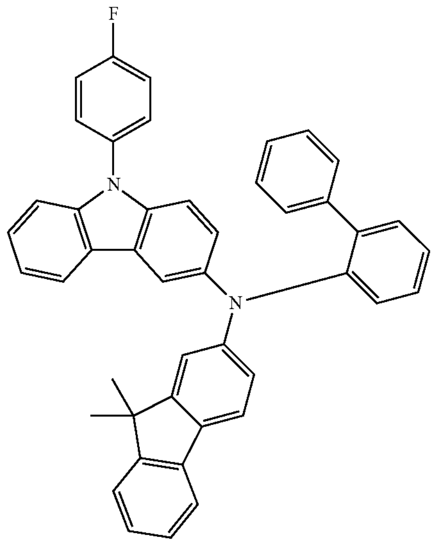

-continued
77
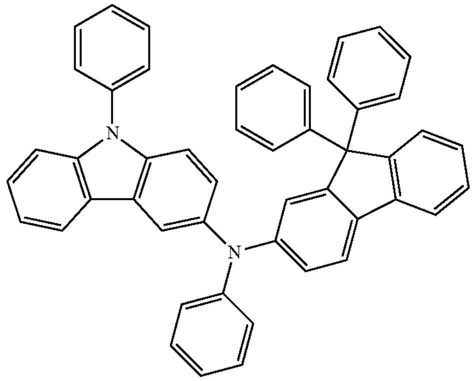
78
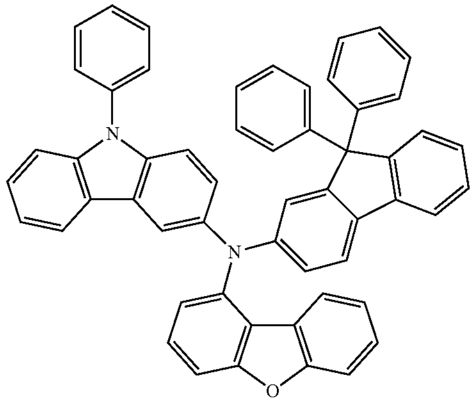
79
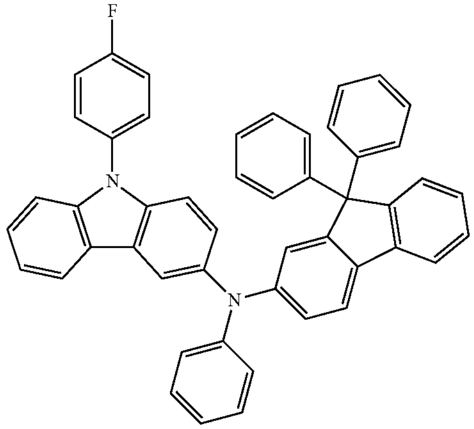
-continued
80
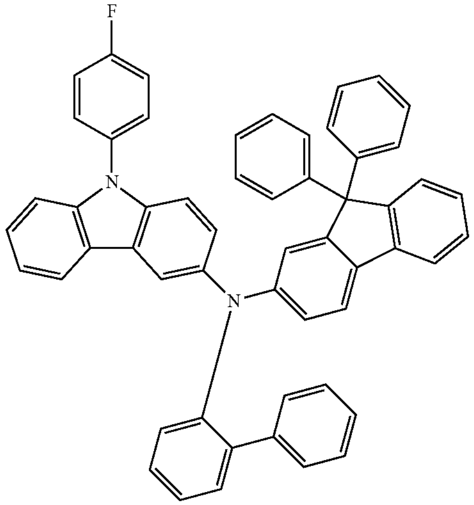
81
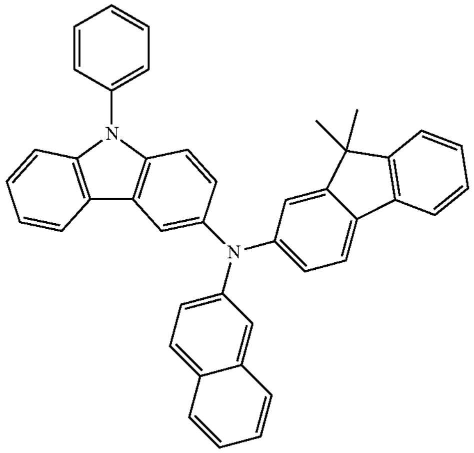
82
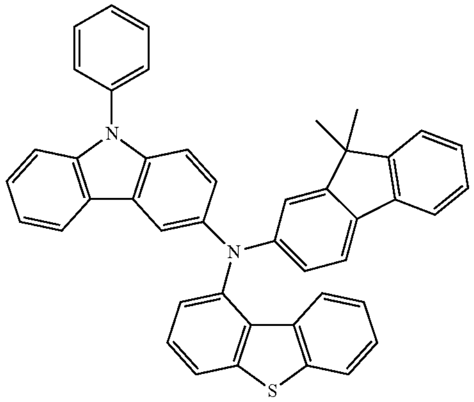

-continued
83
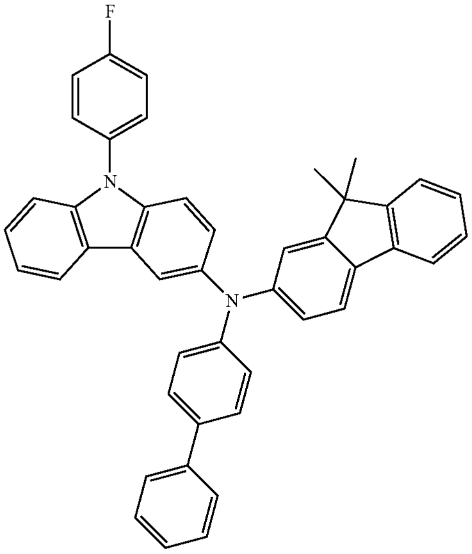
84
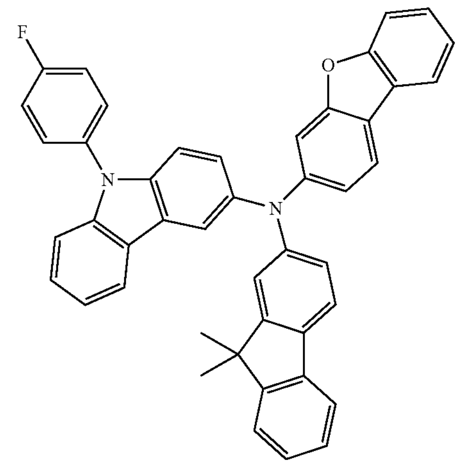
85
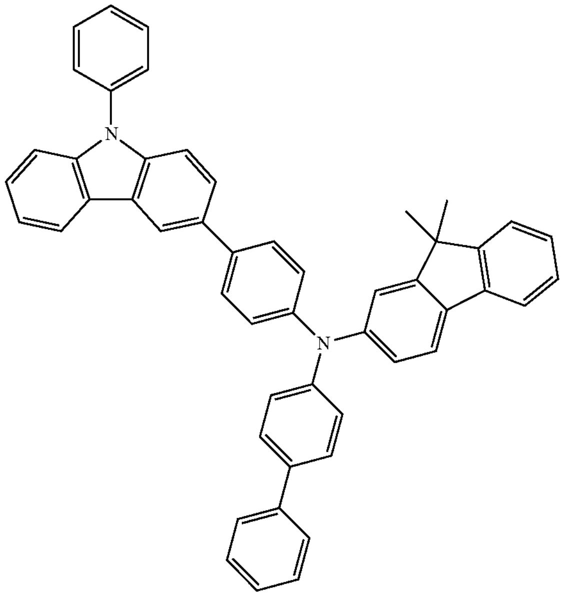
-continued
86
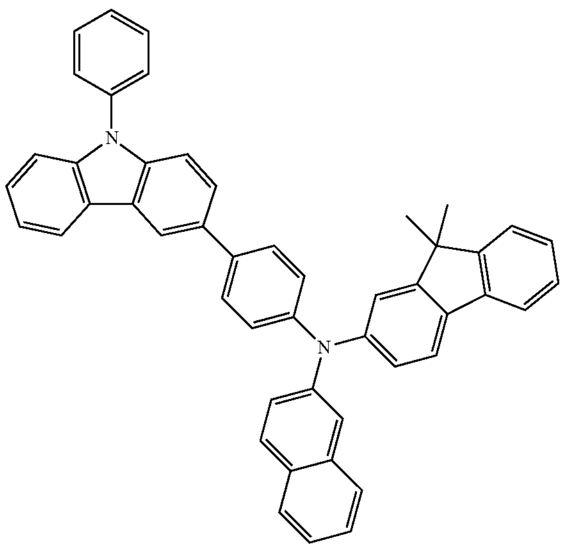
87
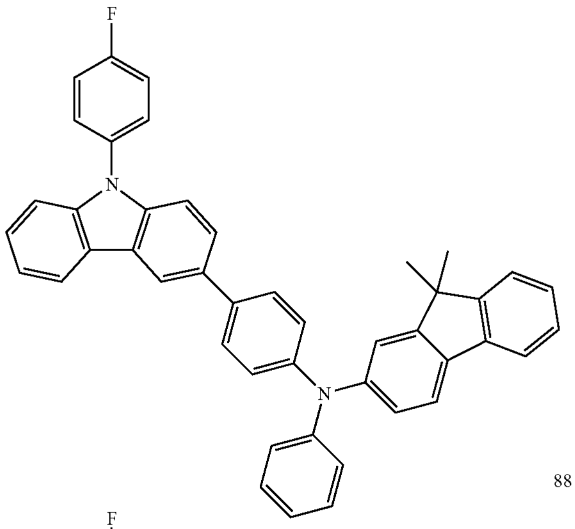
88
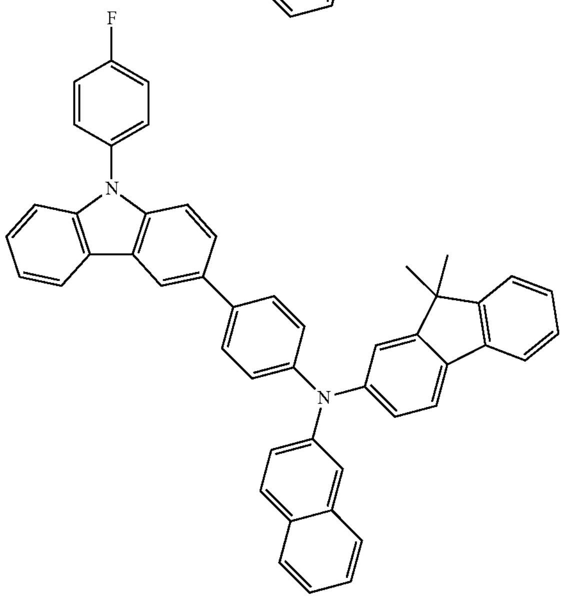

-continued
89
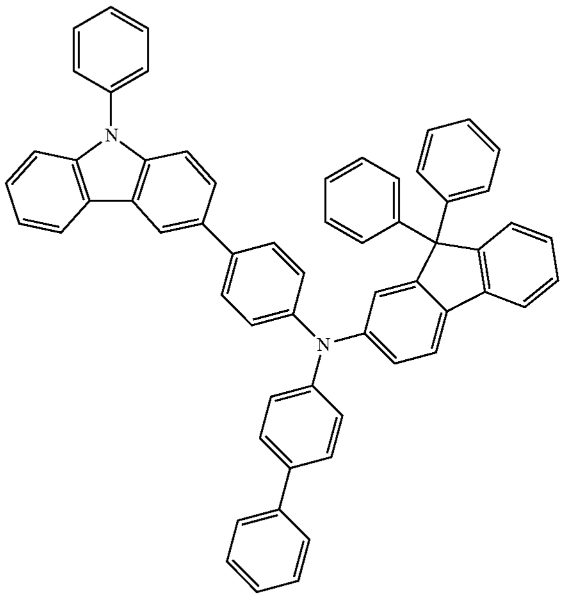
90
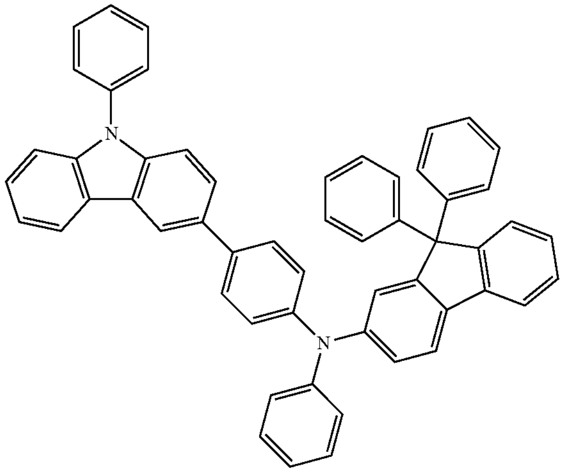
91
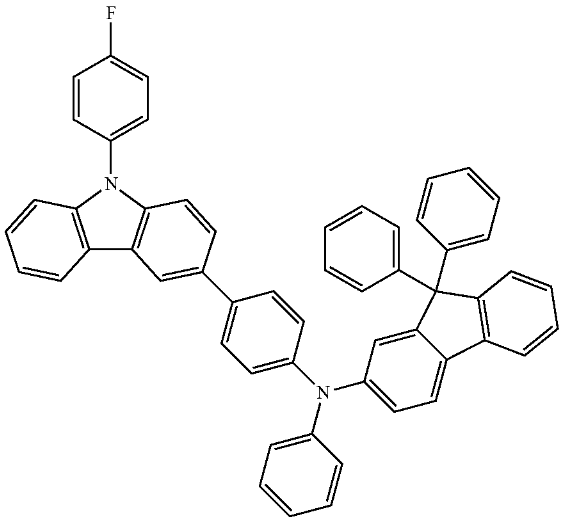
-continued
92
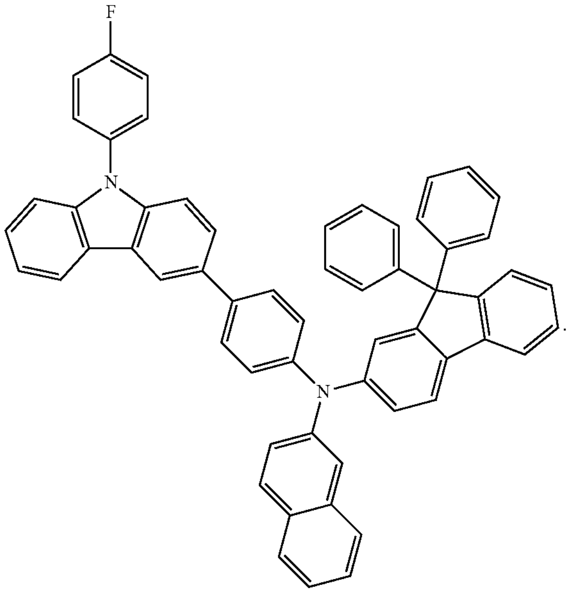
The amine derivative compound represented by Formula 3-2 may be represented by any one of the compounds represented in Compound Group 2-2. For example, the second hole transport layer HTL2 may include any one of the compounds represented in Compound Group 2-2:
Compound Group 2-2
93
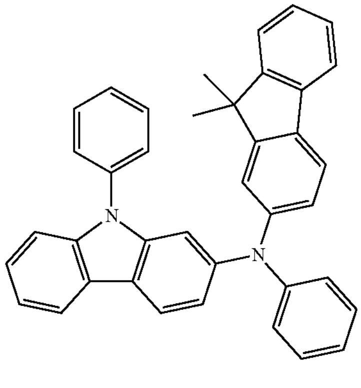
94
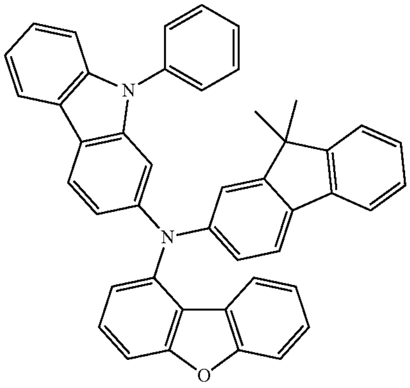

-continued
95
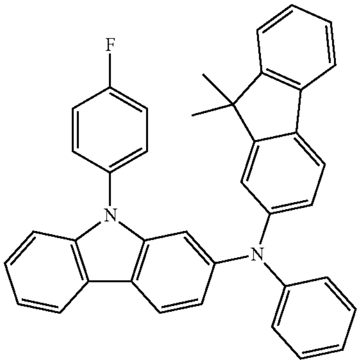
96
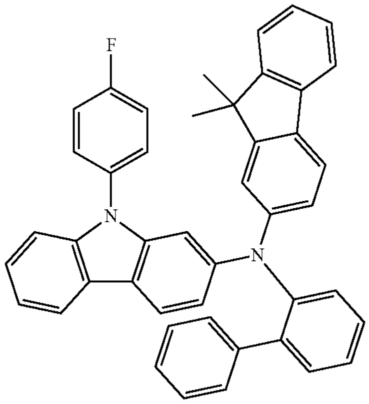
97
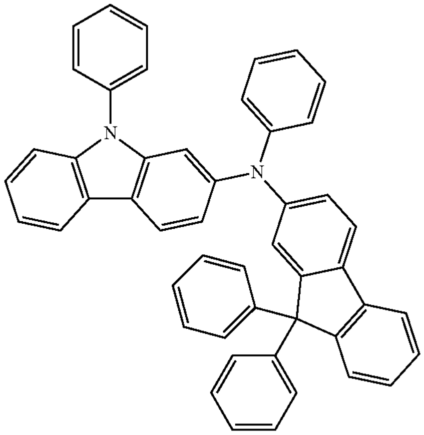
98
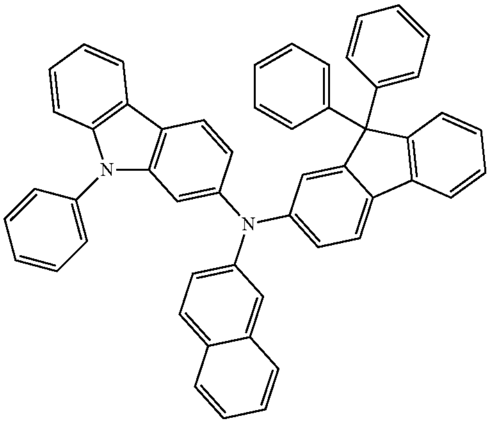
-continued
99
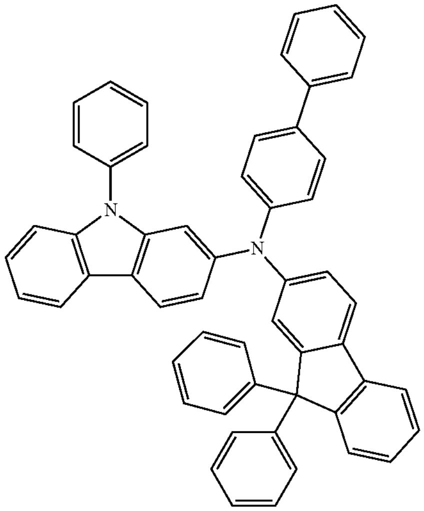
100
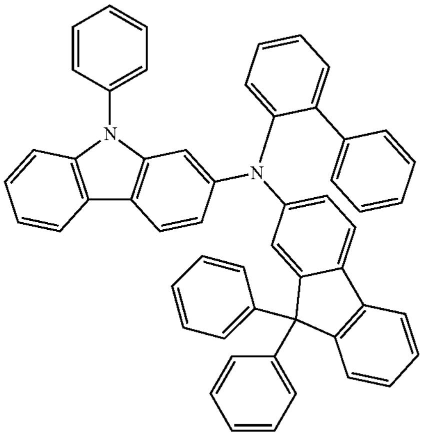
101
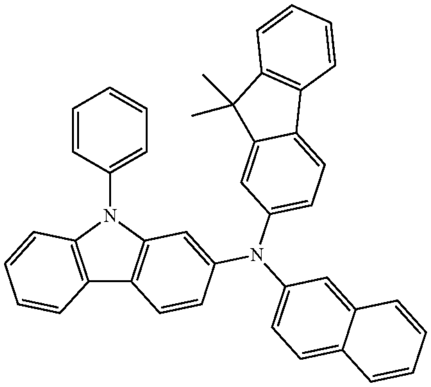

-continued
102
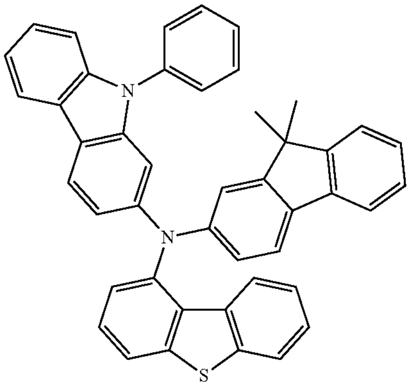
103
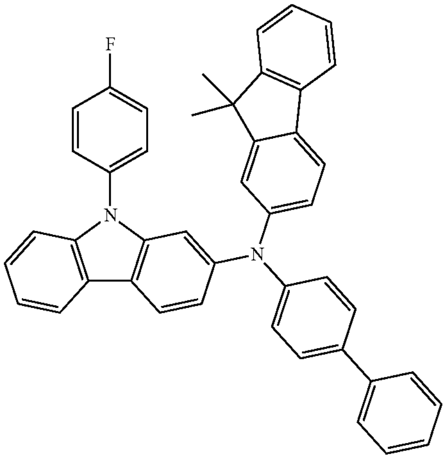
104
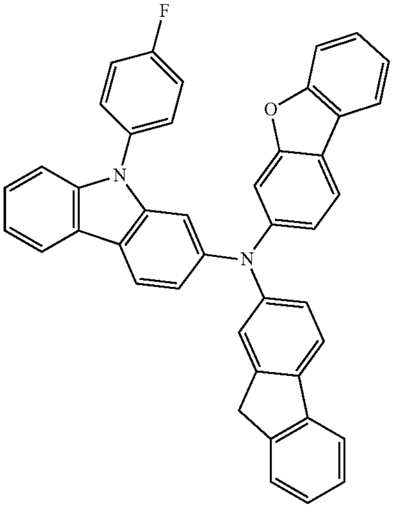
-continued
105
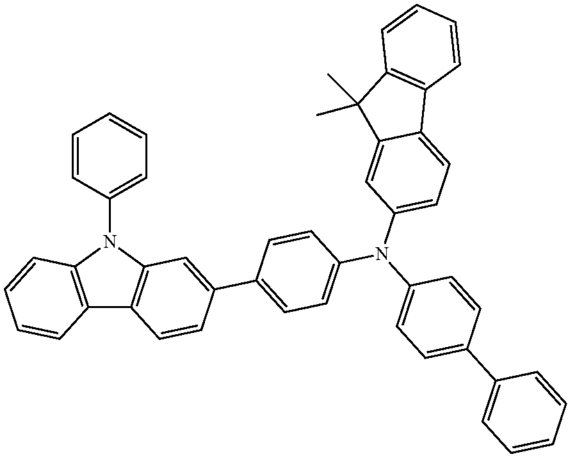
106
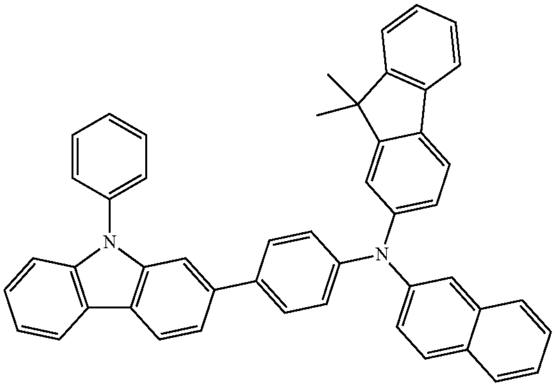
107
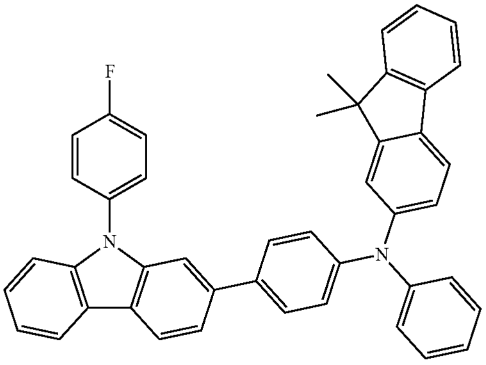

-continued

108

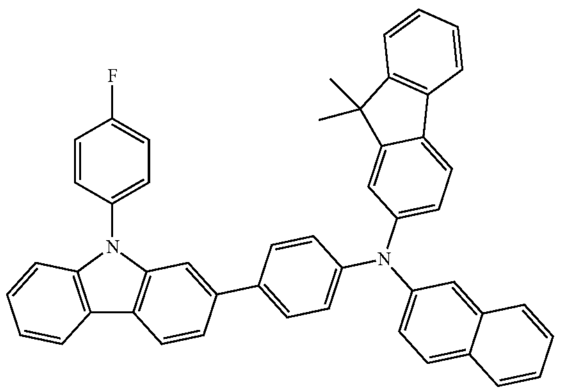

109

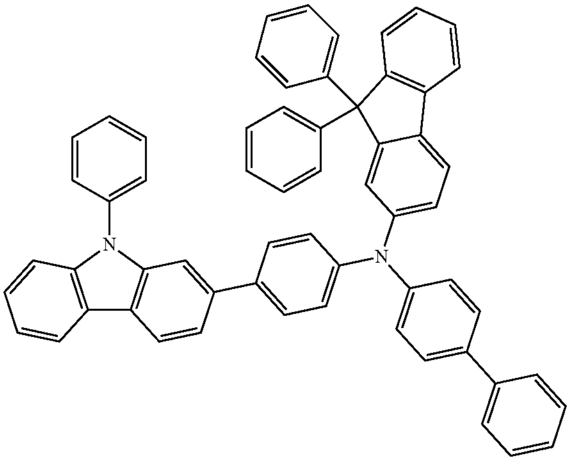

110

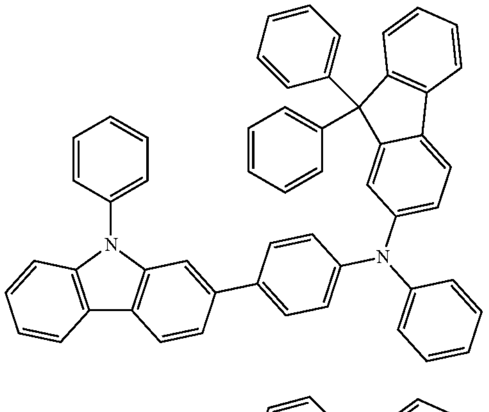

111

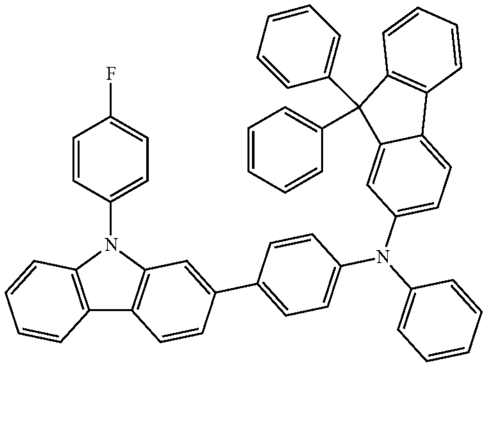

-continued

112

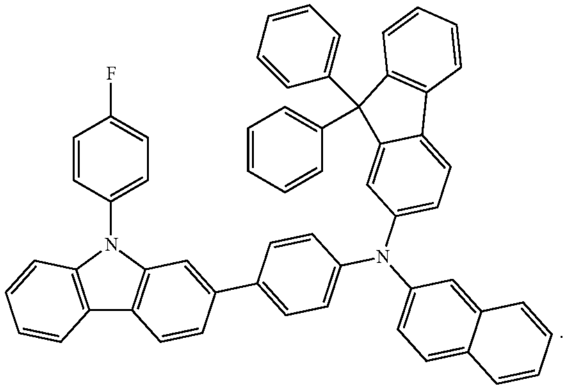

In some embodiments, the light-emitting element ED according to an embodiment may further include a material for a hole transport region (to be described later) other than the amine compound according to an embodiment and the amine derivative compound represented by Formula 3 in a hole transport region HTR.

The hole transport region HTR may include a compound represented by Formula H-1:

Formula H-1

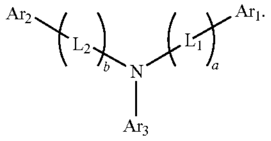

In Formula H-1, $L_1$ and $L_2$ may each independently be a direct linkage, a substituted or unsubstituted arylene group having 6 to 30 ring-forming carbon atoms, or a substituted or unsubstituted heteroarylene group having 2 to 30 ring-forming carbon atoms. a and b may each independently be an integer of 0 to 10. In some embodiments, when a or b is an integer of 2 or more, a plurality of $L_1$ and $L_2$ may each independently be a substituted or unsubstituted arylene group having 6 to 30 ring-forming carbon atoms, or a substituted or unsubstituted heteroarylene group having 2 to 30 ring-forming carbon atoms.

In Formula H-1, $Ar_1$ and $Ar_2$ may each independently be a substituted or unsubstituted aryl group having 6 to 30 ring-forming carbon atoms, or a substituted or unsubstituted heteroaryl group having 2 to 30 ring-forming carbon atoms. In some embodiments, in Formula H-1, $Ar_3$ may be a substituted or unsubstituted aryl group having 6 to 30 ring-forming carbon atoms.

The compound represented by Formula H-1 may be a monoamine compound. In some embodiments, the compound represented by Formula H-1 may be a diamine compound in which at least one of $Ar_1$ to $Ar_3$ includes an amine group as a substituent. In some embodiments, the compound represented by Formula H-1 may be a carbazole-based compound including a substituted or unsubstituted carbazole group in at least one of $Ar_1$ or $Ar_2$, or a fluorene-based compound including a substituted or unsubstituted fluorene group in at least one of $Ar^1$ or $Ar_2$.

The compound represented by Formula H-1 may be represented by any one of the compounds in Compound Group H. However, the compounds listed in Compound Group H are illustrative, and the compound represented by Formula H-1 is not limited to those represented in Compound Group H:
Compound Group H
H-1-1
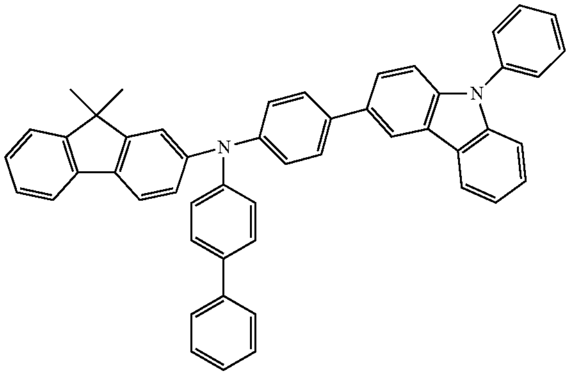
H-1-2
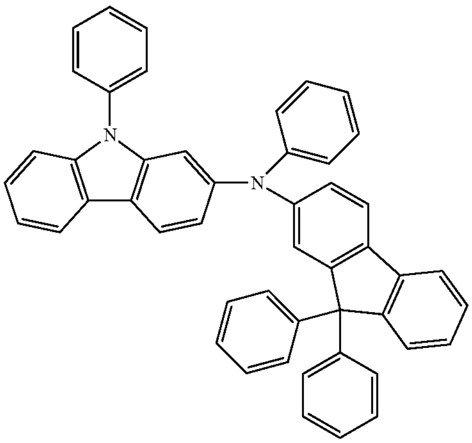
H-1-3
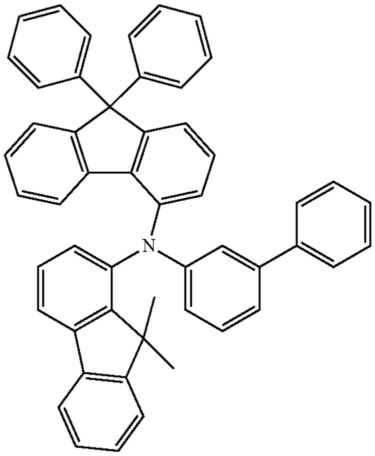
-continued
H-1-4
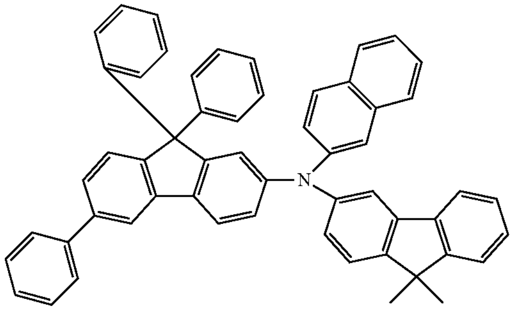
H-1-5
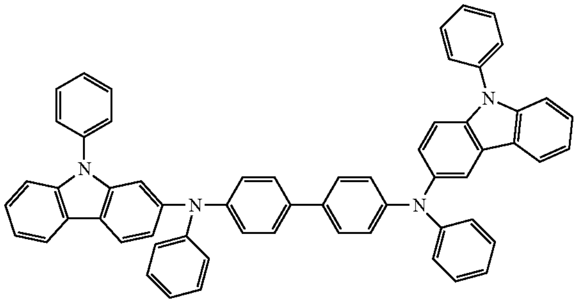
H-1-6
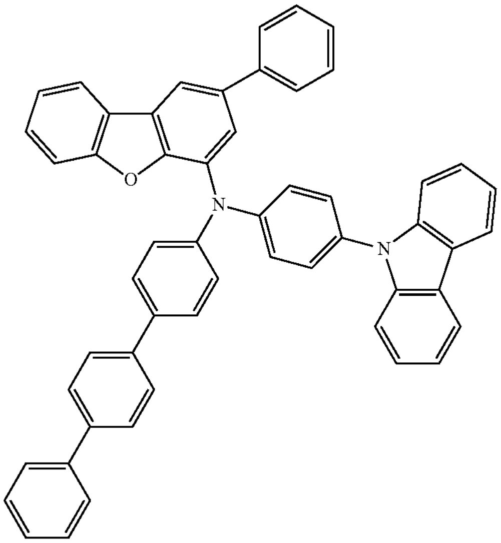

H-1-7
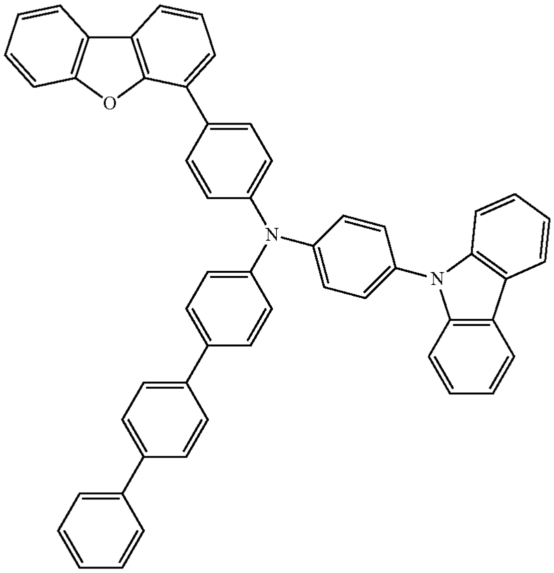
H-1-8
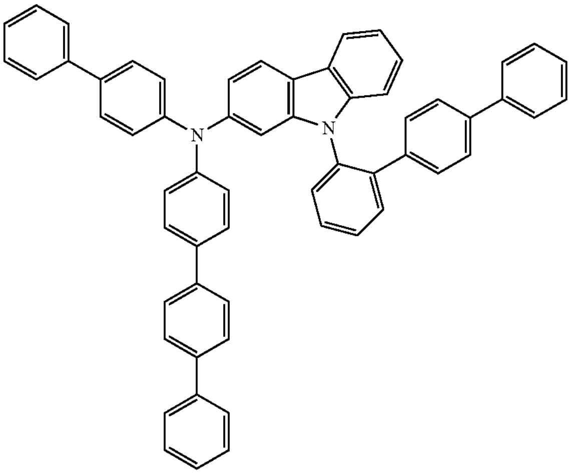
H-1-9
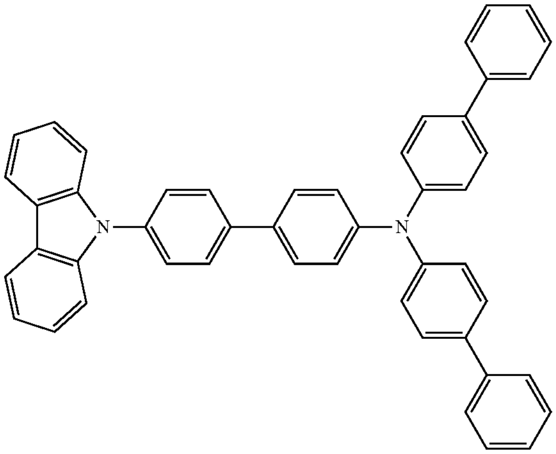
H-1-10
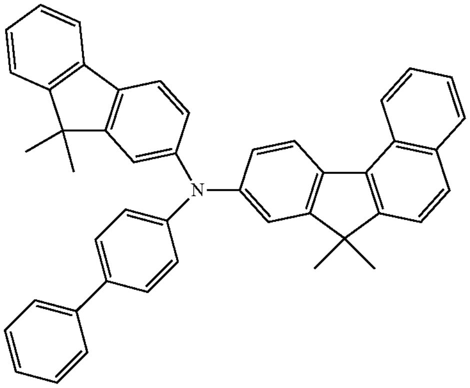
H-1-14
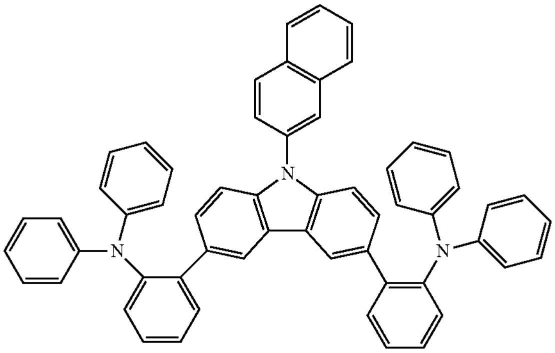
H-1-15
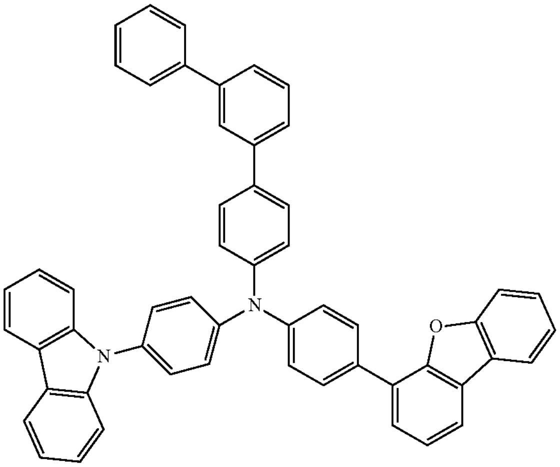

-continued

H-1-16

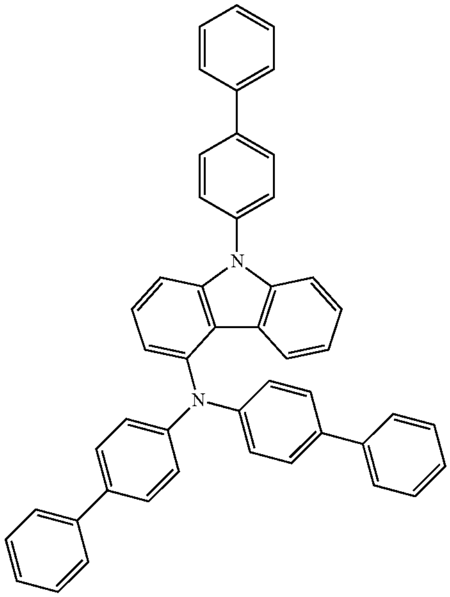

H-1-17

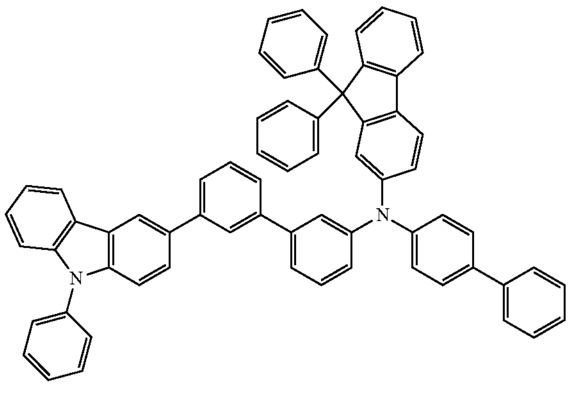

H-1-18

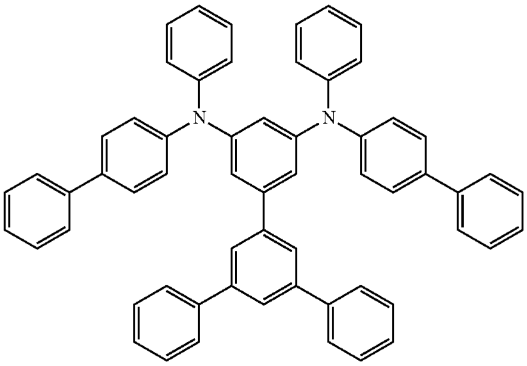

-continued

H-1-19

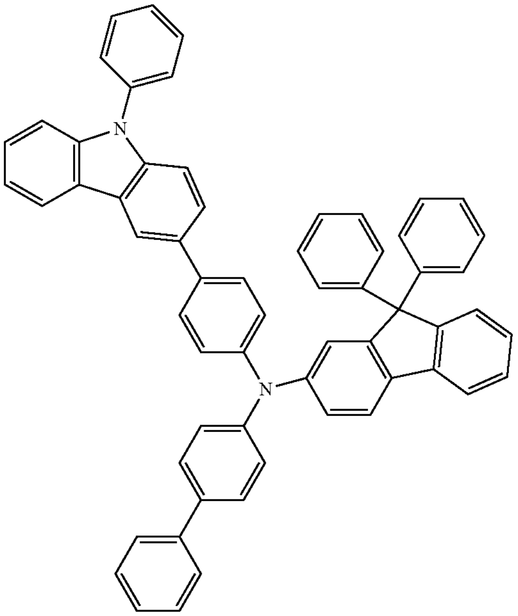

.

The hole transport region HTR may include a phthalocyanine compound (such as copper phthalocyanine), $N^1$,$N^{1'}$-([1,1'-biphenyl]-4,4'-diyl)bis($N^1$-phenyl-$N^4$,$N^4$-di-m-tolylbenzene-1,4-diamine) (DNTPD), 4,4',4"-[tris(3-methylphenyl)phenylamino] triphenylamine (m-MTDATA), 4,4'4"-tris(N,N-diphenylamino)triphenylamine (TDATA), 4,4',4"-tris[N(2-naphthyl)-N-phenylamino]-triphenylamine (2-TNATA), poly(3,4-ethylene dioxythiophene)/poly(4-styrene sulfonate) (PEDOT/PSS), polyaniline/dodecylbenzene sulfonic acid (PANI/DBSA), polyaniline/camphor sulfonicacid (PANI/CSA), polyaniline/poly(4-styrene sulfonate) (PANI/PSS), N,N'-di(naphthalen-1-yl)-N,N'-diphenyl-benzidine (NPB), triphenylamine-containing polyether ketone (TPAPEK), 4-isopropyl-4'-methyldiphenyliodonium [tetrakis(pentafluorophenyl)borate], dipyrazino[2,3-f: 2',3'-h] quinoxaline-2,3,6,7,10,11-hexacarbonitrile (HATCN), and/or the like.

The hole transport region HTR may include a carbazole-based derivative (such as N-phenyl carbazole and/or polyvinyl carbazole), a fluorene-based derivative, N,N'-bis(3-methylphenyl)-N,N'-diphenyl-[1,1-biphenyl]-4,4'-diamine (TPD), a triphenylamine-based derivative (such as 4,4',4"-tris(N-carbazolyl)triphenylamine (TCTA)), N,N'-di(naphthalen-1-yl)-N,N'-diphenyl-benzidine (NPB), 4,4'-cyclohexylidene bis[N,N-bis(4-methylphenyl)benzeneamine] (TAPC), 4,4'-bis[N,N'-(3-tolyl)amino]-3,3'-dimethylbiphenyl (HMTPD), 1,3-bis(N-carbazolyl)benzene (mCP), and/or the like.

In some embodiments, the hole transport region HTR may include 9-(4-tert-butylphenyl)-3,6-bis(triphenylsilyl)-9H-carbazole (CzSi), 9-phenyl-9H-3,9'-bicarbazole (CCP), 1,3-bis(N-carbazolyl)benzene (mCP), 1,3-bis(1,8-dimethyl-9H-carbazol-9-yl)benzene (mDCP), and/or the like.

The hole transport region HTR may include the aforementioned compounds of the hole transport region in at least one of the hole injection layer HIL, the hole transport layer HTL, or the electron blocking layer EBL.

A thickness of the hole transport region HTR may be about 100 Å to about 10000 Å, for example, about 100 Å to about 5000 Å. When the hole transport region HTR includes the hole injection layer HIL, the thickness of the hole injection layer HIL may be, for example, about 30 Å to about 1000 Å. When the hole transport region HTR includes the hole transport layer HTL, the thickness of the hole transport layer HTL may be about 30 Å to about 1000 Å. For example, when the hole transport region HTR includes the electron blocking layer EBL, the thickness of the electron blocking layer EBL may be about 10 Å to about 1000 Å. When the thicknesses of the hole transport region HTR, the hole injection layer HIL, the hole transport layer HTL, and the electron blocking layer EBL satisfy the above-described ranges, satisfactory hole transport properties may be obtained without substantial increase of a driving voltage.

The hole transport region HTR may further include a charge generating material in addition to the above-described materials in order to improve conductivity.

The charge generating material may be substantially uniformly or non-uniformly dispersed in the hole transport region HTR. The charge generating material may be, for example, a p-dopant. The p-dopant may include at least one selected from halogenated metal compounds, quinone derivatives, metal oxides, and cyano group-containing compounds, but embodiments of the present disclosure are not limited thereto. For example, the p-dopant may include a halogenated metal compound (such as CuI and/or RbI), a quinone derivative (such as tetracyanoquinodimethane (TCNQ) and/or 2,3,5,6-tetrafluoro-7,7',8,8-tetracyanoquinodimethane (F4-TCNQ)), a metal oxide (such as tungsten oxide and/or molybdenum oxide), a cyano group-containing compound (such as dipyrazino[2,3-f: 2',3'-h] quinoxaline-2,3,6,7,10,11-hexacarbonitrile (HATCN) and/or 4-[[2,3-bis[cyano-(4-cyano-2,3,5,6-tetrafluorophenyl)methylidene]cyclopropylidene]-cyanomethyl]-2,3,5,6-tetrafluorobenzonitrile(NDP9)), but embodiments of the present disclosure are not limited thereto.

As described above, the hole transport region HTR may further include at least one of the buffer layer or the electron blocking layer EBL in addition to the hole injection layer HIL and the hole transport layer HTL. The buffer layer may compensate for an optical resonance distance of the wavelength of light emitted from the emission layer EML to thereby increase the light emission efficiency of the device. Materials that may be included in the hole transport region HTR may be utilized as materials included in the buffer layer. The electron blocking layer EBL is a layer playing the role of preventing or reducing the electron injection from the electron transport region ETR to the hole transport region HTR.

The emission layer EML is provided on the hole transport region HTR. The emission layer EML may have a thickness of, for example about 100 Å to about 1000 Å, or about 100 Å to about 300 Å. The emission layer EML may have a single layer formed of a single material, a single layer formed of a plurality of different materials, or a multilayer structure having a plurality of layers formed of a plurality of different materials.

In the light-emitting element ED, the emission layer EML may include an anthracene derivative, a pyrene derivative, a fluoranthene derivative, a chrysene derivative, a dihydrobenzanthracene derivative, and/or a triphenylene derivative. For example, the emission layer EML may include an anthracene derivative and/or a pyrene derivative.

In the light-emitting element ED according to an embodiment illustrated in FIGS. 3 to 7, the emission layer EML may include a host and a dopant, and the emission layer EML may include the compound represented by Formula E-1. The compound represented by Formula E-1 may be utilized as a fluorescent host material.

Formula E-1

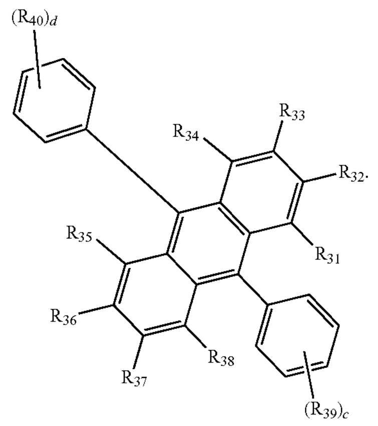

In Formula E-1, $R_{31}$ to $R_{40}$ may each independently be a hydrogen atom, a deuterium atom, a halogen atom, a substituted or unsubstituted silyl group, a substituted or unsubstituted thio group, a substituted or unsubstituted oxy group, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring. In some embodiments, $R_{31}$ to $R_{40}$ may be bonded to an adjacent group to form a saturated hydrocarbon ring, an unsaturated hydrocarbon ring, a saturated hetero ring, or an unsaturated hetero ring.

In Formula E-1, "c" and "d" may each independently be an integer of 0 to 5.

The compound represented by Formula E-1 may be represented by any one among Compound E1 to Compound E19.

E1

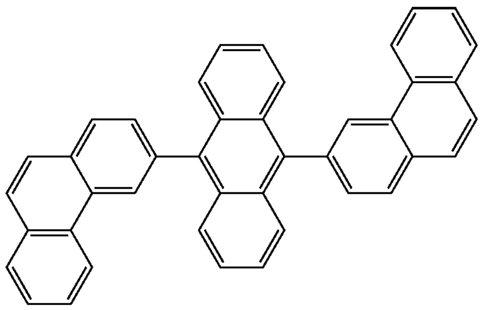

E2

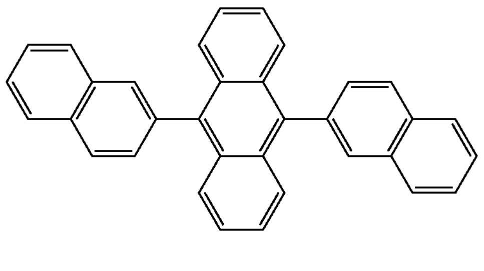

-continued
E3
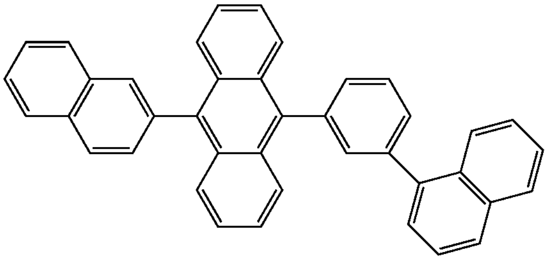
E4
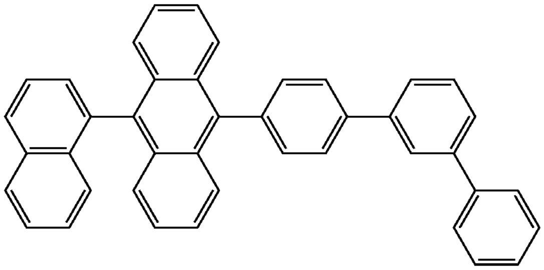
E5
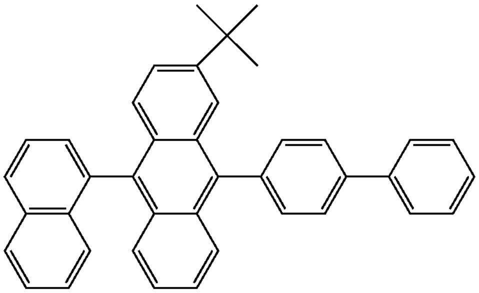
E6
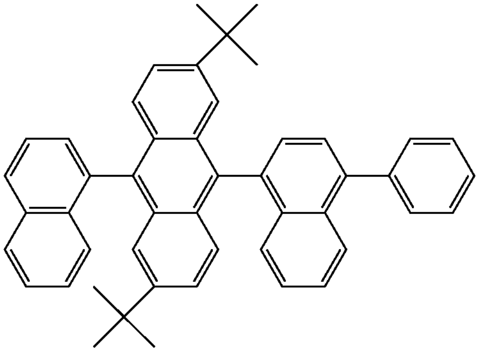
E7
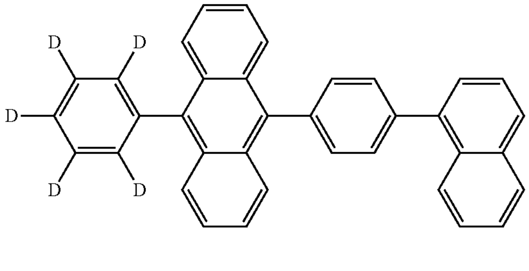
-continued
E8
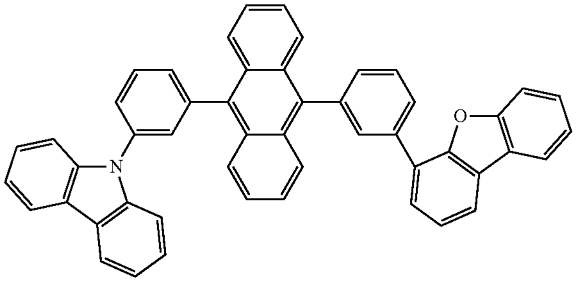
E9
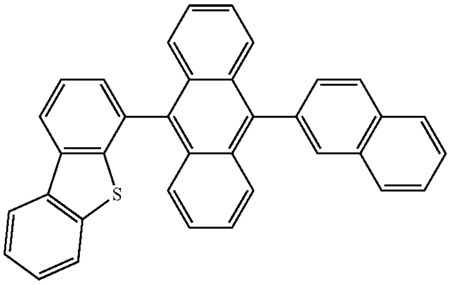
E10
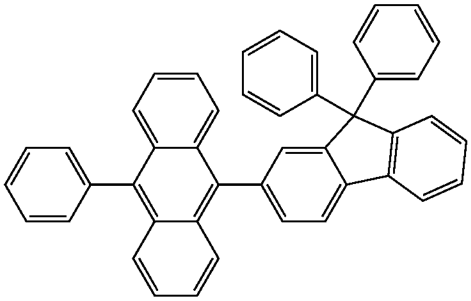
E11
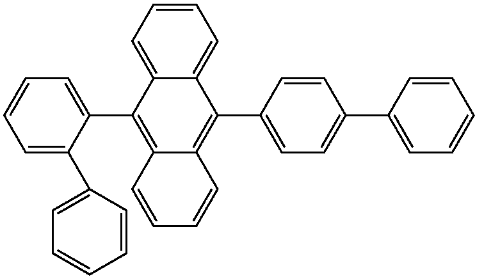
E12
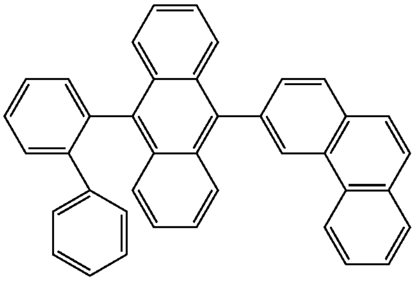

-continued
E13
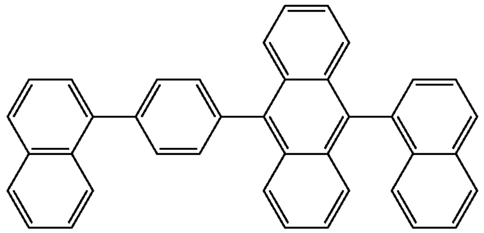
E14
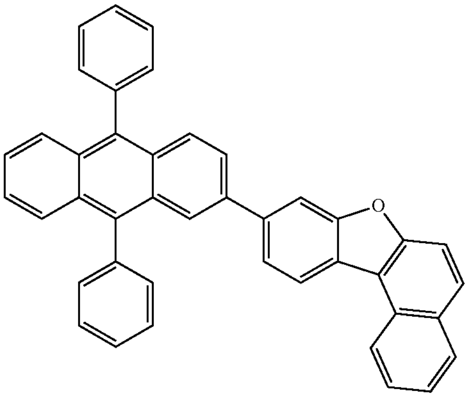
E15
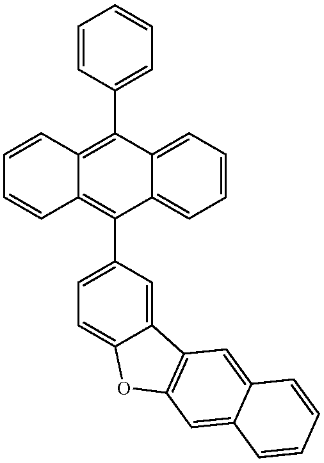
E16
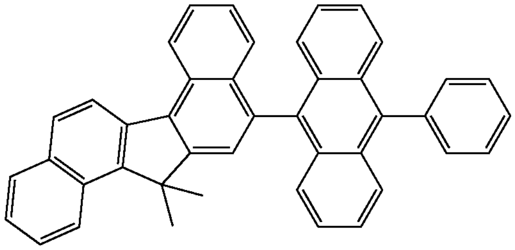
-continued
E17
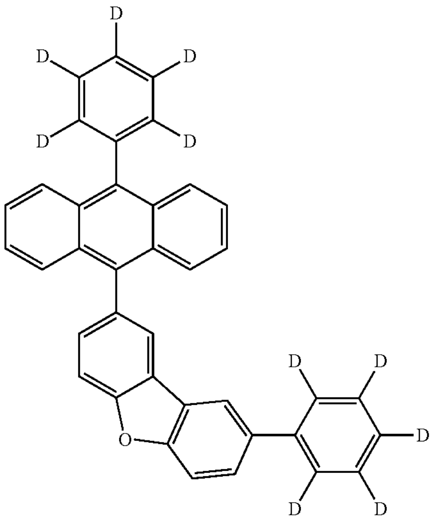
E18
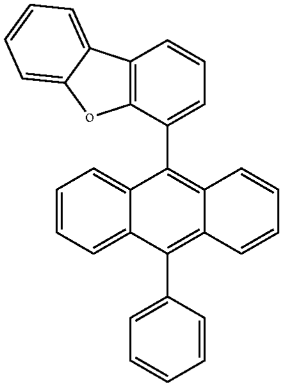
E19
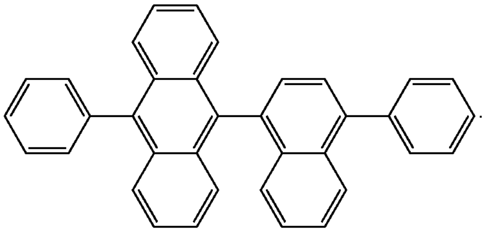
In an embodiment, the emission layer EML may include the compound represented by Formula E-2a or Formula E-2b. The compound represented by Formula E-2a or Formula E-2b may be utilized as a phosphorescent host material.

Formula E-2a

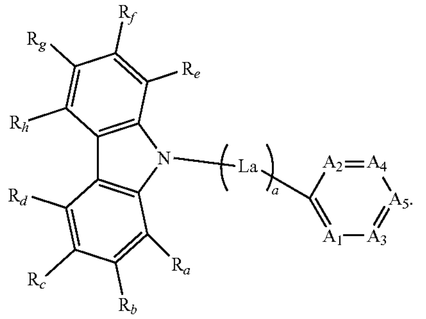

In Formula E-2a, a may be an integer of 0 to 10, and $L_a$ may each independently be a substituted or unsubstituted arylene group having 6 to 30 ring-forming carbon atoms, or a substituted or unsubstituted heteroarylene group having 2 to 30 ring-forming carbon atoms. In some embodiments, when a is an integer of 2 or more, a plurality of $L_a$ may each independently be a substituted or unsubstituted arylene group having 6 to 30 ring-forming carbon atoms, or a substituted or unsubstituted heteroarylene group having 2 to 30 ring-forming carbon atoms.

In some embodiments, in Formula E-2a, $A_1$ to $A_5$ may each independently be N or $CR_i$. $R_a$ to $R_i$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring. In some embodiments, $R_a$ to $R_i$ may bonded to an adjacent group to form a hydrocarbon ring or a hetero ring including N, O, S, and/or the like as a ring-forming atom.

In some embodiments, in Formula E-2a, two or three selected from $A_1$ to $A_5$ may be N, and the remainder may be $CR_1$.

Formula E-2b $$(Cbz1)\!-\!(L_b)_b\!-\!(Cbz2).$$

In Formula E-2b, Cbz1 and Cbz2 may each independently be an unsubstituted carbazole group, or a carbazole group substituted with a aryl group having 6 to 30 ring-forming carbon atoms. $L_b$ may be a direct linkage, a substituted or unsubstituted arylene group having 6 to 30 ring-forming carbon atoms, or a substituted or unsubstituted heteroarylene group having 2 to 30 ring-forming carbon atoms. When "b" is an integer of 0 to 10, and b is an integer of 2 or more, a plurality of $L_b$ may each independently be a substituted or unsubstituted arylene group having 6 to 30 ring-forming carbon atoms, or a substituted or unsubstituted heteroarylene group having 2 to 30 ring-forming carbon atoms.

The compound represented by Formula E-2a or Formula E-2b may be represented by any one of the compounds in Compound Group E-2. However, the compounds listed in Compound Group E-2 are illustrative, and the compound represented by Formula E-2a or Formula E-2b is not limited to those represented in Compound Group E-2:

Compound Group E-2

E-2-1

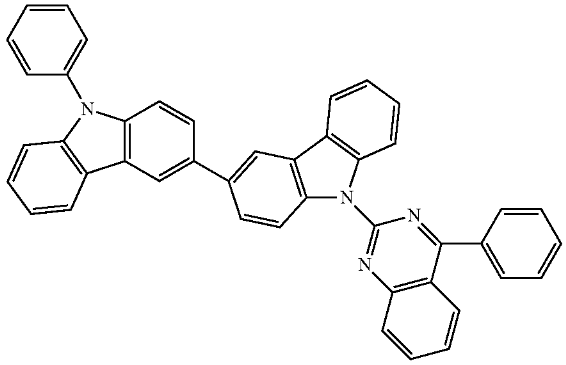

E-2-2

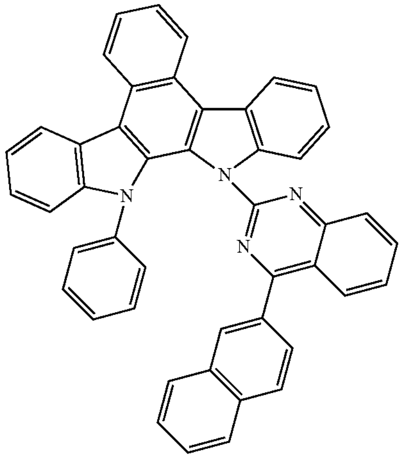

E-2-3

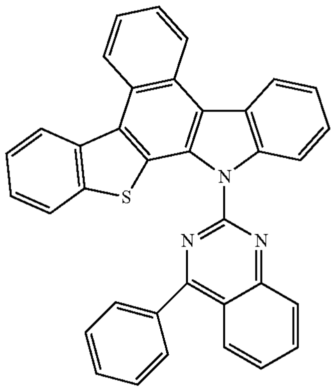

-continued
E-2-4
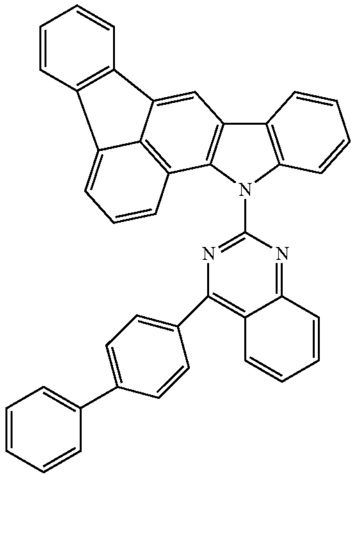
E-2-5
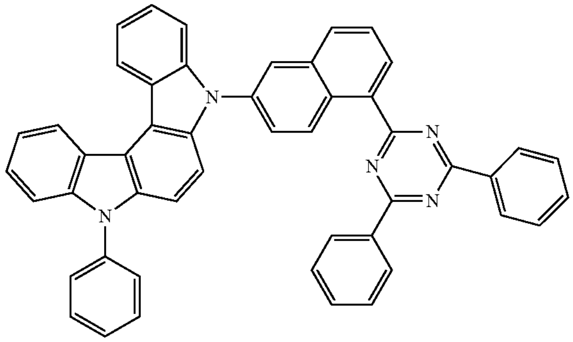
E-2-6
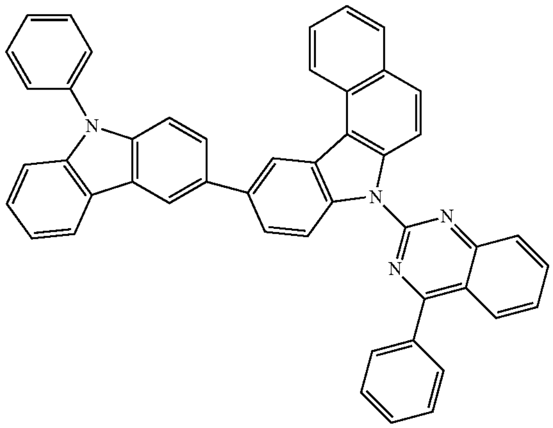
-continued
E-2-7
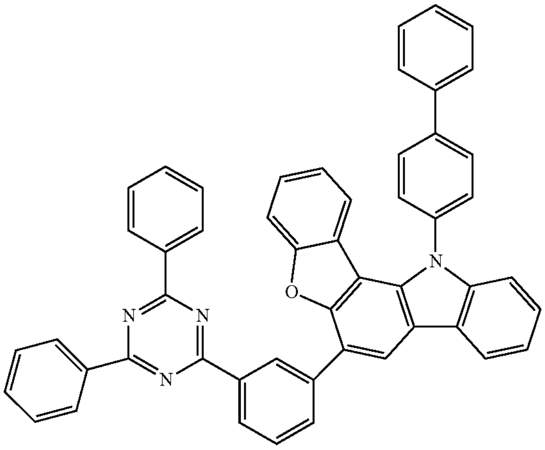
E-2-8
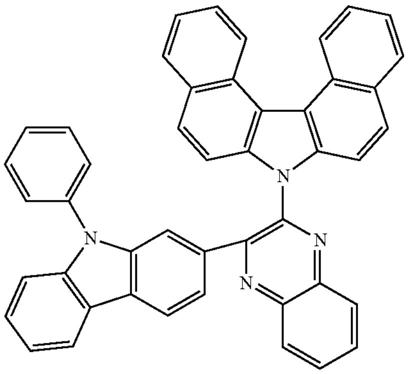
E-2-9
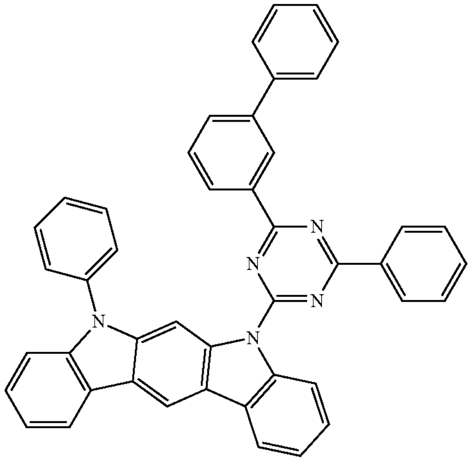

-continued
E-2-10
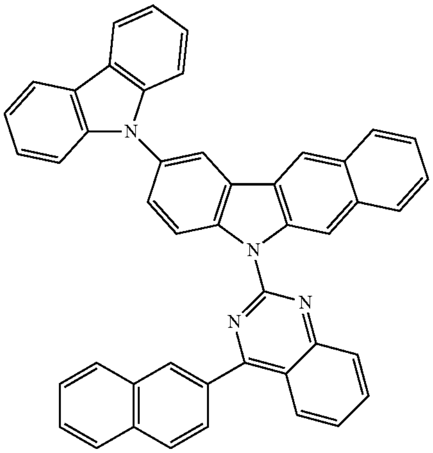
E-2-11
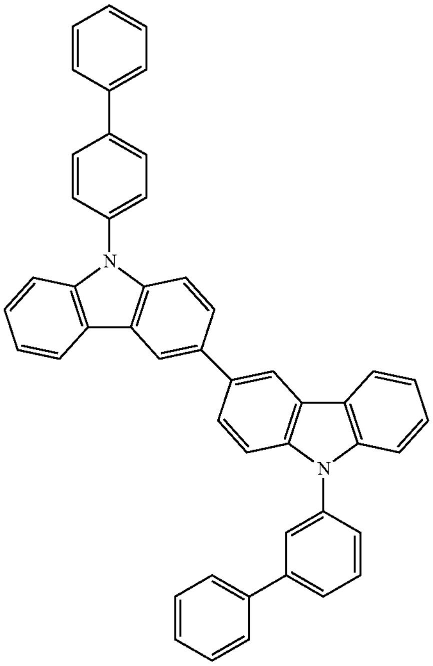
E-2-12
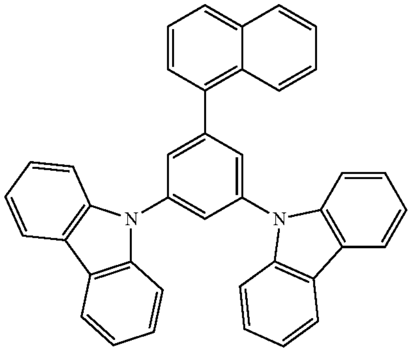
-continued
E-2-13
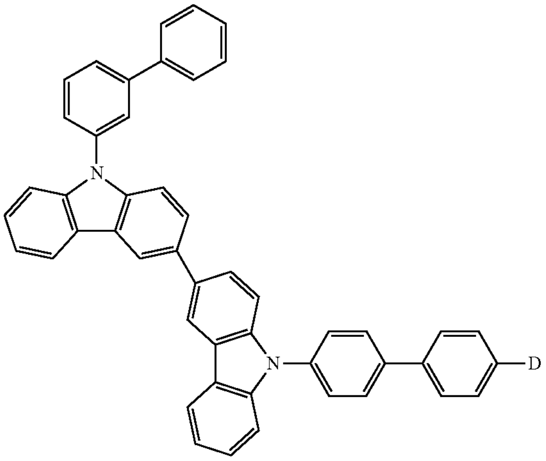
E-2-14
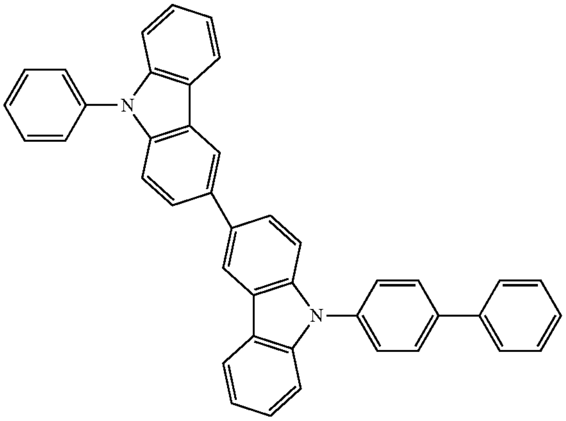
E-2-15
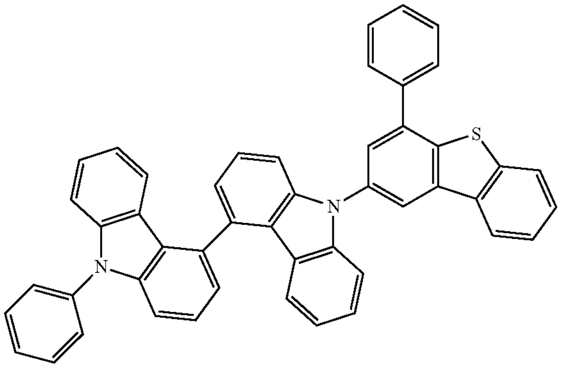

-continued
E-2-16
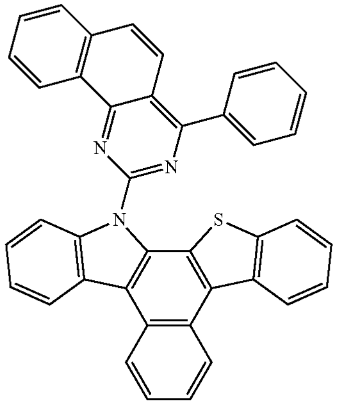
E-2-17
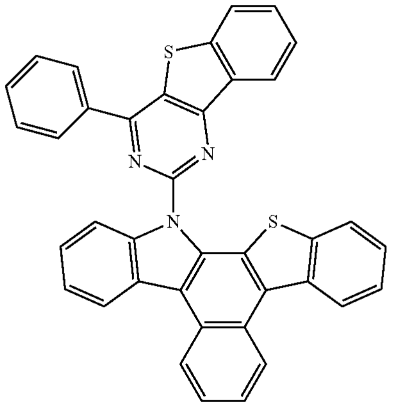
E-2-18
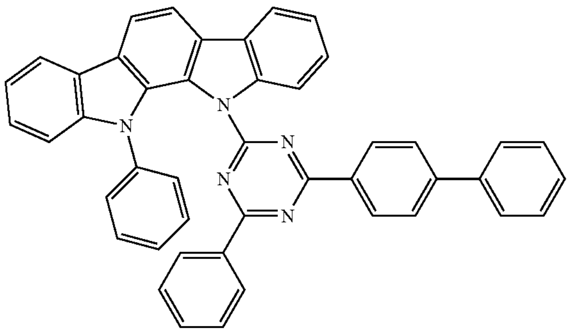
E-2-19
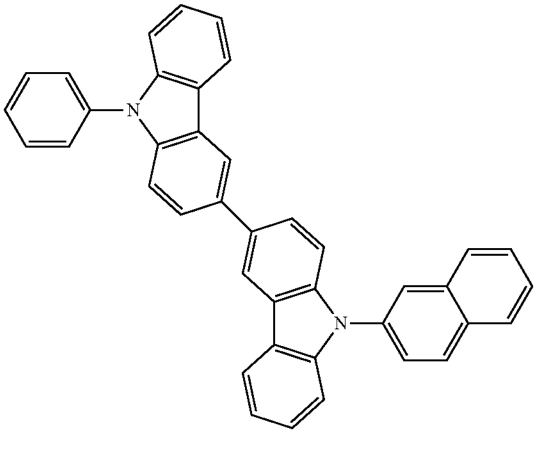
-continued
E-2-20
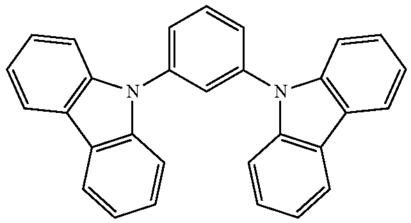
E-2-21
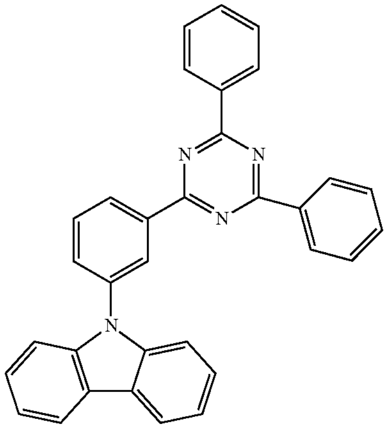
E-2-22
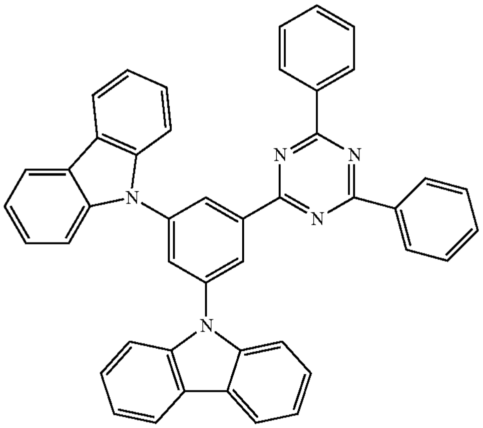
E-2-23
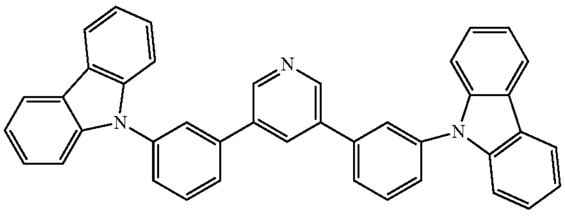

-continued

E-2-24

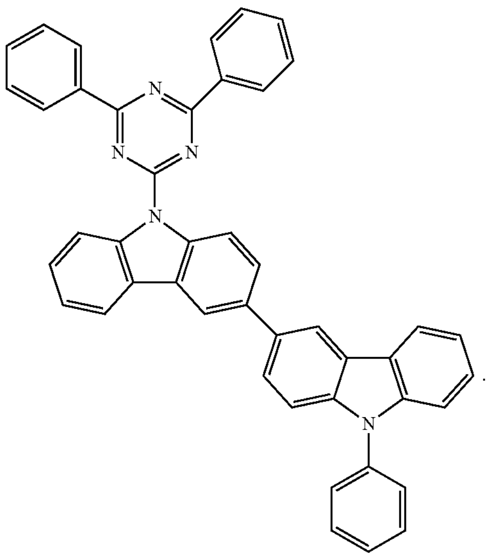

The emission layer EML may further include any suitable material in the art as a host material. For example, the emission layer EML may include at least one selected from bis[2-(diphenylphosphino)phenyl] ether oxide (DPEPO), 4,4'-bis(N-carbazolyl)-1,1'-biphenyl (CBP), 1,3-bis(carbazol-9-yl)benzene (mCP), 2,8-bis(diphenylphosphoryl) dibenzo[b,d]furan (PPF), 4,4',4"-tris(carbazol-9-yl)-triphenylamine (TCTA), and 1,3,5-tris(1-phenyl-1H-benzo[d] imidazole-2-yl)benzene (TPBi) as the host material. However, embodiments of the present disclosure are not limited thereto, and for example, tris(8-hydroxyquinolino) aluminum ($Alq_3$), 9,10-di(naphthalene-2-yl)anthracene (ADN), 2-tert-butyl-9,10-di(naphth-2-yl)anthracene (TBADN), distyrylarylene (DSA), 4,4'-bis(9-carbazolyl)-2, 2'-dimethyl-biphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), and/or the like may be utilized as the host material.

The emission layer EML may include the compound represented by Formula M-a or Formula M-b. The compound represented by Formula M-a or Formula M-b may be utilized as a phosphorescent dopant material.

Formula M-a

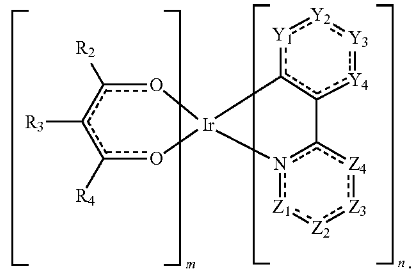

In Formula M-a, $Y_1$ to $Y_4$, and $Z_1$ to $Z_4$ may each independently be $CR_1$ or N, and $R_1$ to $R_4$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring. In Formula M-a, "m" may be 0 or 1, and "n" may be 2 or 3. In Formula M-a, when "m" is 0, "n" may be 3, and when "m" is 1, "n" may be 2.

The compound represented by Formula M-a may be utilized as a phosphorescent dopant.

The compound represented by Formula M-a may be represented by any one selected from Compounds M-a1 to M-a25. However, Compounds M-a1 to M-a25 are illustrative, and the compound represented by Formula M-a is not limited to those represented by Compounds M-a1 to M-a25.

M-a1

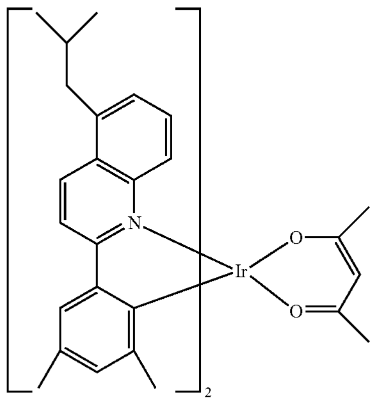

M-a2

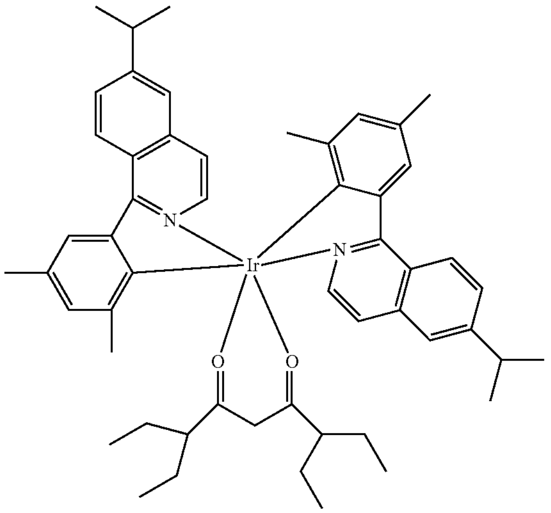

-continued
M-a3
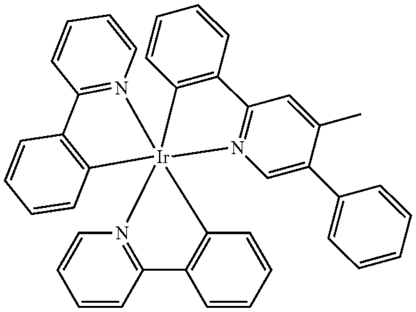
M-a4
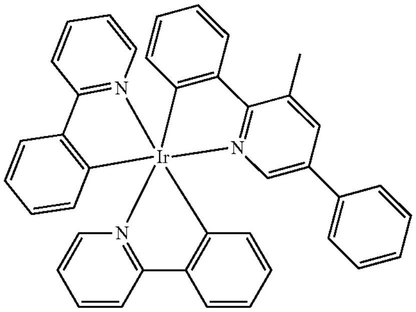
M-a5
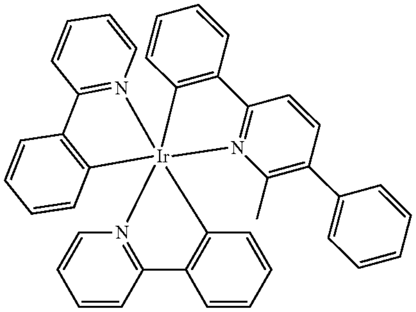
M-a6
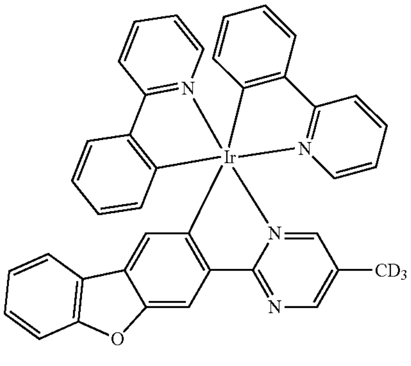
-continued
M-a7
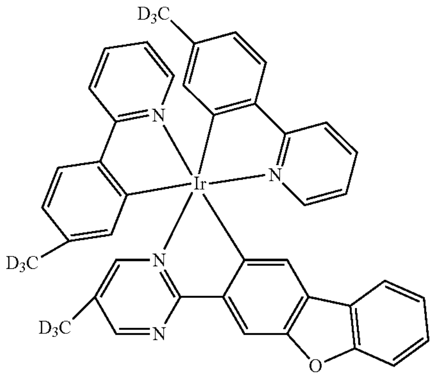
M-a8
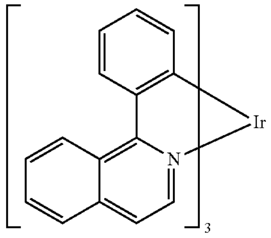
M-a9
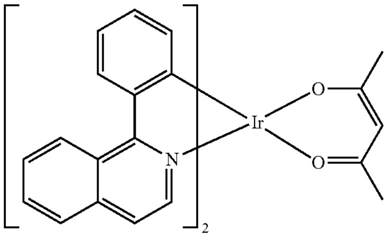
M-a10
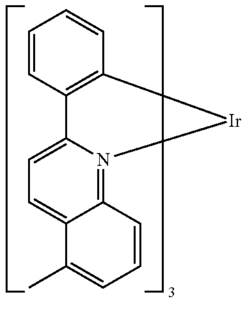
M-a11
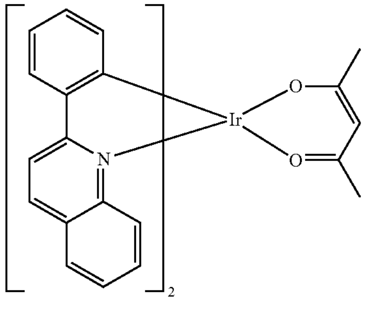

-continued
M-a12
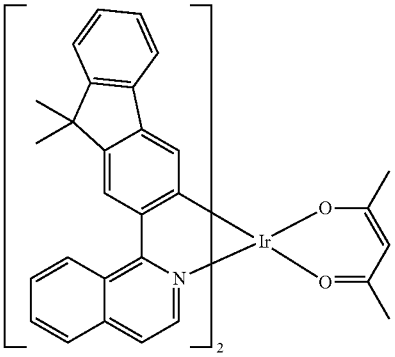
M-a13
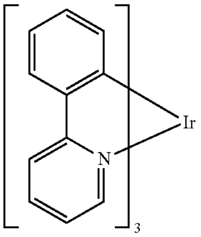
M-a14
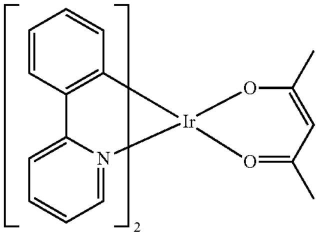
M-a15
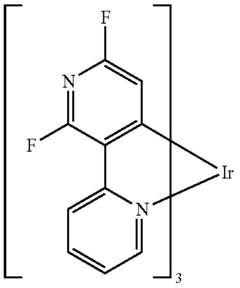
M-a16
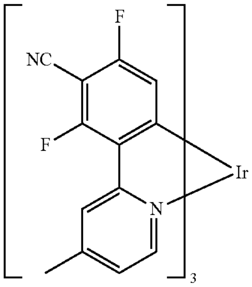
-continued
M-a17
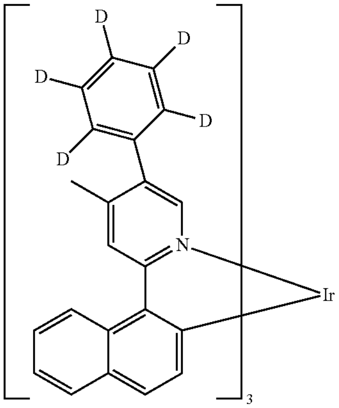
M-a18
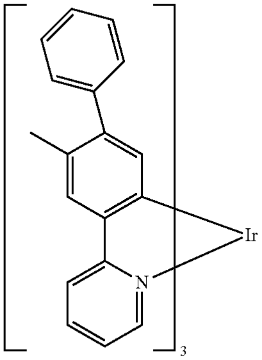
M-a19
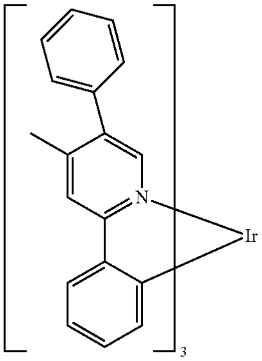
M-a20
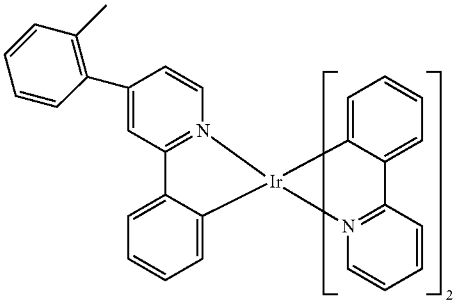

-continued

M-a21

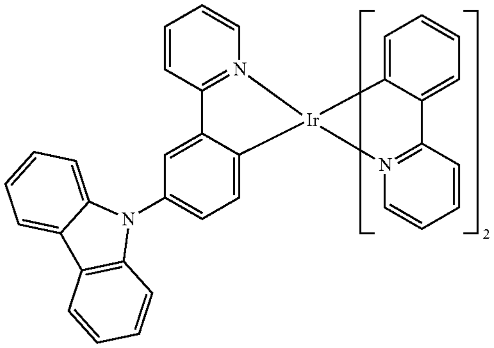

M-a22

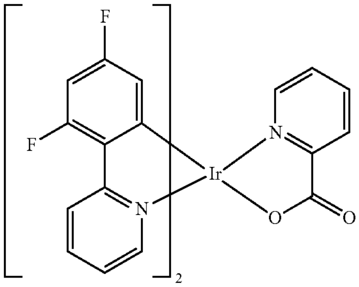

M-a23

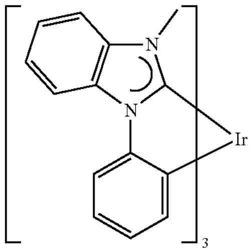

M-a24

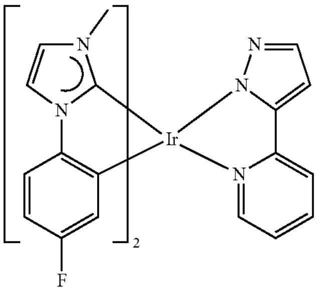

M-a25

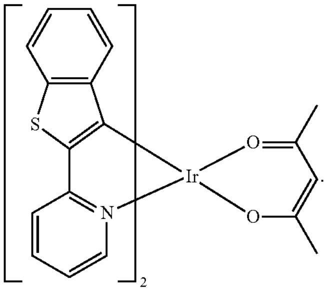

Compound M-a1 and Compound M-a2 may be utilized as a red dopant material, and Compounds M-a3 to M-a7 may be utilized as a green dopant material.

Formula M-b

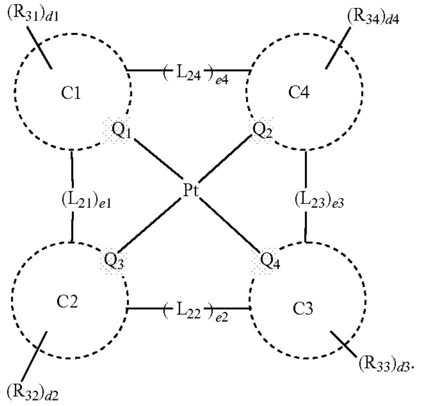

In Formula M-b, $Q_1$ to $Q_4$ may each independently be C or N, and C1 to C4 may each independently be a substituted or unsubstituted hydrocarbon ring having 5 to 30 ring-forming carbon atoms, or a substituted or unsubstituted heterocycle having 2 to 30 ring-forming carbon atoms. $L_{21}$ to $L_{24}$ may each independently be a direct linkage,

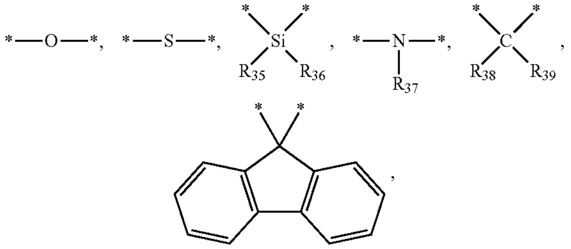

a substituted or unsubstituted divalent alkyl group having 1 to 20 carbon atoms, a substituted or unsubstituted arylene group having 6 to 30 ring-forming carbon atoms, or a substituted or unsubstituted heteroarylene group having 2 to 30 ring-forming carbon atoms, and e1 to e4 may each independently be 0 or 1. $R_{31}$ to $R_{39}$ may each independently be a hydrogen atom, a deuterium atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring, and dl to d4 may each independently be an integer of 0 to 4.

The compound represented by Formula M-b may be utilized as a blue phosphorescent dopant or a green phosphorescent dopant.

The compound represented by Formula M-b may be represented by any one of the compounds below. However, the compounds are illustrative, and the compound represented by Formula M-b is not limited to those shown below:

-continued
M-b-1
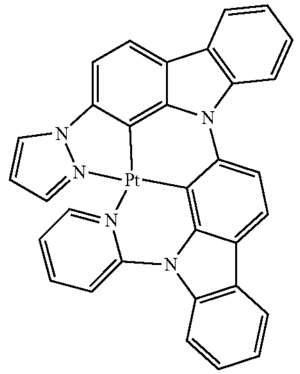
M-b-2
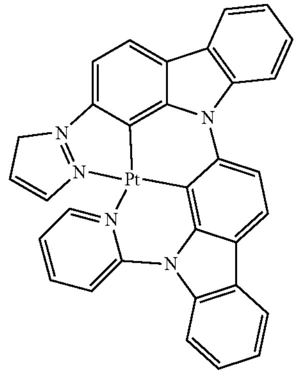
M-b-3
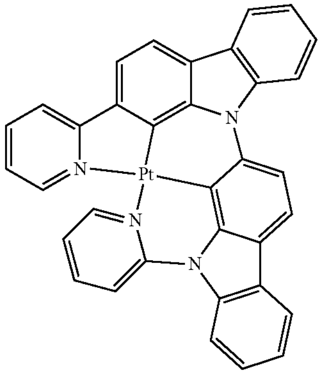
M-b-4
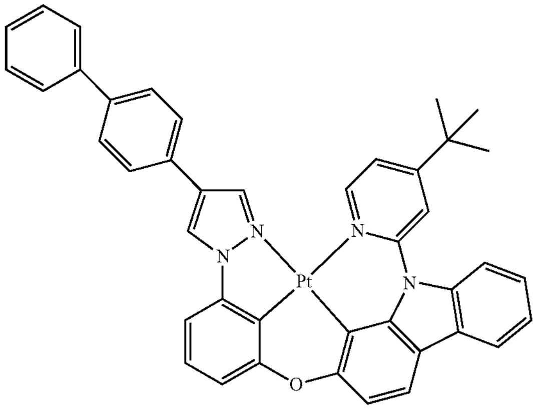
M-b-5
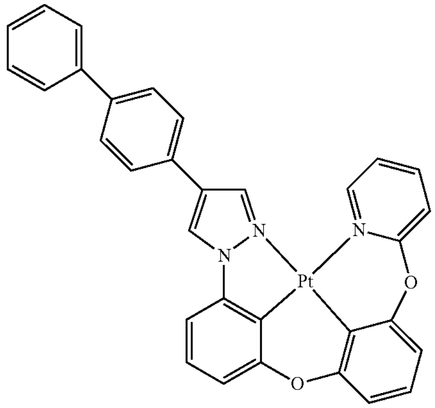
M-b-6
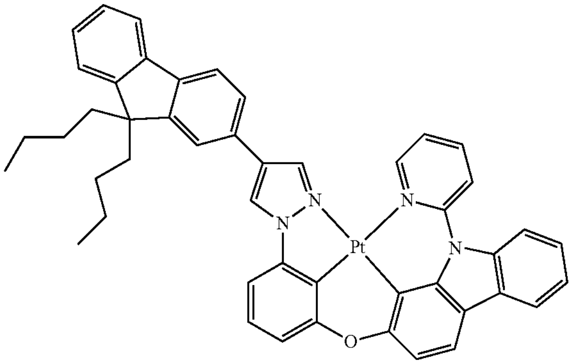
M-b-7
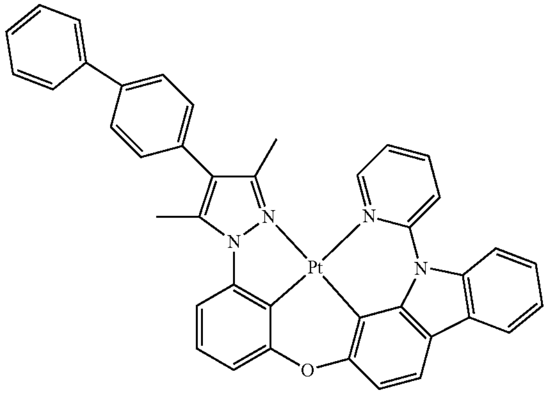
M-b-8
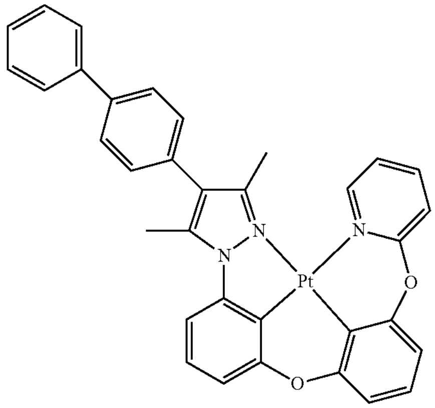

-continued

M-b-9

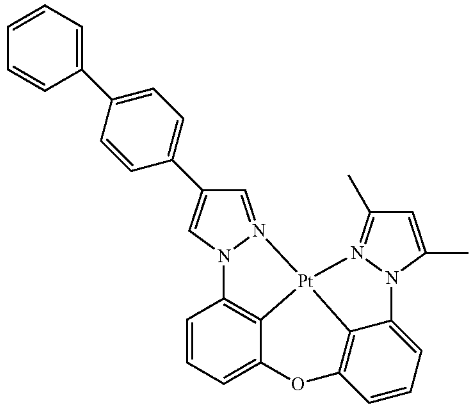

M-b-10

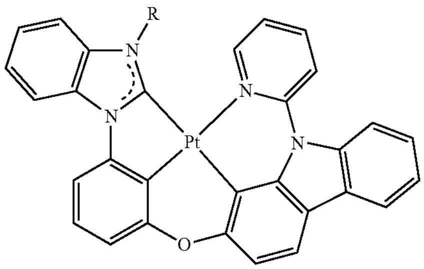

M-b-11

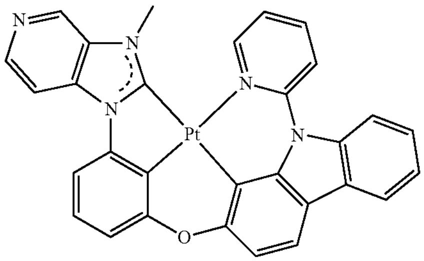

M-b-12

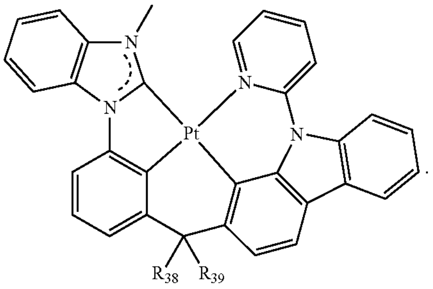

In the above compounds, R, $R_{38}$, and $R_{39}$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

The emission layer EML may include the compound represented by any one among Formula F-a to Formula F-c. The compound represented by Formula F-a to Formula F-c may be utilized as a fluorescent dopant material.

Formula F-a

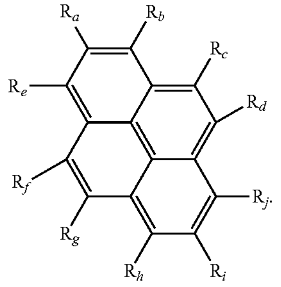

In Formula F-a, two selected from $R_a$ to $R_j$ may each independently be substituted with *—$NAr_1Ar_2$. The remainder of $R_a$ to $R_j$ that are not substituted with *—$NAr_1Ar_2$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. In *—$NAr_1Ar_2$, $Ar_1$ and $Ar_2$ may each independently be a substituted or unsubstituted aryl group having 6 to 30 ring-forming carbon atoms, or a substituted or unsubstituted heteroaryl group having 2 to 30 ring-forming carbon atoms. For example, at least one of $Ar_1$ or $Ar_2$ may be a heteroaryl group including O or S as a ring-forming atom.

Formula F-b

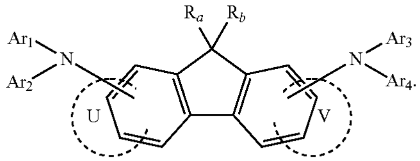

In the Formula F-b, $R_a$ and $R_b$ may each independently be a hydrogen atom, a deuterium atom, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring. $Ar_1$ to $Ar_4$ may each independently be a substituted or unsubstituted aryl group having 6 to 30 ring-forming carbon atoms, or a substituted or unsubstituted heteroaryl group having 2 to 30 ring-forming carbon atoms.

In Formula F-b, U and V may each independently be a substituted or unsubstituted hydrocarbon ring having 5 to 30 ring-forming carbon atoms, or a substituted or unsubstituted heterocycle having 2 to 30 ring-forming carbon atoms.

In Formula F-b, the number of rings represented by U and V may each independently be 0 or 1. For example, in Formula F-b, when the number of U or V is 1, one condensed ring is formed at the portion indicated by U or V, and when the number of U or V is 0, the ring indicated as U or V does not exist. For example, when the number of U is 0 and the number of V is 1, or the number of U is 1 and the number of V is 0, the condensed ring having a fluorene core of Formula F-b may be a tetracyclic compound. When the numbers of U and V are both (e.g., simultaneously) 0, the condensed ring of Formula F-b may be a tricyclic compound. Further, when the number of U and V are both (e.g., simultaneously) 1, the condensed ring having a fluorene core of Formula F-b may be a pentacyclic compound.

Formula F-c

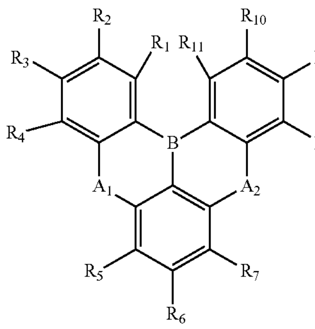

In Formula F-c, $A_1$ and $A_2$ may each independently be O, S, Se, or $NR_m$, and $R_m$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. $R_1$ to $R_{11}$ may each independently be a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring.

In Formula F-c, $A_1$ and $A_2$ may each independently be bonded to substituents of adjacent rings to form a condensed ring. For example, when $A_1$ and $A_2$ are each independently $NR_m$, $A_1$ may be bonded to $R_4$ or $R_5$ to form a ring. In some embodiments, $A_2$ may be bonded to $R_7$ or $R_8$ to form a ring.

In an embodiment, the emission layer EML may include, as a suitable dopant material, a styryl derivative (for example, 1,4-bis[2-(3-N-ethylcarbazolyl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalen-2-yl)vinyl)phenyl)-N-phenylbenzenamine (N-BDAVBi)), 4,4'-bis[2-(4-(N,N-diphenylamino)phenyl)vinyl]biphenyl (DPAVBi), perylene and/or derivatives thereof (for example, 2,5,8,11-tetra-t-butylperylene (TBP)), pyrene and/or derivatives thereof (for example, 1,1-dipyrene,1,4-dipyrenylbenzene,1,4-bis(N,N-diphenylamino)pyrene), and/or the like.

The emission layer EML may include any suitable phosphorescent dopant material. For example, a metal complex including iridium (Ir), platinum (Pt), osmium (Os), gold (Au), titanium (Ti), zirconium (Zr), hafnium (Hf), europium (Eu), terbium (Tb), or thulium (Tm) may be utilized as a phosphorescent dopant. For example, iridium(III) bis(4,6-difluorophenylpyridinato-N,C2'-picolinate) (Flrpic), bis(2,4-difluorophenylpyridinato)-tetrakis(1-pyrazolyl)borate (Fir6), and/or platinum octaethyl porphyrin (PtOEP) may be utilized as a phosphorescent dopant. However, embodiments of the present disclosure are not limited thereto.

The emission layer EML may include a quantum dot material. The core of the quantum dot may be selected from a Group II-VI compound, a Group III-VI compound, a Group compound, a Group III-V compound, a Group III-II-V compound, a Group III-V compound, a Group IV-VI compound, a Group IV element, a Group IV compound, and a combination thereof.

A Group II-VI compound may be selected from the group consisting of a binary compound selected from the group consisting of CdSe, CdTe, CdS, ZnS, ZnSe, ZnTe, ZnO, HgS, HgSe, HgTe, MgSe, MgS, and a mixture thereof; a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof; and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and a mixture thereof.

A Group III-VI compound may include a binary compound (such as $In_2S_3$ and/or $In_2Se_3$), a ternary compound (such as $InGaS_3$ and $InGaSe_3$), or any combination thereof.

A Group compound may be selected from a ternary compound selected from the group consisting of AgInS, $AgInS_2$, CuInS, $CuInS_2$, $AgGaS_2$, $CuGaS_2$ $CuGaO_2$, $AgGaO_2$, $AgAlO_2$, and a mixture thereof, and a quaternary compound (such as $AgInGaS_2$ and/or $CuInGaS_2$).

A Group III-V compound may be selected from the group consisting of a binary compound selected from the group consisting of GaN, GaP, GaAs, GaSb, AlN, AlP, AlAs, AlSb, InN, InP, InAs, InSb, and a mixture thereof; a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and a mixture thereof; and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and a mixture thereof. In some embodiments, the Group III-V compound may further include a Group II metal. For example, InZnP and/or the like may be selected as a Group III-II-V compound.

A Group IV-VI compound may be selected from the group consisting of a binary compound selected from the group consisting of SnS, SnSe, SnTe, PbS, PbSe, PbTe, and a mixture thereof; a ternary compound selected from the group consisting of SnSeS, SnSeTe, SnSTe, PbSeS, PbSeTe, PbSTe, SnPbS, SnPbSe, SnPbTe, and a mixture thereof; and a quaternary compound selected from the group consisting of SnPbSSe, SnPbSeTe, SnPbSTe, and a mixture thereof. Group IV elements may be selected from the group consisting of Si, Ge, and a mixture thereof. Group IV compounds may be a binary compound selected from the group consisting of SiC, SiGe, and a mixture thereof.

In this case, the binary compound, the ternary compound, and/or the quaternary compound may be present in the particle at a substantially uniform concentration (e.g., distribution), or may be present in the same particle with varying or partially different concentration distributions. In some embodiments, the quantum dot may have a core/shell structure, in which one quantum dot surrounds another quantum dot. The core/shell structure may have (e.g., may form) a concentration gradient, for example, in which a concentration of an element or compound present in the shell gradually decreases toward the core.

In some examples, the quantum dot may have a core-shell structure including a core that includes the aforementioned nanocrystal and a shell around (e.g., surrounding) the core. The shell of the quantum dot may serve as a protective layer for maintaining semiconductor characteristics by preventing or reducing chemical modification of the core, and/or may serve as a charging layer for imparting electrophoretic characteristics to the quantum dot. The shell may be a single layer or may have multiple layers. Examples of material in the shell of the quantum dot may include a metal or non-metal oxide, a semiconductor compound, or a combination thereof.

For example, the metal or non-metal oxide may be illustrated as a binary compound (such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and/or NiO), or a ternary compound (such as $MgAl_2O_4$, $CoFe_2O_4$, $NiFe_2O_4$, and/or $CoMn_2O_4$), but embodiments of the present disclosure are not limited thereto.

In some embodiments, the semiconductor compound may be CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, and/or the like, but embodiments of the present disclosure are not limited thereto.

The quantum dot may have a full width of half maximum (FWHM) of an emission wavelength spectrum of about 45 nm or less, for example about 40 nm or less, or about 30 nm or less, and color purity and/or color gamut may be improved in this range. Because light emitted through a quantum dot is emitted in all directions, a wide viewing angle may be improved.

In some embodiments, the quantum dot has any suitable shape in the art, and for example, spherical, pyramidal, multi-arm, or cubic nanoparticles, nanotubes, nanowires, nanofibers, plate-shaped nanoparticles, and/or the like may be utilized.

The quantum dot may control the color of emitted light according to the particle size, and thus, the quantum dots may have one or more suitable light-emitting colors (such as blue, red, green, and/or the like).

In the light-emitting elements ED according to an embodiment illustrated in FIGS. 3 to 7, the electron transport region ETR is provided on the emission layer EML. The electron transport region ETR may include at least one of the hole blocking layer HBL, the electron transport layer ETL, or the electron injection layer EIL, but embodiments of the present disclosure are not limited thereto.

The electron transport region ETR may have a single layer structure formed of a single material, a single layer structure formed of a plurality of different materials, or a multilayer structure having a plurality of layers formed of a plurality of different materials.

For example, the electron transport region ETR may have a structure of a single layer of an electron injection layer EIL or an electron transport layer ETL, and may have a structure of a single layer formed of an electron injection material and an electron transport material. Further, the electron transport region ETR may have a single layer structure formed of a plurality of different materials, or a structure in which an electron transport layer ETL/electron injection layer EIL, or a hole blocking layer HBL/electron transport layer ETL/electron injection layer EIL are stacked in order from the emission layer EML, but embodiments of the present disclosure are not limited thereto. A thickness of the electron transport region ETR may be, for example, about 1000 Å to about 1500 Å.

The electron transport region ETR may be formed by utilizing one or more suitable methods (such as a vacuum deposition method, a spin coating method, a cast method, a Langmuir-Blodgett (LB) method, an inkjet printing method, a laser printing method, and/or a laser induced thermal imaging (LITI) method).

The electron transport region ETR may include the compound represented by Formula ET-1.

Formula ET-1

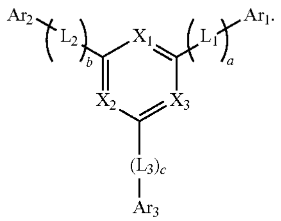

In Formula ET-1, at least one selected from $X_1$ to $X_3$ is N, and the remainder are $CR_a$. $R_a$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. $Ar_1$ to $Ar_3$ may each independently be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula ET-1, a to c may each independently be an integer of 0 to 10. In Formula ET-1, $L_1$ to $L_3$ may each independently be a direct linkage, a substituted or unsubstituted arylene group having 6 to 30 ring-forming carbon atoms, or a substituted or unsubstituted heteroarylene group having 2 to 30 ring-forming carbon atoms. In some embodiments, when a to c are integer of 2 or more, $L_1$ to $L_3$ may respectively and each independently be a substituted or unsubstituted arylene group having 6 to 30 ring-forming carbon atoms, or a substituted or unsubstituted heteroarylene group having 2 to 30 ring-forming carbon atoms.

The electron transport region ETR may include an anthracene-based compound. However, embodiments of the present disclosure are not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzimidazol-1-yl)phenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), beryllium bis(benzoquinolin-10-olate) ($Bebq_2$), 9,10-di(naphthalen-2-yl)anthracene (ADN), 1,3-bis[3,5-di(pyridin-3-yl)phenyl]benzene (BmPyPhB), or a mixture thereof.

In some embodiments, the electron transport region ETR may include a halogenated metal (such as LiF, NaCl, CsF, RbCl, RbI, CuI, and/or KI), a lanthanide metal (such as Yb), and a co-deposited material of the above-described halogenated metal and lanthanide metal as well. For example, the electron transport region ETR may include KI:Yb, RbI:Yb, and/or the like as a co-deposited material. In some embodiments, the electron transport region ETR may include a metal oxide (such as $Li_2O$, BaO, and/or Liq(8-hydroxyl-lithium quinolate)), but embodiments of the present disclosure are not limited thereto. The electron transport region ETR may be also formed of a mixture material of an electron transport material and an insulating organo metal salt. The organo metal salt may be a material having an energy band gap of about 4 eV or more. For example, the organo metal salt may include, for example, metal acetates, metal benzoates, metal acetoacetates, metal acetylacetonates, and/or metal stearates.

The electron transport region ETR may further include, for example, at least one of 2,9-dimethyl-4,7-diphenyl-1,10-phenanthroline (BCP) or 4,7-diphenyl-1,10-phenanthroline (Bphen) in addition to the above-described materials, but embodiments of the present disclosure are not limited thereto.

The electron transport region ETR may include the aforementioned compounds of the electron transport region in at least one of the electron injection layer EIL, the electron transport layer ETL, or the hole blocking layer HBL.

When the electron transport region ETR includes the electron transport layer ETL, the thickness of the electron transport layer ETL may be about 100 Å to about 1000 Å, for example, about 150 Å to about 500 Å. When the thickness of the electron transport layer ETL satisfies the above-described range, satisfactory electron transport properties may be achieved without substantial increase of a driving voltage. When the electron transport region ETR includes the electron injection layer EIL, the thickness of the electron injection layer EIL may be about 1 Å to about 100 Å, for example, about 3 Å to about 90 Å. When the thickness of the electron injection layer EIL satisfies the above-described range, satisfactory electron injection properties may be achieved without substantial increase of a driving voltage.

The second electrode EL2 is provided on the electron transport region ETR. The second electrode EL2 may be a common electrode. The second electrode EL2 may be a cathode or an anode, but embodiments of the present disclosure are not limited thereto. For example, when the first electrode EL1 is an anode, the second electrode EL2 may be a cathode, and when the first electrode EL1 is a cathode, the second electrode EL2 may be an anode.

The second electrode EL2 may be a transmissive electrode, a transflective electrode, or a reflective electrode. When the second electrode EL2 is a transmissive electrode, the second electrode EL2 may include transparent metal oxide (such as indium tin oxide (ITO), indium zinc oxide (IZO), zinc oxide (ZnO), indium tin zinc oxide (ITZO), and/or the like).

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, W, or a compound or mixture thereof (for example, AgMg, AgYb, or MgYb). In some embodiments, the second electrode EL2 may have a multilayered structure including a reflective film or a transflective film formed of the aforementioned materials and a transparent conductive film formed of indium tin oxide (ITO), indium zinc oxide (IZO), zinc oxide (ZnO), indium tin zinc oxide (ITZO), and/or the like. For example, the second electrode EL2 may include the above-described metal material, a combination of two or more metal materials selected from the above-described metal materials, or a oxide of the above-described metal materials.

In some embodiments, the second electrode EL2 may be connected to an auxiliary electrode. When the second electrode EL2 is connected to the auxiliary electrode, the resistance of the second electrode EL2 may decrease.

In some embodiments, a capping layer CPL may be further disposed on (e.g., outside) the second electrode EL2 of the light-emitting element ED according to an embodiment. The capping layer CPL may include multiple layers or a single layer. In an embodiment, the capping layer CPL may include the amine compound according to an embodiment described above.

In an embodiment, the capping layer CPL may be an organic layer or an inorganic layer. For example, when the capping layer CPL includes an inorganic material, the inorganic material may include an alkali metal compound (such as LiF) and/or an alkaline earth metal compound (such as $MgF_2$, SiON, SiNx, SiOy, and/or the like).

For example, when the capping layer CPL includes an organic material, the organic material may includes α-NPD, NPB, TPD, m-MTDATA, $Alq_3$, CuPc, N4,N4,N4',N4'-tetra (biphenyl-4-yl) biphenyl-4,4'-diamine (TPD15), 4,4',4"-tris (carbazol-9-yl) triphenylamine (TCTA), etc., epoxy resins, or acrylate (such as methacrylate). However, embodiments of the present disclosure are not limited thereto, and the capping layer CPL may include at least one selected from Compounds P1 to P5:

P1

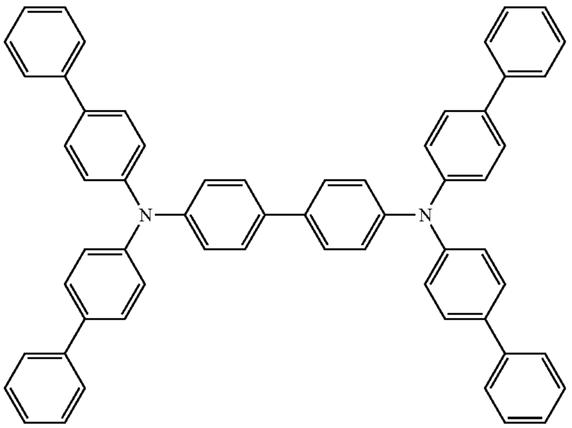

P2

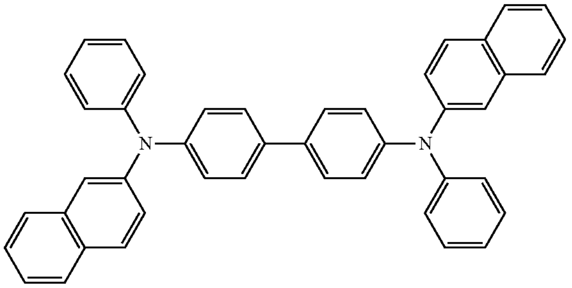

-continued

P3

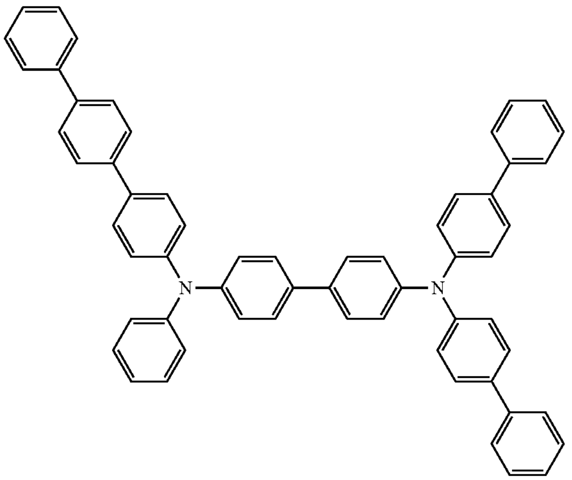

P4

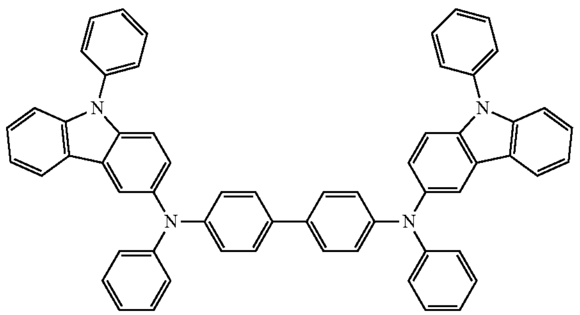

P5

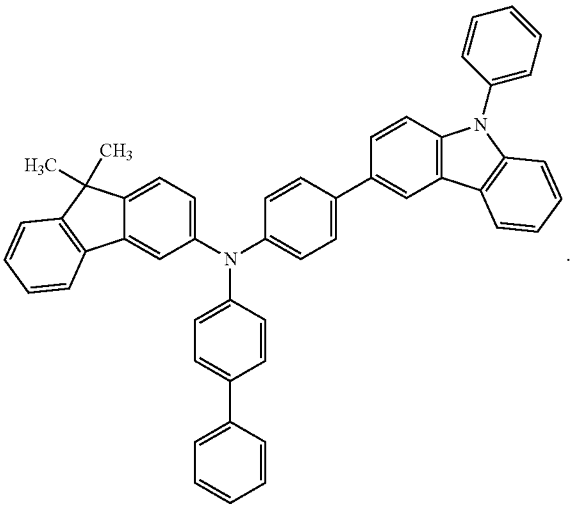

.

In some embodiments, the refractive index of the capping layer CPL may be about 1.6 or more. For example, for light in the wavelength range of about 550 nm to about 660 nm, the refractive index of the capping layer CPL may be about 1.6 or more.

Figure 8:
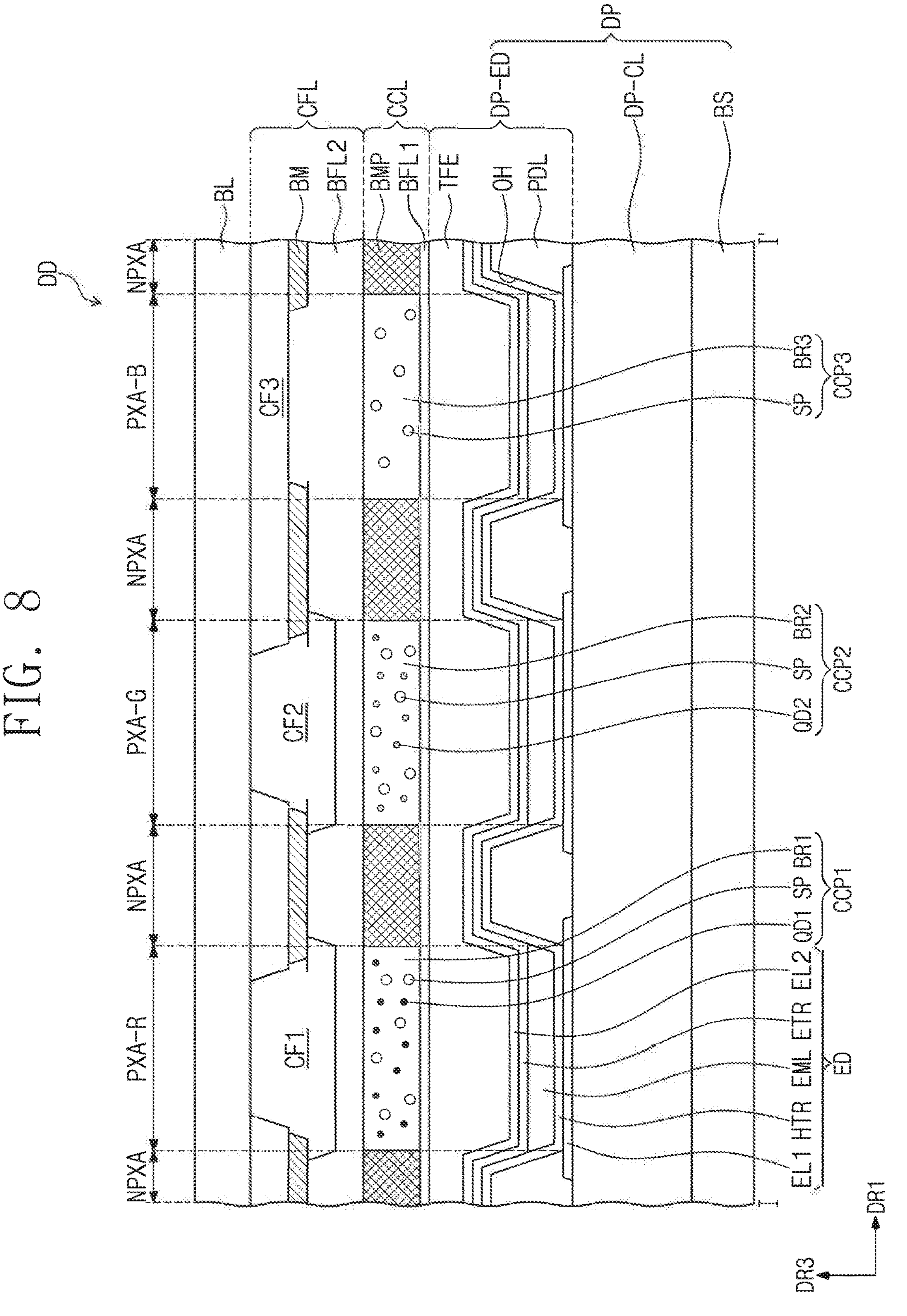
FIG. 8 is a cross-sectional view of a display device according to an embodiment.
Figure 9:
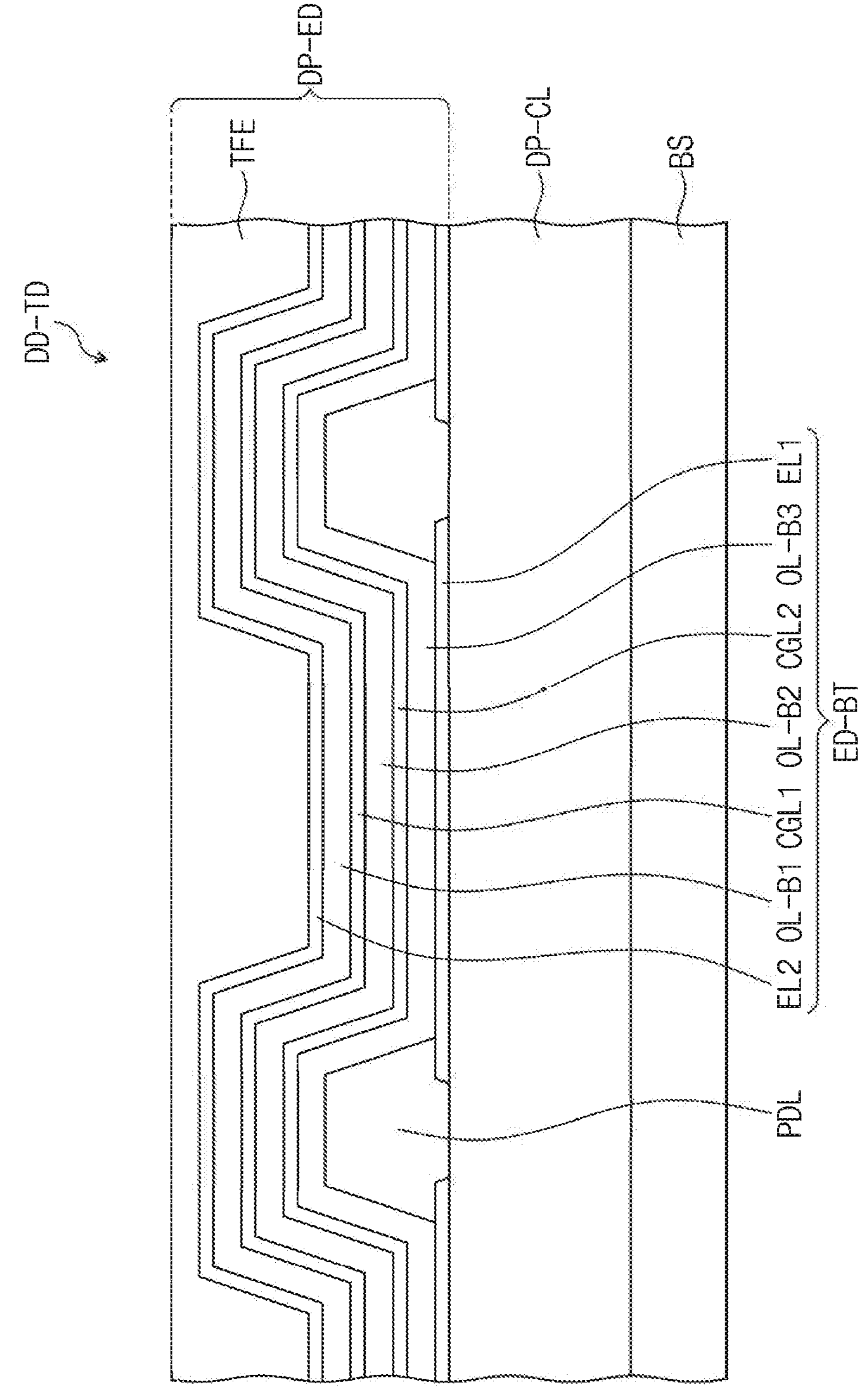
FIG. 9 is a cross-sectional view of a display device according to an embodiment.

FIGS. 8 and 9 are each a cross-sectional view of a display device according to an embodiment. In the description of the display device according to an embodiment described with reference to FIGS. 8 and 9, the contents overlapping with those described in FIGS. 1 to 7 will not be described again, and differences will be mainly described.

Referring to FIG. 8, a display device DD according to an embodiment may include a display panel DP including a display element layer DP-ED, a light control layer CCL disposed on the display panel DP, and a color filter layer CFL.

In an embodiment illustrated in FIG. 8, the display panel DP may include a base layer BS, a circuit layer DP-CL provided on the base layer BS, and a display element layer DP-ED, and the display element layer DP-ED may include a light-emitting element ED.

The light-emitting element ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. In some embodiments, the same structure of any light-emitting element in FIGS. 3 to 7 described above may be adopted by the light-emitting element ED illustrated in FIG. 8.

Referring to FIG. 8, the emission layer EML may be disposed in the opening OH defined in the pixel-defining film PDL. For example, the emission layer EML separated by the pixel-defining film PDL and provided to correspond to each of light-emitting regions PXA-R, PXA-G, and PXA-B may be to emit light of the same wavelength range. In a display device DD according to an embodiment, the emission layer EML may be to emit blue light. In some embodiments, the emission layer EML may be provided as a common layer over all of the light-emitting regions PXA-R, PXA-G, and PXA-B.

The light control layer CCL may be disposed on the display panel DP. The light control layer CCL may include a light conversion body. The light conversion body may be a quantum dot or a phosphor. The light conversion body may convert the wavelength of received light and emit the converted light. For example, the light control layer CCL may be a layer including a quantum dot or a layer including a phosphor.

The light control layer CCL may include a plurality of light control portions CCP1, CCP2, and CCP3. The light control portions CCP1, CCP2, and CCP3 may be spaced apart from each other.

Referring to FIG. 8, a division pattern BMP may be disposed between the light control portions CCP1, CCP2, and CCP3 spaced apart from each other, but embodiments are not limited thereto. In FIG. 8, the division pattern BMP is illustrated as being non-overlapping with the light control portions CCP1, CCP2, and CCP3, but edges of the light control portions CCP1, CCP2, and CCP3 may at least partially overlap with the division pattern BMP.

The light control layer CCL may include a first light control portion CCP1 including a first quantum dot QD1 configured to convert a first color light provided in the light-emitting element ED into a second color light, a second light control portion CCP2 including a second quantum dot QD2 configured to convert the first color light into a third color light, and a third light control portion CCP3 configured to transmit the first color light.

In an embodiment, the first light control portion CCP1 may provide red light, which is a second color light, and the second light control portion CCP2 may provide green light, which is a third color light. The third light control portion CCP3 may transmit and provide blue light, which is the first light provided by the light-emitting element ED. For example, the first quantum dot QD1 may be a red quantum dot, and the second quantum dot QD2 may be a green quantum dot. The same description as described above may be applied to the quantum dots QD1 and QD2.

In some embodiments, the light control layer CCL may further include a scatterer SP. The first light control portion CCP1 may include the first quantum dot QD1 and the scatterer SP, the second light control portion CCP2 may include the second quantum dot QD2 and the scatterer SP, and the third light control portion CCP3 may not include a quantum dot but may include the scatterer SP.

The scatterer SP may be an inorganic particle. For example, the scatterer SP may include at least one of $TiO_2$, ZnO, $Al_2O_3$, $SiO_2$, or hollow silica, or may be a mixture of two or more scatterer materials, each including at least one selected from $TiO_2$, ZnO, $Al_2O_3$, $SiO_2$, and hollow silica.

The first light control portion CCP1, the second light control portion CCP2, and the third light control portion CCP3 may include base resins BR1, BR2, and BR3, respectively, and these base resins BR1, BR2, and BR3 may disperse the quantum dots QD1 and QD2, and the scatterer SP. In an embodiment, the first light control portion CCP1 may include the first quantum dot QD1 and the scatterer SP dispersed in the first base resin BR1, the second light control portion CCP2 may include the second quantum dot QD2 and scatterer SP dispersed in the second base resin BR2, and the third light control portion CCP3 may include the scatterer SP dispersed in the third base resin BR3. The base resins BR1, BR2, and BR3 are media in which the quantum dots QD1 and QD2 and the scatterer SP are dispersed, and may be formed to include one or more suitable resin compositions, which may be generally referred to as binders. For example, the base resins BR1, BR2, and BR3 may be acrylic resins, urethane-based resins, acrylic-based resins, epoxy-based resins, and/or the like. The base resins BR1, BR2, and BR3 may be a transparent resins. In an embodiment, the first base resin BR1, the second base resin BR2, and the third base resin BR3 may be the same as or different from each other.

The light control layer CCL may include a barrier layer BFL1. The barrier layer BFL1 may serve to prevent or reduce penetration of moisture and/or oxygen (hereinafter referred to as "moisture/oxygen"). The barrier layer BFL1 may be disposed on the light control portions CCP1, CCP2, and CCP3 to prevent or reduce the light control portions CCP1, CCP2, and CCP3 from being exposed to moisture/oxygen. In some embodiments, the barrier layer BFL1 may cover the light control portions CCP1, CCP2, and CCP3. In some embodiments, a barrier layer BFL2 may be provided between the light control portions CCP1, CCP2, and CCP3 and the color filter layer CFL as well.

The barrier layers BFL1 and BFL2 may include at least one inorganic layer. For example, the barrier layers BFL1 and BFL2 may be formed including an inorganic material. For example, the barrier layers BFL1 and BFL2 may be formed to include silicon nitride, aluminum nitride, zirconium nitride, titanium nitride, hafnium nitride, tantalum nitride, silicon oxide, aluminum oxide, titanium oxide, tin oxide, cerium oxide, silicon oxynitride, and/or a metal thin film in which light transmittance is secured. In some embodiments, the barrier layers BFL1 and BFL2 may each independently further include an organic film. The barrier layers BFL1 and BFL2 may be comprised of a single layer or a plurality of layers.

In a display device DD according to an embodiment, the color filter layer CFL may be disposed on the light control layer CCL. For example, the color filter layer CFL may be directly disposed on the light control layer CCL. In this case, the barrier layer BFL2 may not be provided.

The color filter layer CFL may include a light-shielding portion BM and filters CF1, CF2, and CF3. The color filter layer CFL may include a first filter CF1 configured to transmit a second color light, a second filter CF2 configured to transmit a third color light, and a third filter CF3 configured to transmit a first color light. For example, the first filter CF1 may be a red filter, the second filter CF2 may be a green filter, and the third filter CF3 may be a blue filter. Each of the filters CF1, CF2, and CF3 may include polymer photosensitive resin and/or a pigment and/or dye. The first filter CF1 may include a red pigment and/or dye, the second filter CF2 may include a green pigment and/or dye, and the third filter CF3 may include a blue pigment and/or dye. In some embodiments, the third filter CF3 may not include a pigment or dye. For example, the third filter CF3 may include polymer photosensitive resin, and may not include a pigment or dye. The third filter CF3 may be transparent. The third filter CF3 may be formed of a transparent photosensitive resin.

In some embodiments, in an embodiment, the first filter CF1 and the second filter CF2 may each be a yellow filter. The first filter CF1 and the second filter CF2 may not be separated from each other and may be provided integrally.

The light-shielding portion BM may be a black matrix. The light-shielding portion BM may be formed by including an organic light-shielding material or an inorganic light-shielding material including a black pigment or a black dye. The light-shielding portion BM may prevent or reduce light leakage, and may separate the boundaries between the adjacent filters CF1, CF2, and CF3. In some embodiments, the light-shielding portion BM may be formed of a blue filter.

The first to the third filters CF1, CF2, and CF3 may be disposed to respectively correspond to a red light-emitting region PXA-R, a green light-emitting region PXA-G, and a blue light-emitting region PXA-B.

A base substrate BL may be disposed on the color filter layer CFL. The base substrate BL may be a member configured to provide a base surface on which the color filter layer CFL and the light control layer CCL are disposed. The base substrate BL may be a glass substrate, a metal substrate, a plastic substrate, and/or the like. However, embodiments of the present disclosure are not limited thereto, and the base substrate BL may be an inorganic layer, an organic layer, or a composite material layer. In some embodiments, unlike the illustrated configuration, the base substrate BL may not be provided in an embodiment.

FIG. 9 is a cross-sectional view illustrating a portion of a display device according to an embodiment. FIG. 9 illustrates a cross-sectional view of a portion corresponding to the display panel DP of FIG. 8. In the display device DD-TD according to an embodiment, the light-emitting element ED-BT may include a plurality of light-emitting structures OL-B1, OL-B2, and OL-B3. The light-emitting element ED-BT may include a first electrode EL1 and a second electrode EL2 that face each other, and a plurality of light-emitting structures OL-B1, OL-B2, and OL-B3 that are provided by sequentially stacking in a thickness direction between the first electrode EL1 and the second electrode EL2. Each of the light-emitting structures OL-B1, OL-B2, and OL-B3 may include the emission layer EML (FIG. 7), and the hole transport region HTR and the electron transport region ETR disposed between the emission layer EML (FIG. 7)

For example, the light-emitting element ED-BT included in the display device DD-TD according to an embodiment may be a light-emitting element having a tandem structure including a plurality of emission layers.

In an embodiment illustrated in FIG. 9, all the light emitted from each of the light-emitting structures OL-B1, OL-B2, and OL-B3 may be blue light. However, embodiments of the present disclosure are not limited thereto, and the wavelength ranges of light emitted from each of the light-emitting structures OL-B1, OL-B2, and OL-B3 may be different from each other. For example, the light-emitting element ED-BT including the plurality of light-emitting structures OL-B1, OL-B2, and OL-B3 that emit light of different wavelength ranges may be to emit white light.

A charge generating layer CGL1 and CGL2 may be disposed between the adjacent light-emitting structures OL-B1, OL-B2, and OL-B3. The charge generating layer CGL1 and CGL2 may include a p-type charge generating layer and/or an n-type charge generating layer.

At least one of the light-emitting elements OL-B1, OL-B2, and OL-B3 included in the display device DD-TD may include the amine compound according to an embodiment as described above.

The light-emitting element ED may include the amine compound according to an embodiment in at least one functional layer disposed between the first electrode EL1 and the second electrode EL2, and thus improved emission efficiency and/or improved service life characteristics may be achieved. The light-emitting element ED may include the amine compound according to an embodiment in at least one of a hole transport region HTR, an emission layer EML, or an electron transport region ETR, disposed between the first electrode EL1 and the second electrode EL2, or in the capping layer CPL.

For example, the amine compound according to an embodiment may be included in the hole transport region HTR of the light-emitting element ED, and the light-emitting element according to an embodiment may exhibit excellent or suitable emission efficiency and/or long service life characteristics.

The amine compound according to an embodiment described above has a molecular structure which essentially contains a bicycloheptyl group, and additionally one of an adamantyl group, a cyclohexyl group, or a bicycloheptyl group, thereby having excellent or suitable durability and/or heat resistance, and thus improved service life characteristics may be achieved. In some embodiments, improved material stability and ability to transport holes of the amine compound according to an embodiment may contribute to the long service life and/or high efficiency characteristics of the light-emitting element.

Hereinafter, the amine compound according to an embodiment and the light-emitting element according to an embodiment of the present disclosure will be described in more detail with reference to examples and comparative examples. The following examples are provided to assist the understanding of the present disclosure, and the scope of the present disclosure is not limited thereto.

EXAMPLE

1. Synthesis of an Amine Compound

First, a synthetic method of the amine compound according to an embodiment of the present disclosure will be described in more detail with reference to synthetic methods of compounds 1, 2, 30, 41, 50, and 65 in Compound Group 1. In some embodiments, the synthetic methods of the amine compound explained are only examples, and the synthetic method of the amine compound according to embodiments of the present disclosure are not limited thereto.

(1) Synthesis of Compound 1

Amine Compound 1 according to an example may be synthesized through the reaction steps below.

Synthesis of Intermediate A

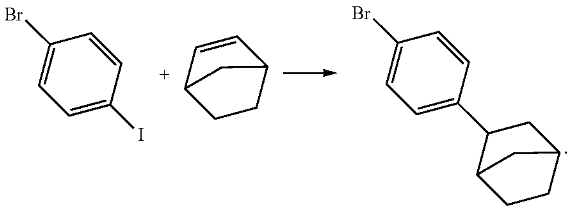

Intermediate A 12.9 g (100 mmol) of 1-bromo-4-iodobenzene, 23.3 g of bicyclo[2,2,1]hept-2-ene, 19.5 g (100 mmol) of CuI, and 25.8 g (200 mmol) of $K_2CO_3$ were added to a 200 mL DMF solution, and then stirred at about 150° C. for about 96 hours. After the reaction was completed, the mixture was cooled to room temperature and extracted three times with ethyl acetate/$H_2O$. Then, the resultant mixture was dried with anhydrous magnesium sulfate and purified through column chromatography by utilizing a mixed solvent (MC:HEX=1:10), thereby obtaining Intermediate A (18.8 g, yield 80%).

Synthesis of Intermediate B

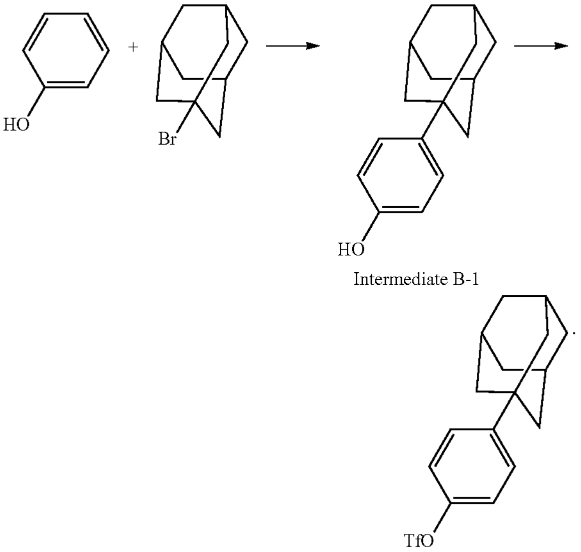

Intermediate B-1

Intermediate B

Synthesis of Intermediate B-1

21.4 g (100 mmol) of 1-bromoadamantane was added to 100 mL of phenol, and then stirred at about 110° C. for about 24 hours. After the reaction was completed, the resulting solid was washed three times with 60° C. $H_2O$. After dissolving the solid in MC, the resultant solution was dried with anhydrous magnesium sulfate, thereby obtaining Intermediate B-1 (22 g, yield 100%).

Synthesis of Intermediate B 22 g of Intermediate B-1 and 10 g of $Et_3N$ were dissolved in MC, and then the solution was cooled to about 0° C. 50 g of trifluoromethanesulfonic anhydride was added for 1 hour. Then, the mixture was heated to room temperature and stirred for 4 hours. After the reaction was completed, the resulting solid was extracted three times with 60° C. $Et_2O$ $H_2O$. The resultant mixture was dried with anhydrous magnesium sulfate and then separated and purified through column chromatography, thereby obtaining Intermediate B (33 g, yield 90%).

Synthesis of Compound 1

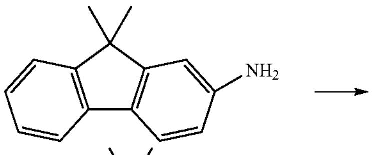

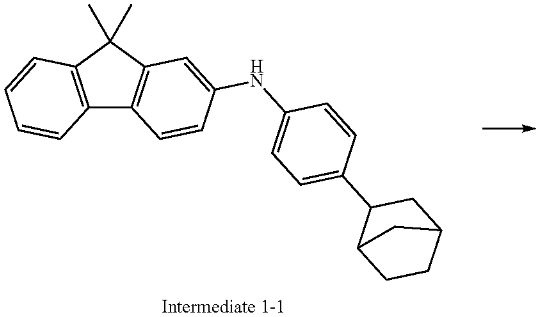

Intermediate 1-1

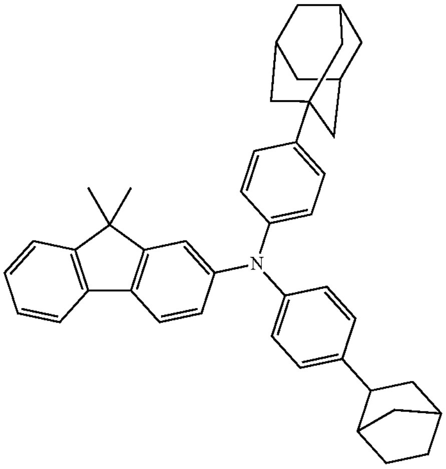

1

Synthesis of Intermediate 1-1 4.2 g (20 mmol) of 9,9-dimethyl-9H-fluoren-2-amine, 5 g (20 mmol) of Intermediate A, 0.915 g (1 mol) of $Pd_2(dba)_3$, 0.410 g (1 mL) of Sphos, and 3.6 g (40 mmol) of NaOtBu were dissolved in toluene (200 mL), then stirred at about 90° C. for about 2 hours, and then extracted three times with $Et_2O/H_2O$. The resulting product was dried with anhydrous magnesium sulfate, and then separated and purified through column chromatography, thereby obtaining Intermediate 1-1 (6.8 g(18 mmol), yield 90%).

Synthesis of Compound 1

Compound 1 (5.3 g (9 mmol), yield 90%) was obtained in substantially the same method as the synthesis of Intermediate 1-1, except that Intermediate 1-1 was utilized instead of 9,9-dimethyl-9H-fluoren-2-amine and Intermediate B instead of Intermediate A.

Compound 1 was identified by confirming the molecular weight and NMR results as follow. [$C_{44}H_{47}N$ M+1: 590.45, $^1H$ NMR (500 MHz, $CDCl_3$) Γ=7.80 (m, 2H), 7.60 (d, 1H), 7.55-7.10 (m, 12H), 2.5-0.9 (m, 32H)]

(2) Synthesis of Compound 2

Amine Compound 2 according to an embodiment may be synthesized by the reaction steps or tasks below.

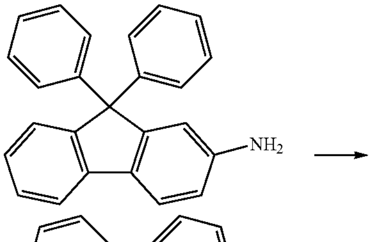

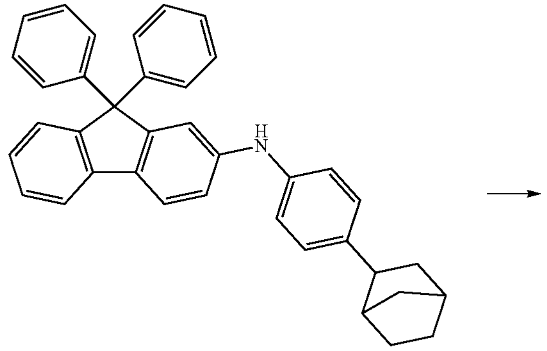

Intermediate 2-1

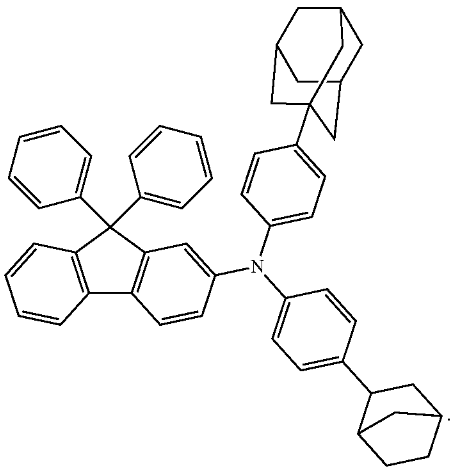

2

Synthesis of Intermediate 2-1

Intermediate 2-1 (9 g (18 mmol), yield 90%) was obtained in substantially the same method as the synthesis of Intermediate 1-1, except that 9,9-diphenyl-9H-fluoren-2-amine was utilized instead of 9,9-dimethyl-9H-fluoren-2-amine.

Synthesis of Compound 2

Compound 2 (6.4 g (9 mmol), yield 90%) was obtained in substantially the same method as the synthesis of compound 1, except that Intermediate 2-1 was utilized instead of Intermediate 1-1.

Compound 2 was identified by confirming the molecular weight and NMR results as follow. [$C_{54}H_{51}N$ M+1: 714.55, $^1H$ NMR (500 MHz, $CDCl_3$) δ=7.80 (m, 2H), 7.60 (d, 1H), 7.55-7.10 (m, 22H), 2.5-1.5 (m, 26H)]

(3) Synthesis of Compound 30

Amine Compound 30 according to an embodiment may be synthesized by the reaction steps or tasks below.

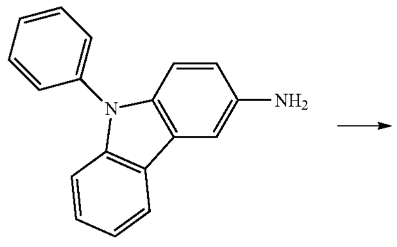

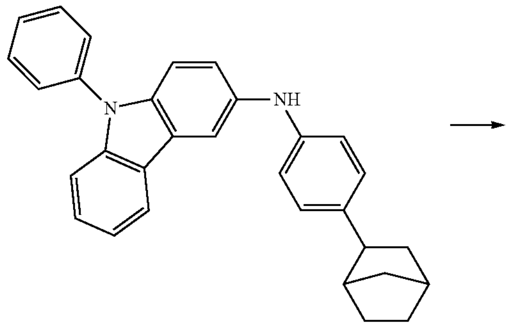

Intermediate 30-1

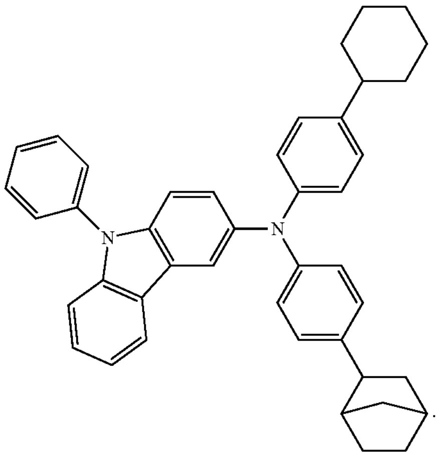

30

Synthesis of Intermediate 30-1

Intermediate 30-1 (7.7 g (18 mmol), yield 90%) was obtained in substantially the same method as the synthesis of Intermediate 1-1, except that 9-phenyl-9H-carbazol-3-amine was utilized instead of 9,9-dimethyl-9H-fluoren-2-amine.

Synthesis of Compound 30

Compound 30 (5.2 g (9 mmol), yield 90%) was obtained in substantially the same method as the synthesis of compound 1, except that Intermediate 30-1 was utilized instead of Intermediate 1-1 and 1-bromo-4-cyclohexylbenzene was utilized instead of Intermediate A.

Compound 30 was identified by confirming the molecular weight and NMR results as follow. [$C_{43}H_{42}N_2$ M+1: 587.33, $^1$H NMR (500 MHz, $CDCl_3$) δ=7.80 (m, 2H), 7.60 (d, 1H), 7.55-7.10 (m, 17H), 2.5-1.5 (m, 22H)]

(4) Synthesis of Compound 41

Amine Compound 41 according to an embodiment may be synthesized by the reaction steps or tasks below.

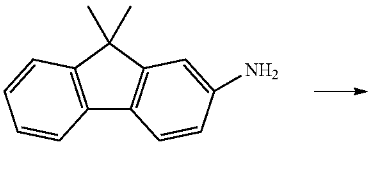

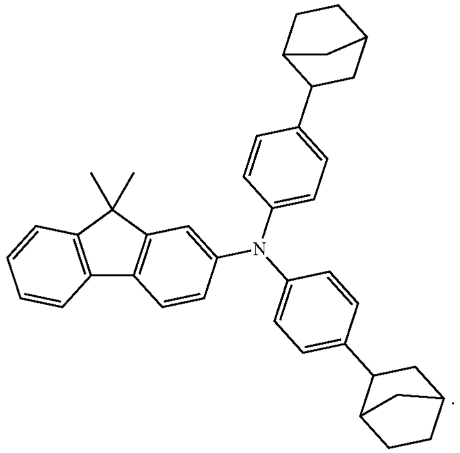

41

Compound 41 (5.2 g (9 mmol), yield 90%) was obtained in substantially the same method as the synthesis of Compound 1, except that 2.1 g (10 mmol) of 9,9-dimethyl-9H-fluoren-2-amine was utilized instead of Intermediate 1-1.

Compound 41 was identified by confirming the molecular weight and NMR results as follow. [$C_{41}H_{43}N$ M+1: 550.52, 1H NMR (500 MHz, CDC13) δ=7.80 (m, 2H), 7.60 (d, 1H), 7.55-7.10 (m, 12H), 2.5-1.5 (m, 22H), 1.3 (d, 6H)]

(5) Synthesis of Compound 50

Amine Compound 50 according to an embodiment may be synthesized by the reaction steps or tasks below.

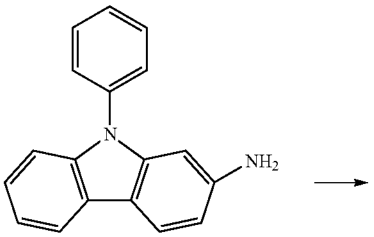

-continued

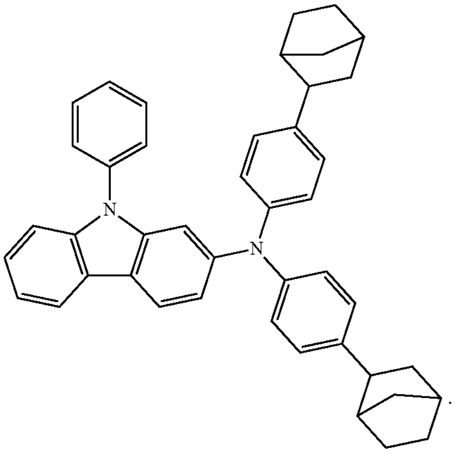

50

-continued

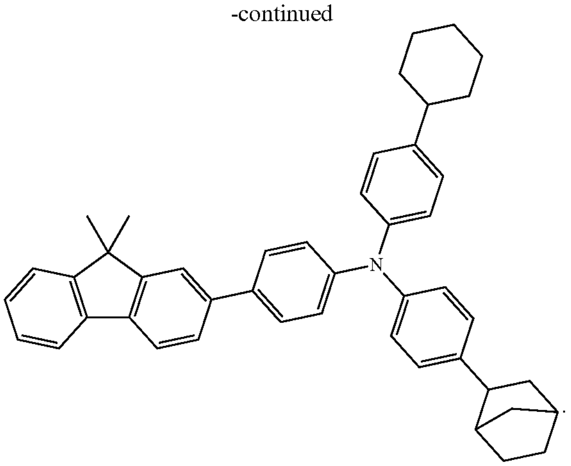

65

Compound 50 (5.38 g (9 mmol), yield 90%) was obtained in substantially the same method as the synthesis of Compound 41, except that 2.6 g (10 mmol) of 9-phenyl-9H-carbazol-2-amine was utilized instead of 9,9-dimethyl-9H-fluoren-2-amine.

Compound 50 was identified by confirming the molecular weight and NMR results as follow. [$C_{44}H_{42}N_2$ M+1: 599.22, $^1$H NMR (500 MHz, $CDCl_3$) δ=7.80 (m, 2H), 7.60 (d, 1H), 7.55-7.10 (m, 17H), 2.5-1.5 (m, 22H)]

(6) Synthesis of Compound 65

Amine Compound 65 according to an embodiment may be synthesized by the reaction steps or tasks below.

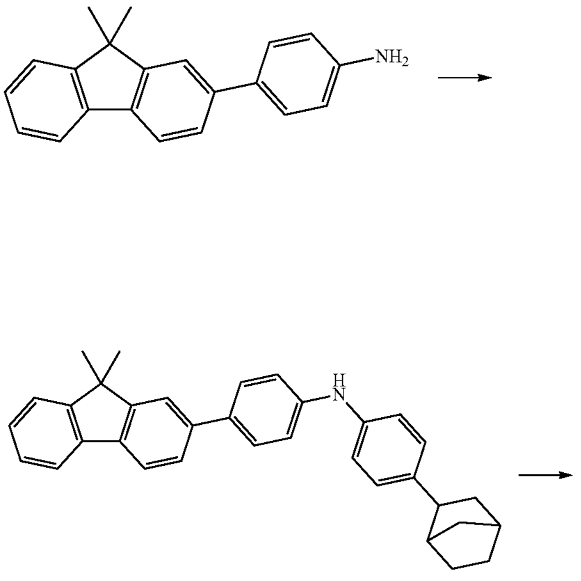

Intermediate 65-1

Synthesis of Intermediate 65-1

Intermediate 65-1 (8.19 g (18 mmol), yield 90%) was obtained in substantially the same method as the synthesis of Intermediate 1-1, except that 4-(9,9-dimethyl-9H-fluoren-2-yl)aniline was utilized instead of 9,9-dimethyl-9H-fluoren-2-amine.

Synthesis of Compound 65

Compound 65 (5.5 g (9 mmol), yield 90%) was obtained in substantially the same method as the synthesis of compound 1, except that Intermediate 65-1 was utilized instead of Intermediate 1-1 and 1-bromo-4-cyclohexylbenzene was utilized instead of Intermediate A.

Compound 65 was identified by confirming the molecular weight and NMR results as follow. [$C_{46}H_{47}N$ M+1: 614.44, $^1$H NMR (500 MHz, $CDCl_3$) δ=7.80 (m, 2H), 7.60 (d, 1H), 7.55-7.10 (m, 16H), 2.5-1.5 (m, 22H), 1.3 (d, 6H)]

2. Manufacture and Evaluation of a Light-Emitting Element (Manufacture of a light-emitting element)

The light-emitting element including the amine compound according to an embodiment in a hole transport layer was manufactured by the below method. Examples 1 to 6 and Comparative Examples 1 and 2 are light-emitting elements manufactured to include one hole transport layer, and Examples 7 and 8 are light-emitting elements manufactured to include two hole transport layers.

Compound 1, Compound 2, Compound 30, Compound 41, Compound 50, and Compound 65 were each utilized as a hole transport material to manufacture the light-emitting elements of Examples 1 to 6, respectively. The light-emitting elements of Examples 7 and 8 were manufactured utilizing Compound 1 as a first hole transport layer material, and utilizing the respective amine derivative compounds of Compound 85 and Compound 97, respectively, as a second hole transport layer material.

In Comparative Example 1, the light-emitting element was manufactured utilizing Comparative Compound NPB (C1) as a hole transport layer material. In Comparative Example 2, the light-emitting element was manufactured utilizing Comparative Example Compound C2 as a hole transport layer material.

The Example Compounds and Comparative Compounds utilized in element manufacture are shown.

Example Compounds
1
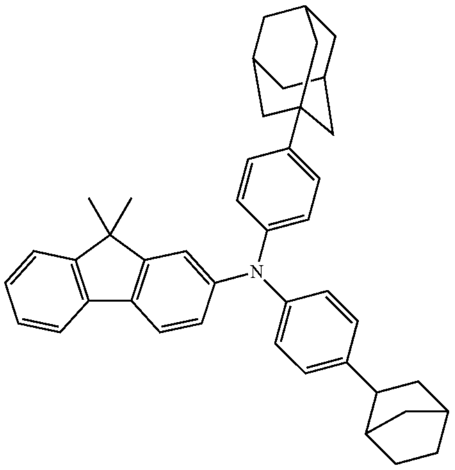
2
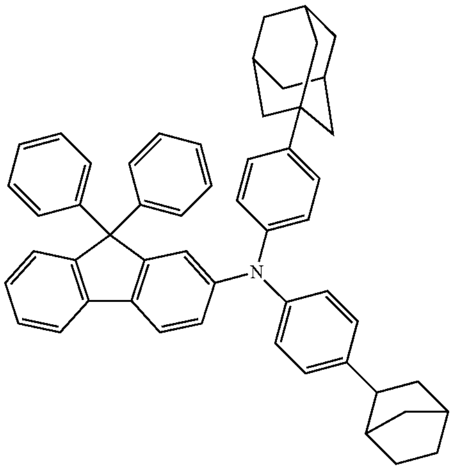
30
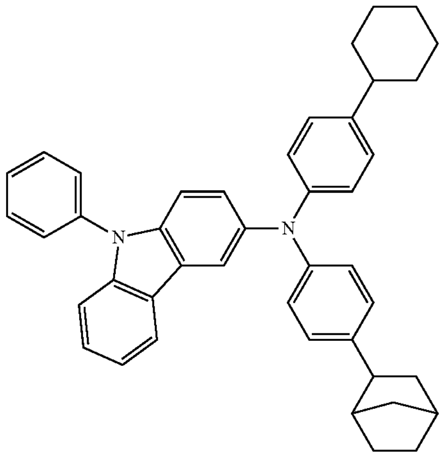
-continued
41
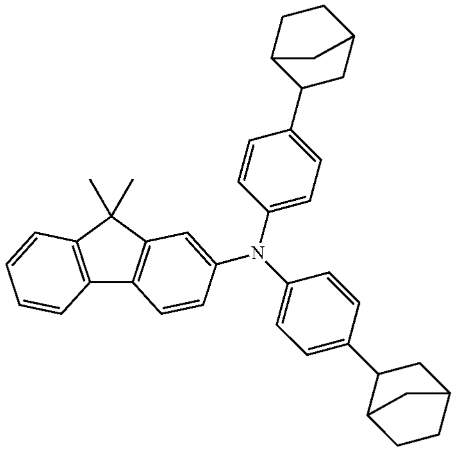
50
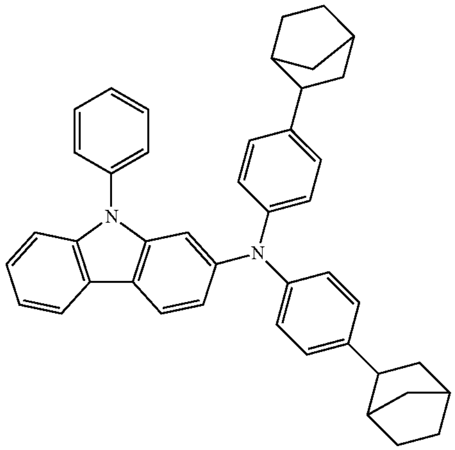
65
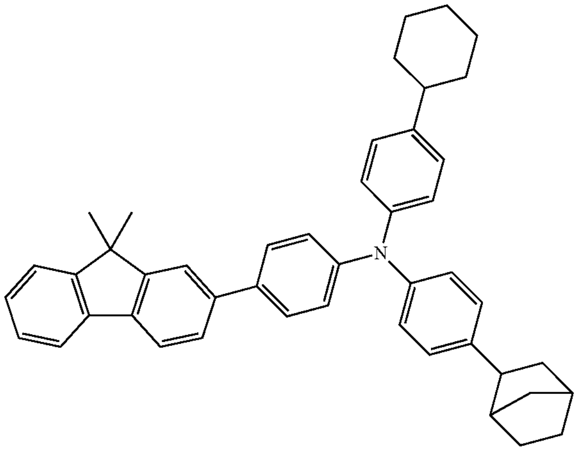

-continued

85

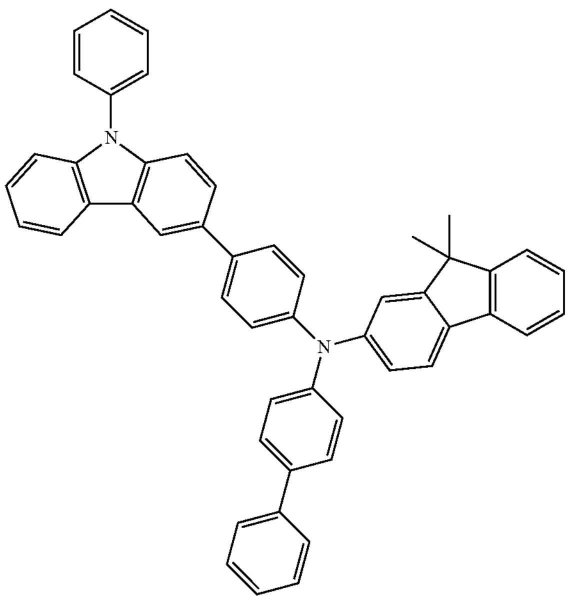

97

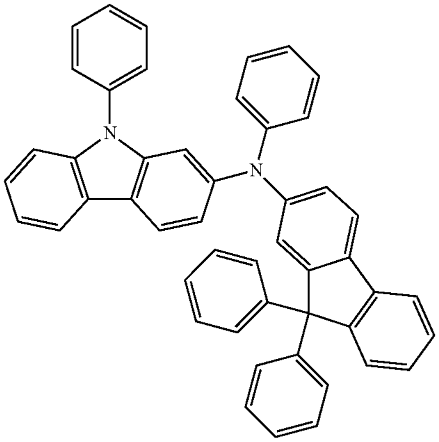

Comparative Compounds

C1

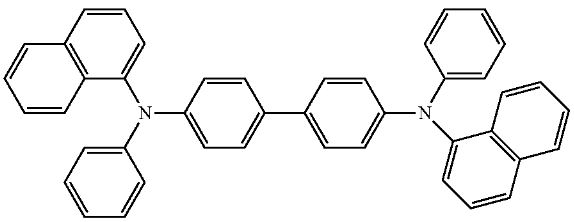

-continued

C2

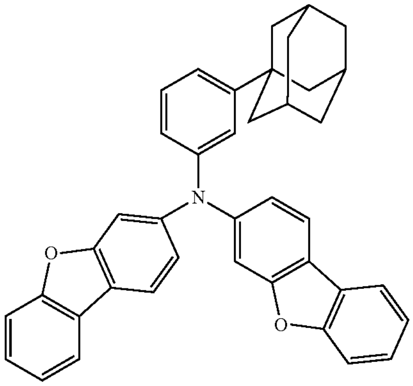

Other Compounds Utilized in Element Manufacture

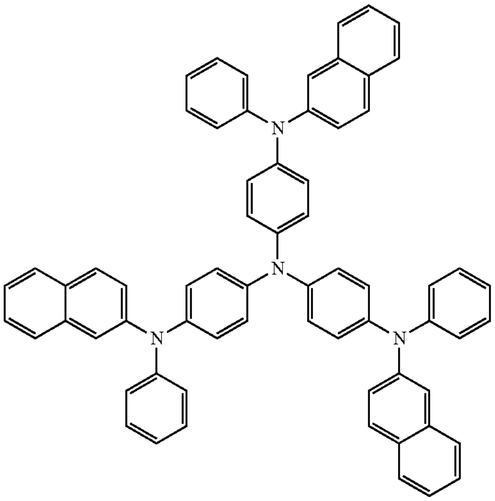

2-TNATA

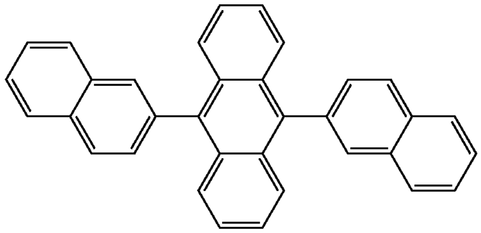

ADN

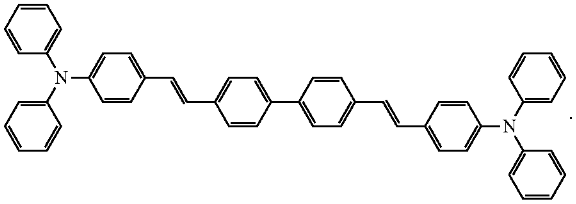

DPAVBi

An 1200 Å-thick ITO layer patterned on a glass substrate was cleansed by ultrasonic waves for five minutes each utilizing isopropyl alcohol and pure water. After ultrasonic cleansing, the substrate was irradiated with UV rays for about 30 minutes, and treated with ozone. Then, 2-TNATA was deposited to a thickness of about 600 Å to form a hole injection layer. After that, in Examples 1 to 6 and Comparative Examples 1 to 2, a respective Example Compound or Comparative Compound were deposited to a thickness of about 300 Å to form a hole transport layer. In some embodiments, in Examples 7 and 8, Compound 1 was deposited to form a first hole transport layer, and then Compound 85 and Compound 97 were deposited to form a second hole transport layer. In Examples 7 and 8, each of the first hole transport layer and the second hole transport layer was deposited to a thickness of about 150 Å.

Then, ADN and DPAVBi, a blue fluorescent dopant, were co-deposited in a weight ratio of about 98:2 to form a 300 Å-thick emission layer. After that, $Alq_3$ was deposited to 300 Å-thick to form an electron transport layer, and LiF was deposited to 10 Å-thick to form an electron injection layer.

Then, Al was provided to a thickness of about 3000 Å to form a second electrode.

In each of the Examples and Comparative Examples, a hole injection layer, a hole transport layer, an emission layer, an electron transport layer, an electron injection layer, and a second electrode were formed by utilizing a vacuum deposition device.

Evaluation of characteristics of a light-emitting element

The evaluation result of the light-emitting elements according to Examples 1 to 7 and Comparative Examples 1 to 2 are shown in Table 1. Driving voltage, luminance, emission efficiency, and half-life of each light-emitting element thus manufactured are compared and shown in Table 1. In evaluation results of characteristic for Examples and Comparative Example shown in Table 1, emission efficiency represents efficiency values at a current density of about 50 $mA/cm^2$, and half-life represents luminance reducing time at about 100 $mA/cm^2$. In some embodiments, it was confirmed that all of the manufactured elements exhibits a blue emission color.

The current density, voltage, and emission efficiency of the light-emitting elements of the Examples and Comparative Example were determined in a dark room utilizing a 2400 series SourceMeter from Keithley Instrument Co., a luminance meter CS-200 from Konica Minolta, Inc., and PC Program LabVIEW 2.0 for measurement from National Instrument Co., in Japan.

TABLE 1

| Element Manufacturing example | Hole transport layer material HTL1 | HTL2 | Driving voltage (V) | Luminance ($cd/m^2$) | Emission efficiency (cd/A) | Emission color | Half-life (hr @ 100 mA/ $cm^2$) |
|---|---|---|---|---|---|---|---|
| Example 1 | Compound 1 | — | 4.75 | 3075 | 6.15 | Blue | 520 |
| Example 2 | Compound 2 | — | 4.72 | 3060 | 6.12 | Blue | 510 |
| Example 3 | Compound 30 | — | 4.75 | 3010 | 6.02 | Blue | 560 |
| Example 4 | Compound 41 | — | 4.73 | 2965 | 5.93 | Blue | 615 |
| Example 5 | Compound 50 | — | 4.72 | 3045 | 6.09 | Blue | 570 |
| Example 6 | Compound 65 | — | 4.72 | 3115 | 6.23 | Blue | 500 |
| Example 7 | Compound 1 | Compound 85 | 4.72 | 3300 | 6.60 | Blue | 580 |
| Example 8 | Compound 1 | Compound 97 | 4.72 | 3270 | 6.54 | Blue | 520 |
| Cornparative Example 1 | C1 | | 5.01 | 2820 | 5.62 | Blue | 415 |
| Comparative Example 2 | C2 | | 5.52 | 2340 | 4.24 | Blue | 260 |

Referring to the results in Table 1, it may be seen that the light-emitting elements of the Examples, which each utilized the amine compound according to an embodiment as a hole transport layer material, showed low driving voltage, high luminance characteristics, excellent or suitable element efficiency and improved element service life characteristics.

For example, referring to Table 1, it may be seen that Examples 1 to 8 showed low voltage, high luminance, long service life, and high efficiency characteristics compared to Comparative Examples 1 and 2.

Accordingly, the results show that Examples 1 to 8 exhibited improvement in both (e.g., simultaneously) emission efficiency and emission life compared to Comparative Examples 1 and 2. For example, both (e.g., simultaneously) element efficiency and element service life of the light-emitting element according to an embodiment may be improved by utilizing the amine compounds according to an embodiment having compound structure including at least one bicycloheptyl group.

The amine compound according to an embodiment may contribute to low voltage, long service life, and high efficiency characteristics of a light-emitting device due to having a compound structure containing one bicycloheptyl group, and further containing at least one of an adamantyl group, a cyclohexyl group, or a bicycloheptyl group. The light-emitting element has the amine compound according to an embodiment, and thus may exhibit both (e.g., simultaneously) long service life and/or high efficiency characteristics.

A light-emitting element according to an embodiment may include the amine compound according to an embodiment in a hole transport region, thereby exhibiting high efficiency and/or long service life characteristics.

An amine compound according to an embodiment may improve the emission efficiency and/or service life of the light-emitting element.

Although the example embodiments of the present disclosure have been described herein, it is understood that one or more suitable changes and modifications can be made by those skilled in the art within the spirit and scope of the present disclosure defined by claims and equivalents thereof or the equivalents.

As used herein, the terms "substantially," "about," and similar terms are used as terms of approximation and not as terms of degree, and are intended to account for the inherent deviations in measured or calculated values that would be recognized by those of ordinary skill in the art. "About" or "approximately," as used herein, is inclusive of the stated value and means within an acceptable range of deviation for the particular value as determined by one of ordinary skill in the art, considering the measurement in question and the error associated with measurement of the particular quantity (i.e., the limitations of the measurement system). For example, “about” may mean within one or more standard deviations, or within ±30%, 20%, 10%, 5% of the stated value.

Any numerical range recited herein is intended to include all sub-ranges of the same numerical precision subsumed within the recited range. For example, a range of “1.0 to 10.0” is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Therefore, the technical scope of the present disclosure is not limited to the content described in the detailed description of the specification, and various changes in form and details may be made without departing from the spirit and scope of the present disclosure as set forth in the following claims and their equivalents.

What is claimed is:

1. A light-emitting element comprising:

a first electrode;

a second electrode on the first electrode; and at least one functional layer between the first electrode and the second electrode and comprising an amine compound represented by Formula 1:

Formula 1

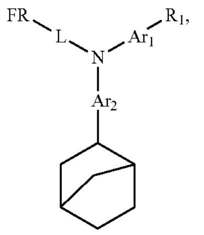

wherein, in Formula 1, $R_1$ is an adamantyl group, a cyclohexyl group, or a bicycloheptyl group, $Ar_1$ and $Ar_2$ are each independently a substituted or unsubstituted arylene group having 6 to 30 ring-forming carbon atoms, L is a direct linkage, a substituted or unsubstituted arylene group having 6 to 30 ring-forming carbon atoms, or a substituted or unsubstituted heteroarylene group having 2 to 30 ring-forming carbon atoms, and FR is represented by Formula 2:

Formula 2

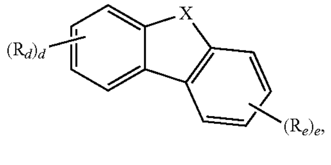

wherein, in Formula 2,

X is $CR_aR_b$, N, $NR_c$, O, or S, $R_a$ to $R_c$ are each independently a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring, d and e are each independently an integer of 0 to 4, and $R_a$ and $R_e$ are each independently a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring, and wherein when $R_1$ is a bicycloheptyl group, then at least one of $Ar_1$ or $Ar_2$ is a substituted or unsubstituted phenylene group.

2. The light-emitting element of claim 1, wherein:

the at least one functional layer comprises an emission layer, a hole transport region between the first electrode and the emission layer, and an electron transport region between the emission layer and the second electrode, and the hole transport region comprises the amine compound.

3. The light-emitting element of claim 2, wherein:

the hole transport region comprises a hole injection layer on the first electrode, and a hole transport layer on the hole injection layer, and the hole transport layer comprises the amine compound.

4. The light-emitting element of claim 1, wherein the amine compound represented by Formula 1 is represented by Formula 1-1 or Formula 1-2:

Formula 1-1

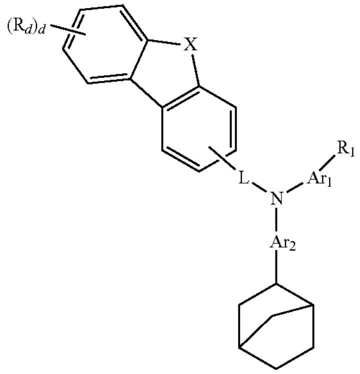

-continued

Formula 1-2

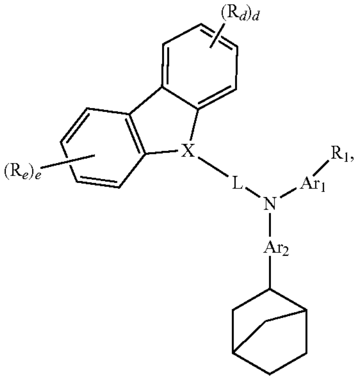

and wherein, in Formula 1-1 and Formula 1-2, $R_1$, L, $Ar_1$, and $Ar_2$ are each independently the same as defined in Formula 1, and X, $R_d$, $R_e$, d, and e are each independently the same as defined in Formula 2.

5. The light-emitting element of claim 4, wherein the amine compound represented by Formula 1-2 is represented by Formula 1-2A:

Formula 1-2A

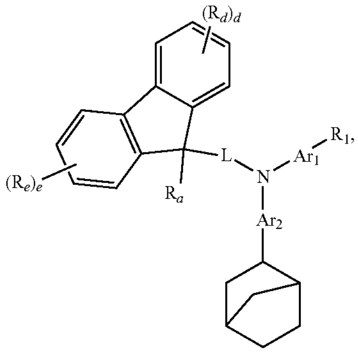

and wherein, in Formula 1-2A, $R_1$, L, $Ar_1$, and $Ar_2$ are each independently the same as defined in Formula 1, and $R_a$, $R_d$, $R_e$, d, and e are each independently the same as defined in Formula 2.

6. The light-emitting element of claim 1, wherein in Formula 1, $Ar_1$ and $Ar_2$ are a substituted or unsubstituted phenylene group.

7. The light-emitting element of claim 1, wherein the amine compound represented by Formula 1 is represented by Formula 1A:

Formula 1A

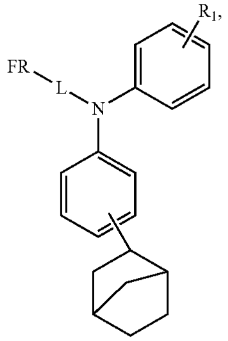

and wherein, in Formula 1A, $R_1$, L, and FR are each independently the same as defined in Formula 1.

8. The light-emitting element of claim 1, wherein the amine compound represented by Formula 1 is represented by any one of compounds in Compound Group 1:

Compound Group 1

1

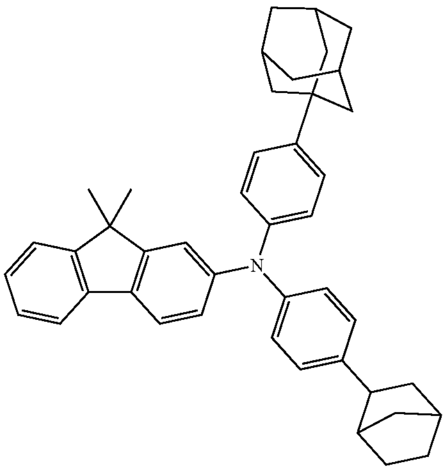

2

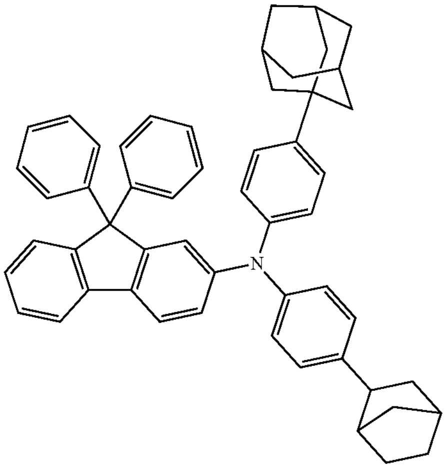

-continued
3
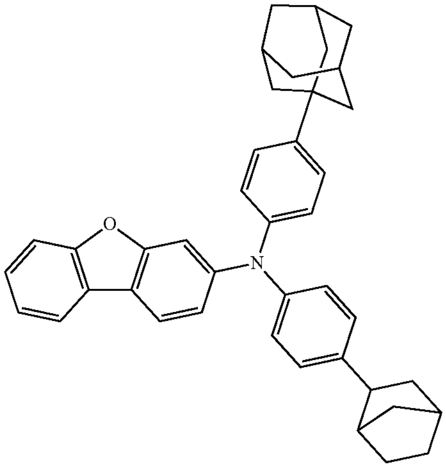
4
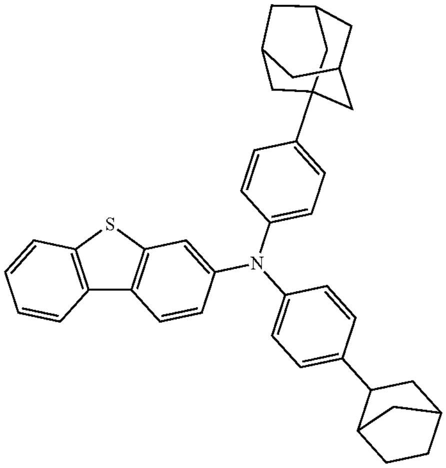
5
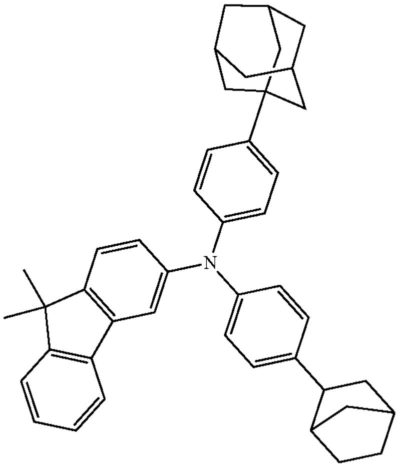
-continued
6
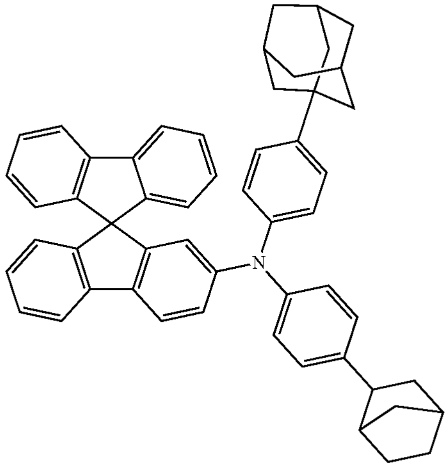
7
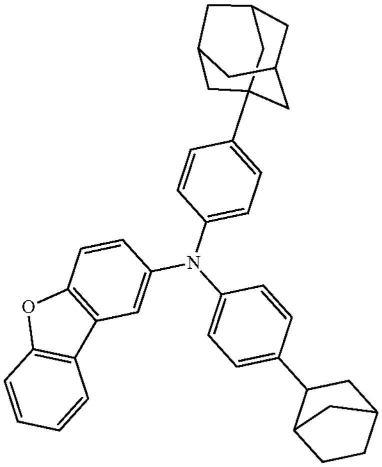
8
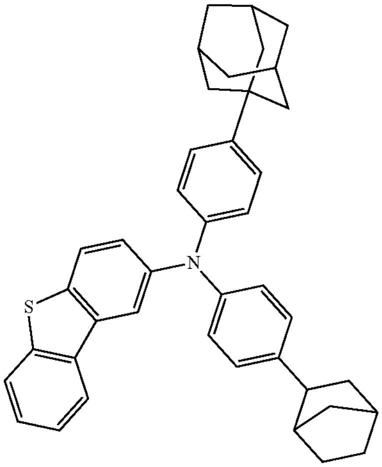

-continued
9
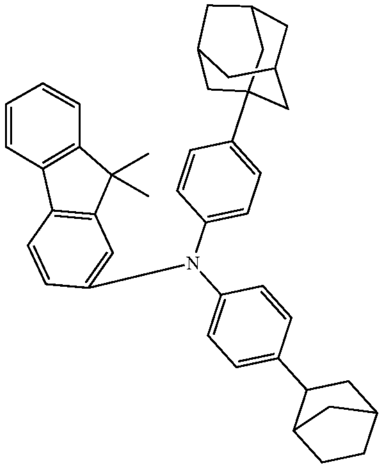
10
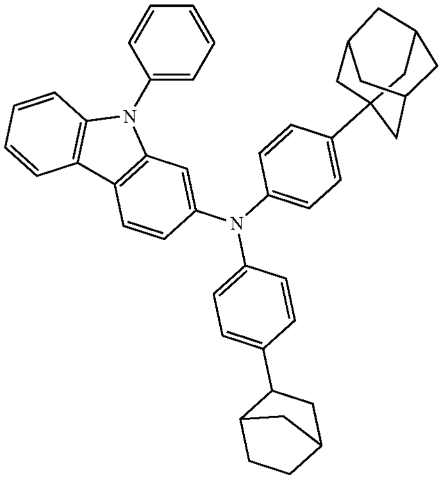
11
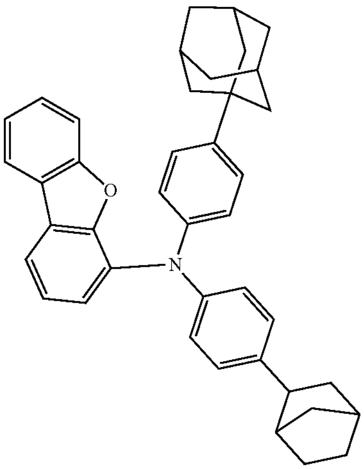
-continued
12
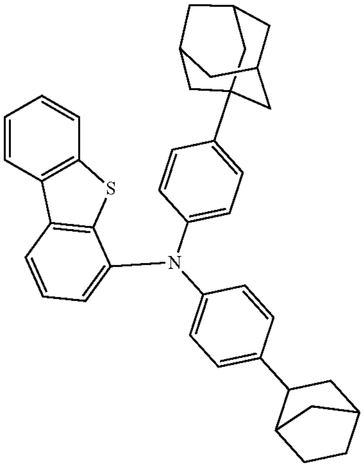
13
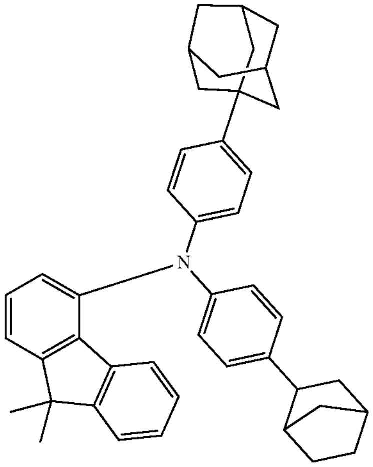
14
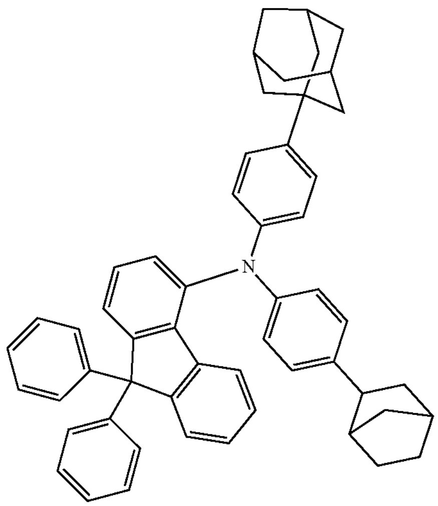

-continued
15
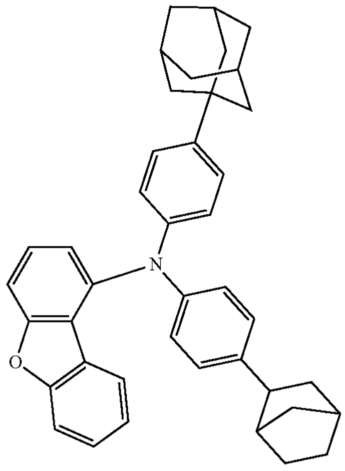
16
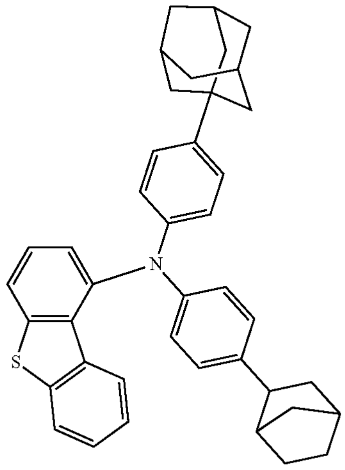
17
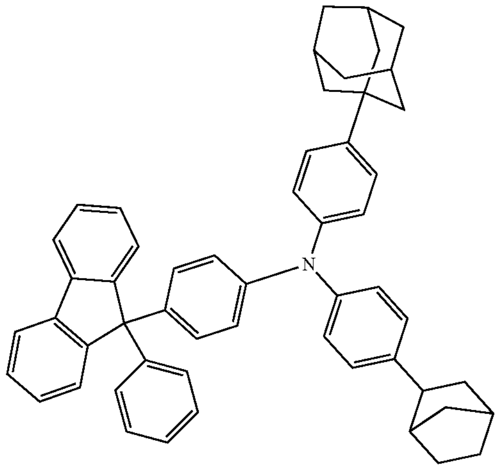
-continued
18
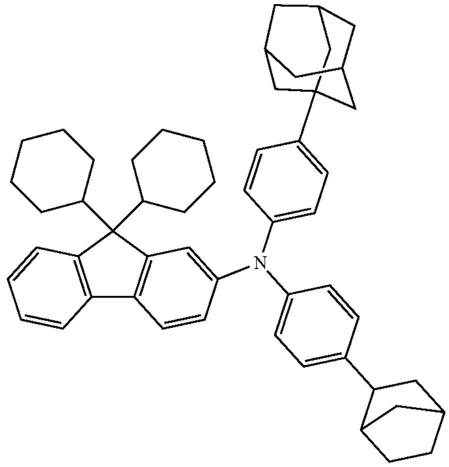
19
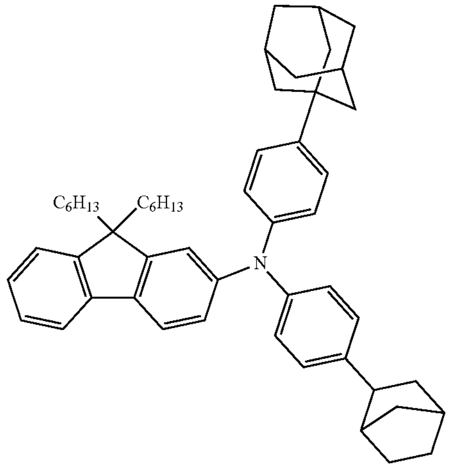
20
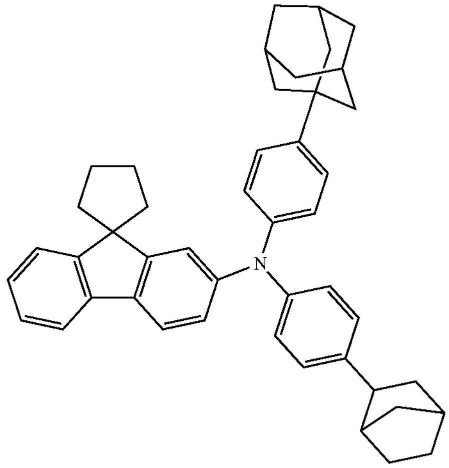

-continued
21
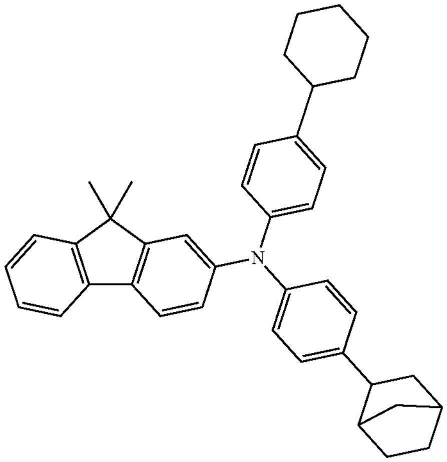
22
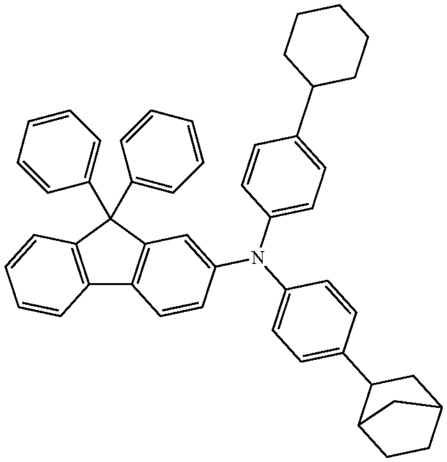
23
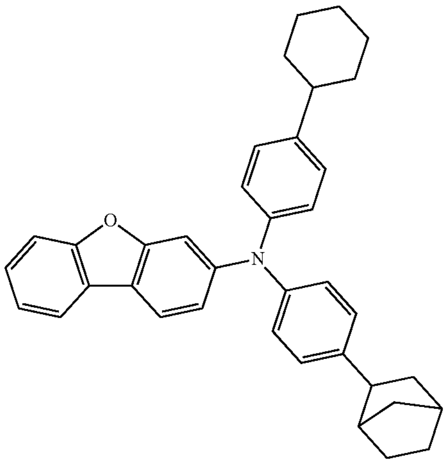
-continued
24
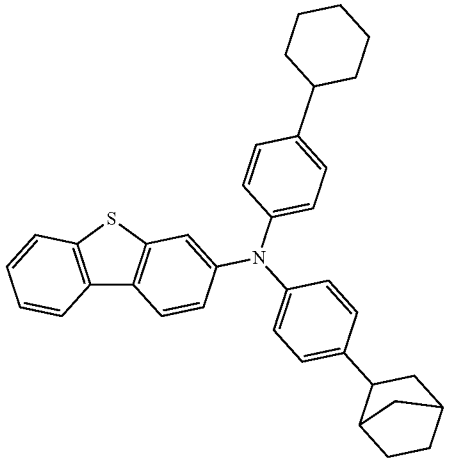
25
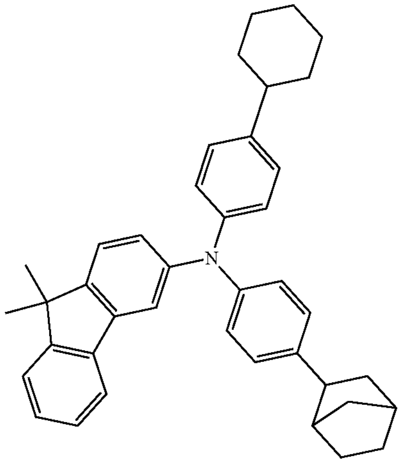
26
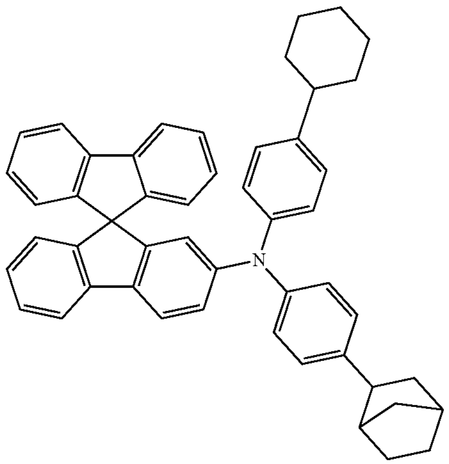

-continued
27
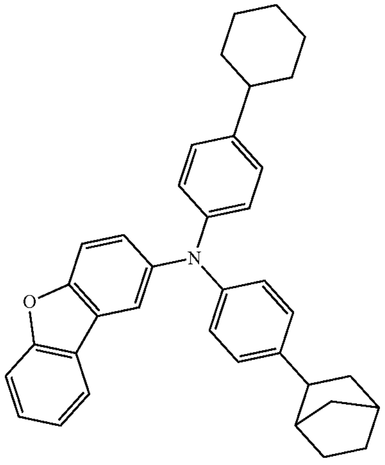
28
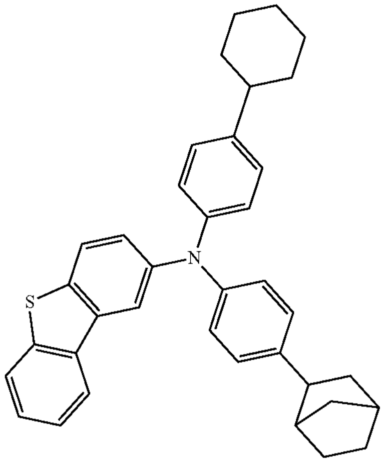
29
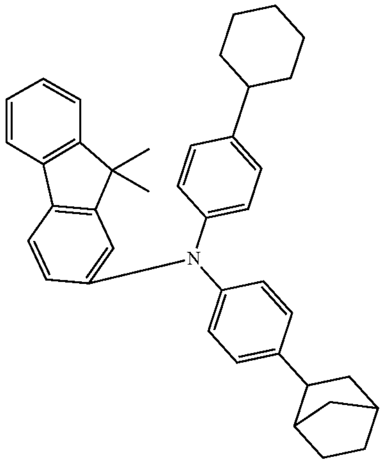
-continued
30
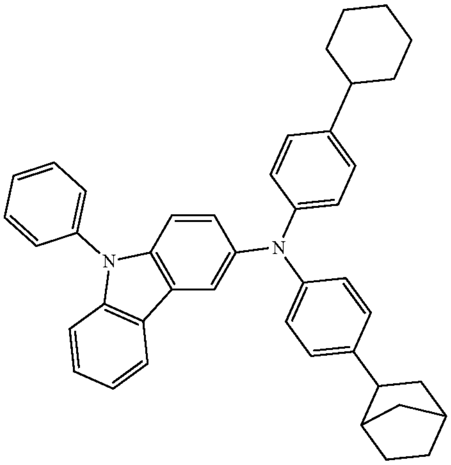
31
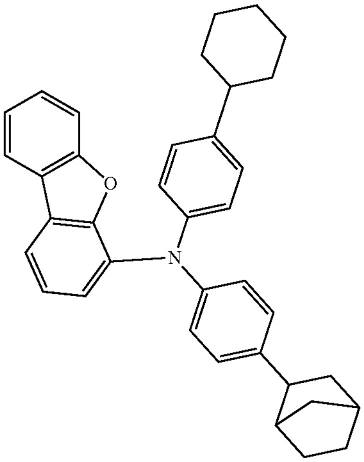
32
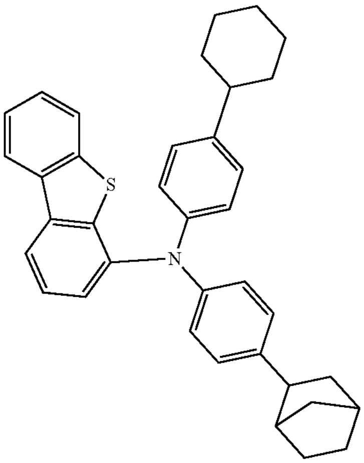

-continued
33
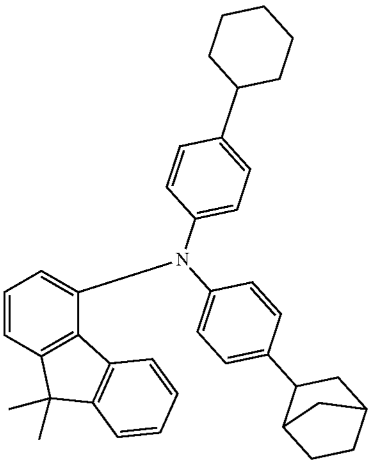
34
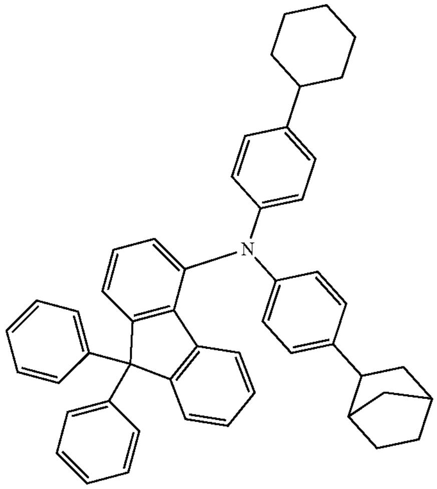
35
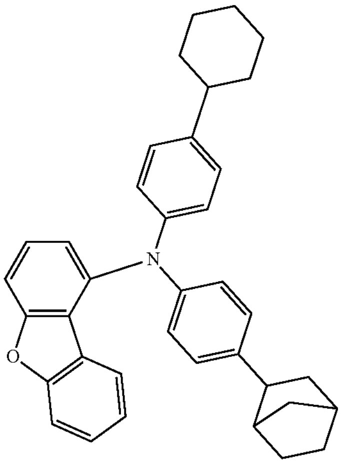
-continued
36
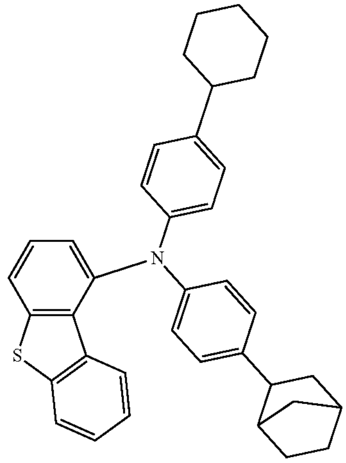
37
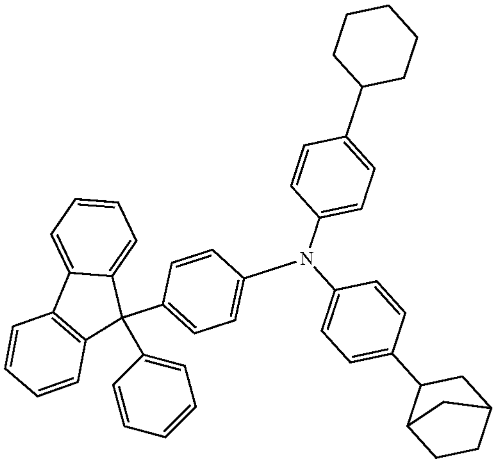
38
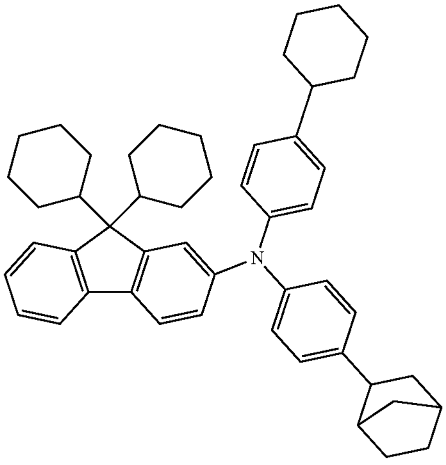

-continued
39
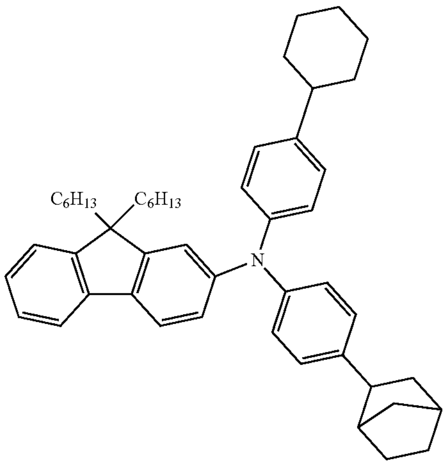
40
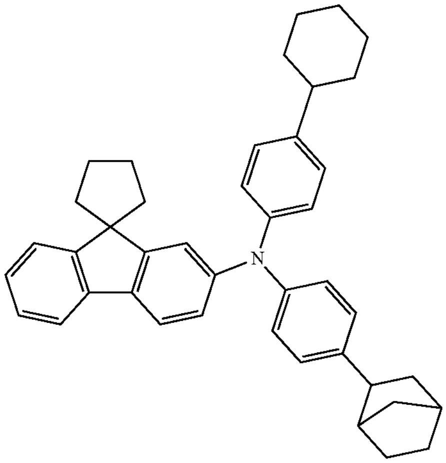
41
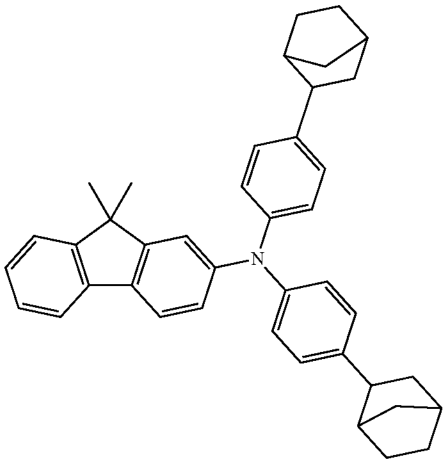
-continued
42
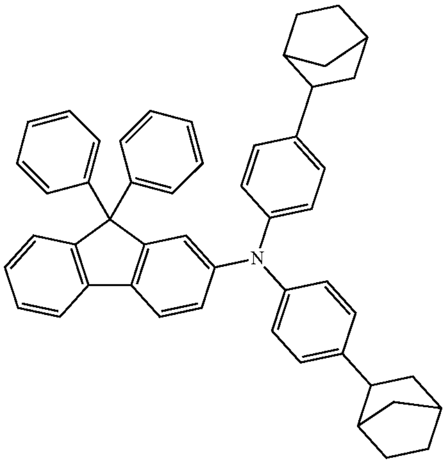
43
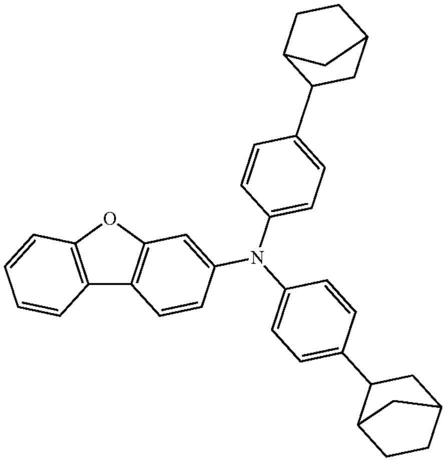
44
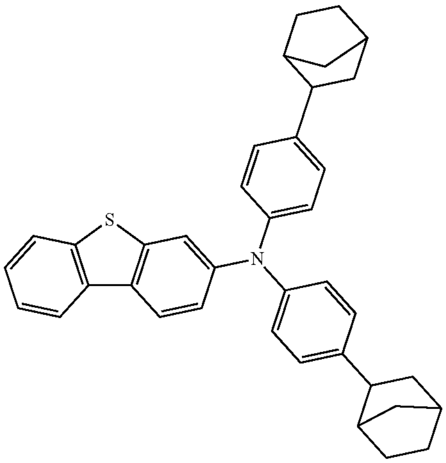

-continued
45
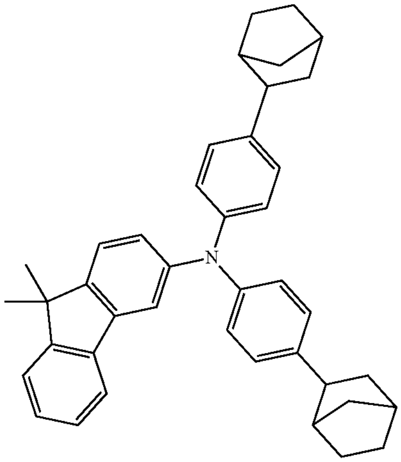
46
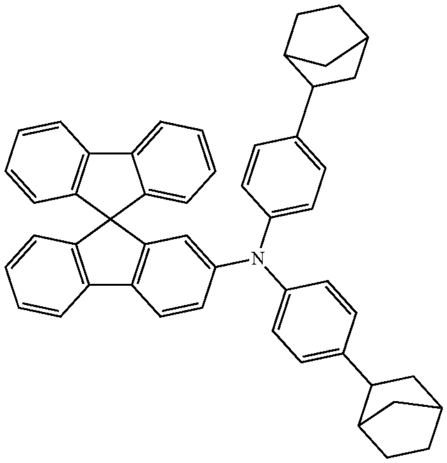
47
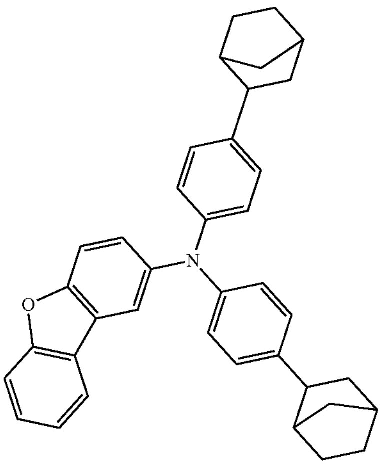
-continued
48
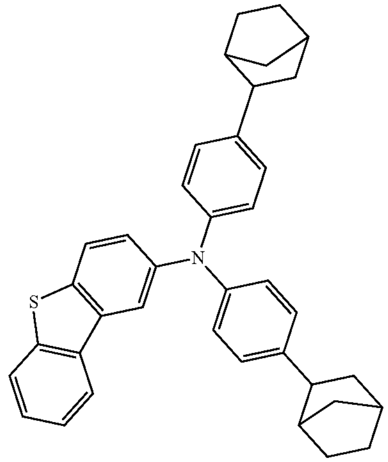
49
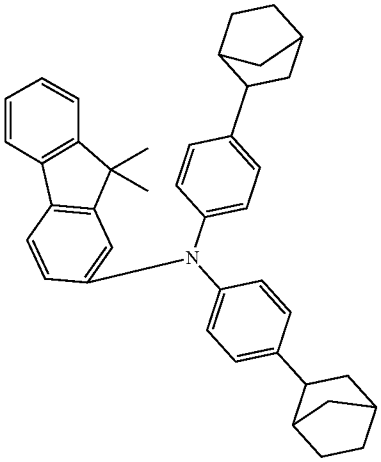
50
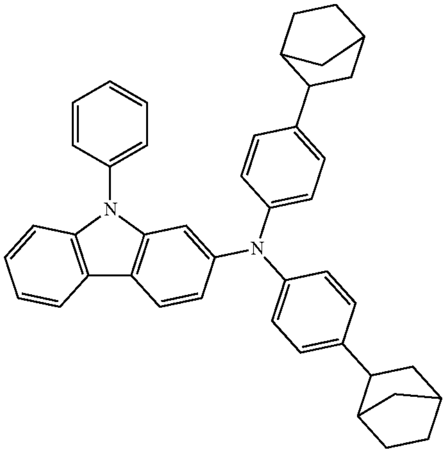

51
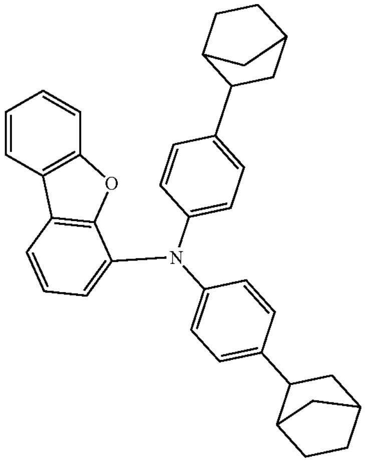
52
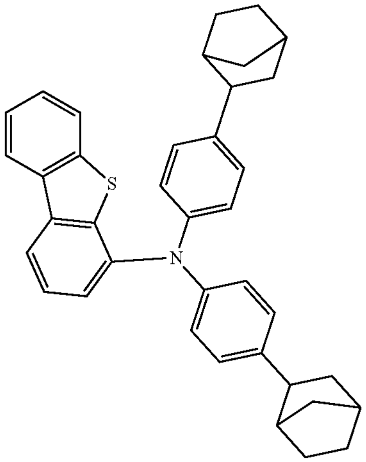
53
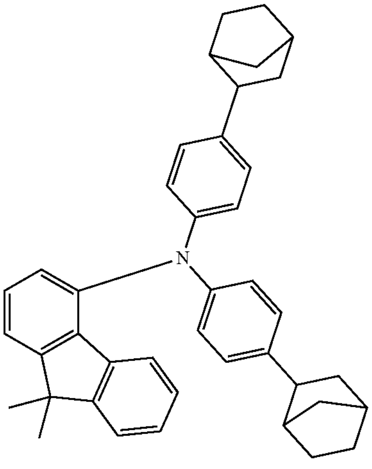
54
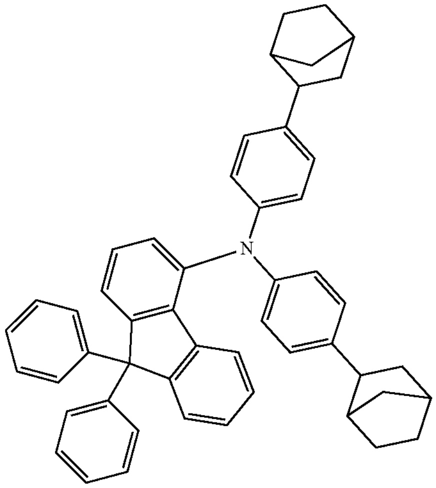
55
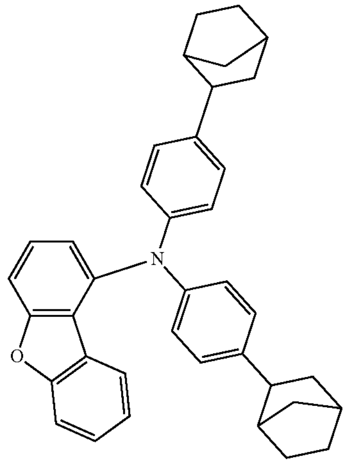
56
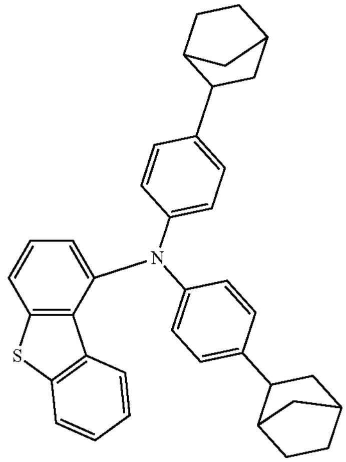

-continued
57
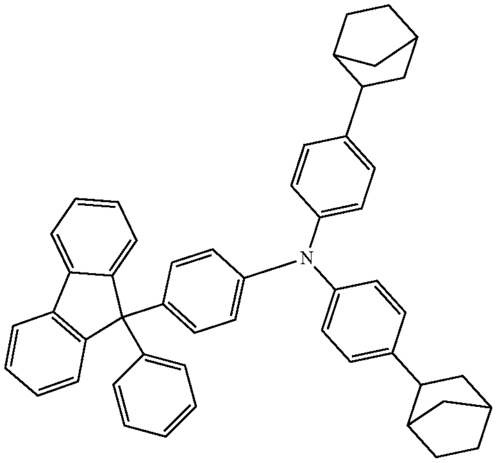
58
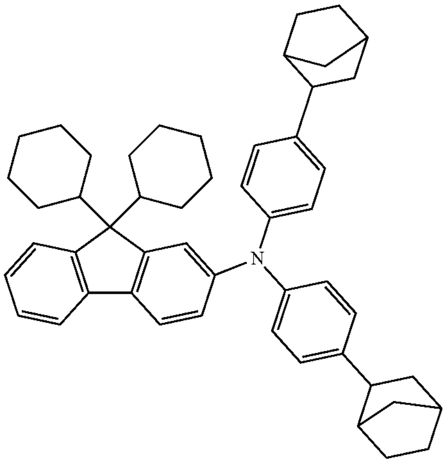
59
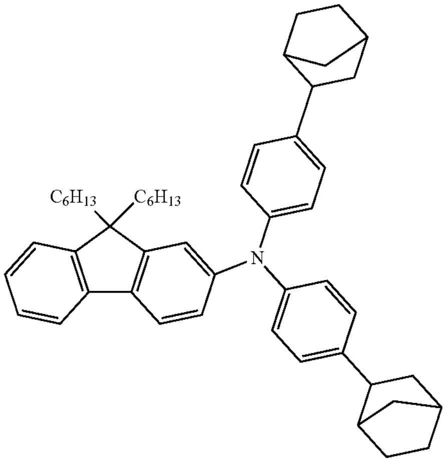
-continued
60
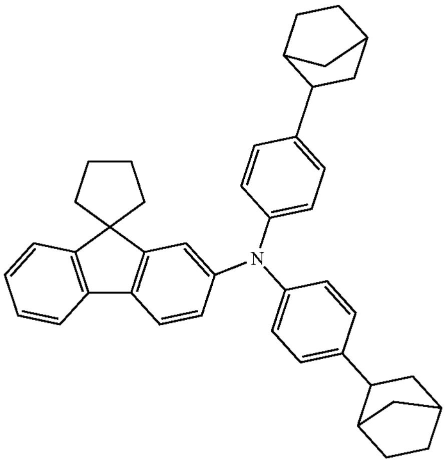
61
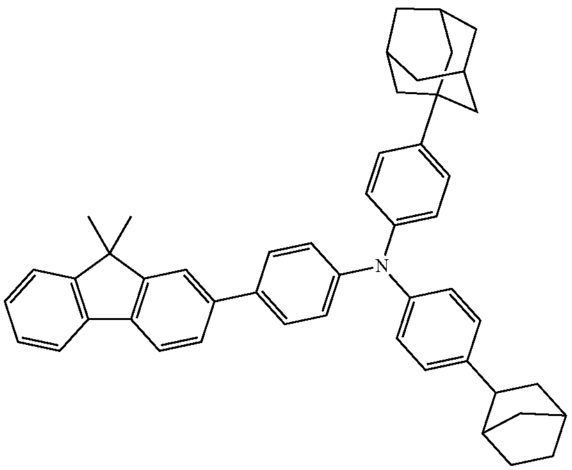
62
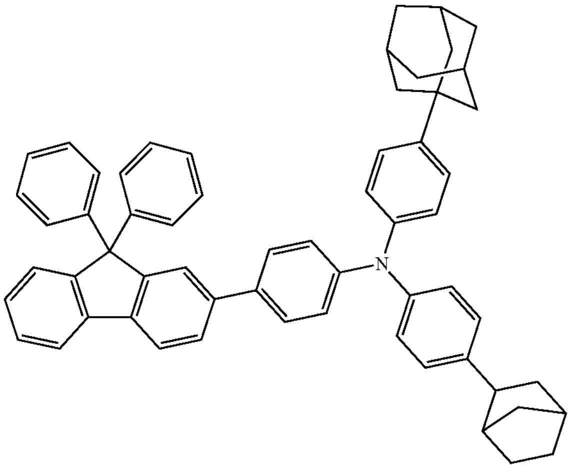

-continued
63
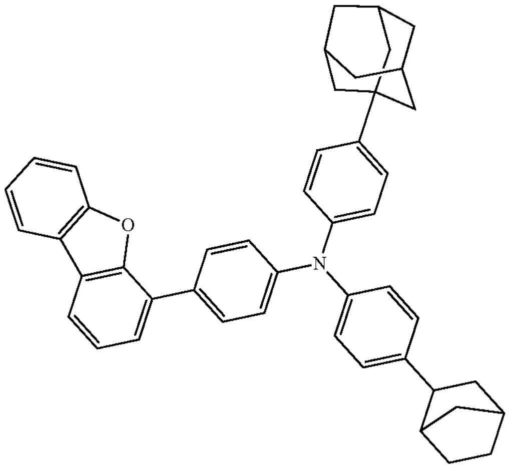
64
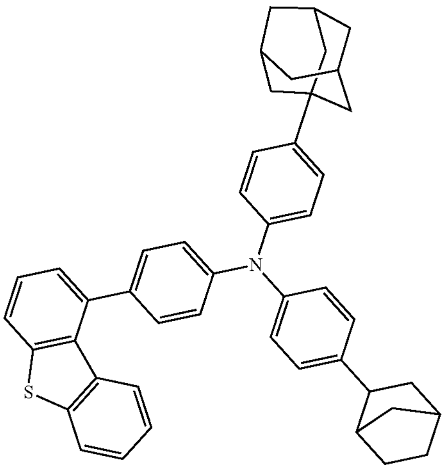
65
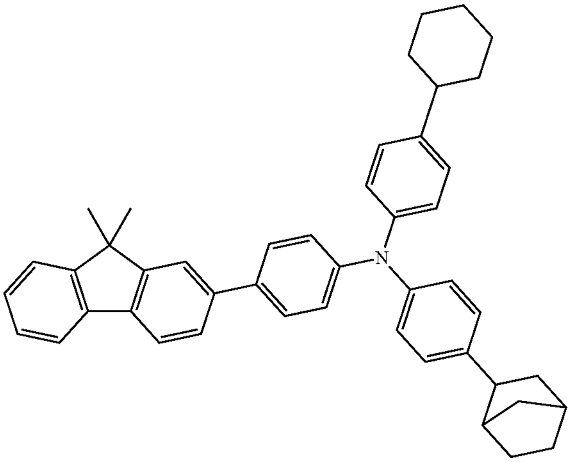
-continued
66
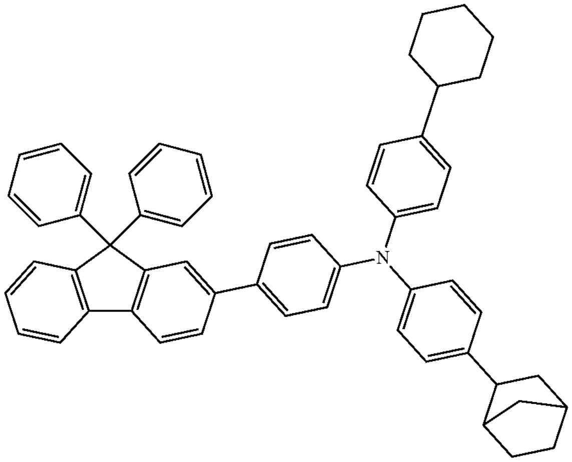
67
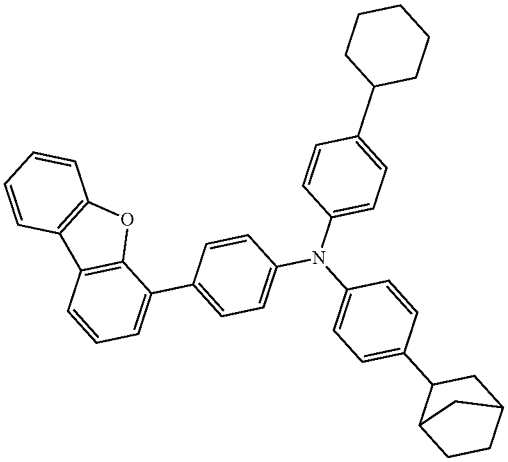
68
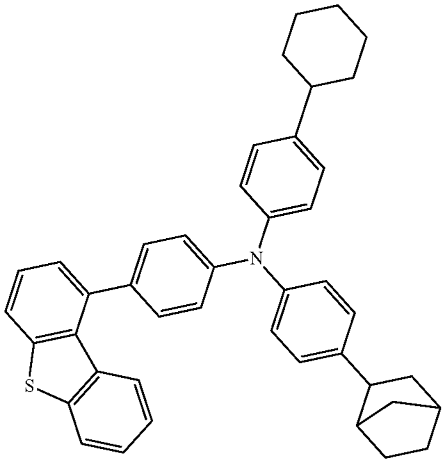

-continued

69

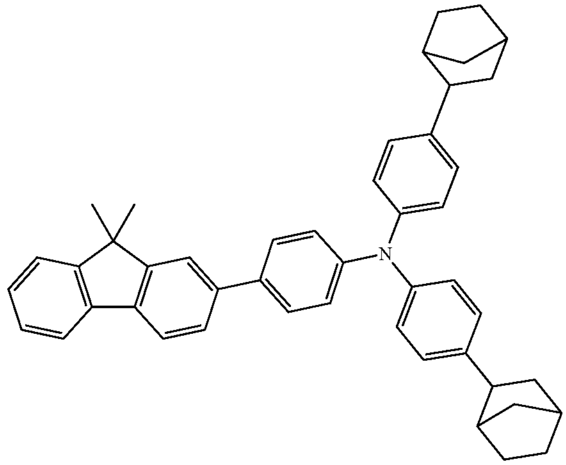

70

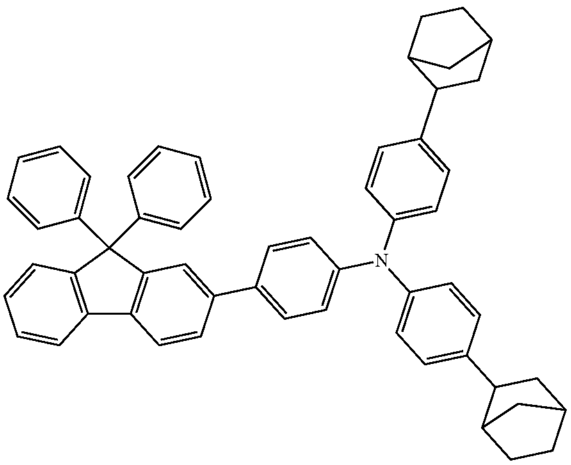

71

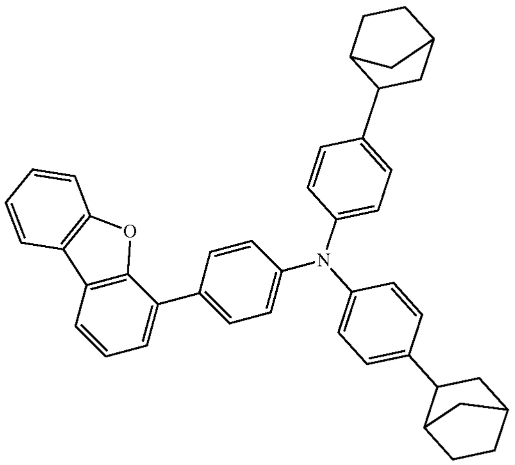

-continued

72

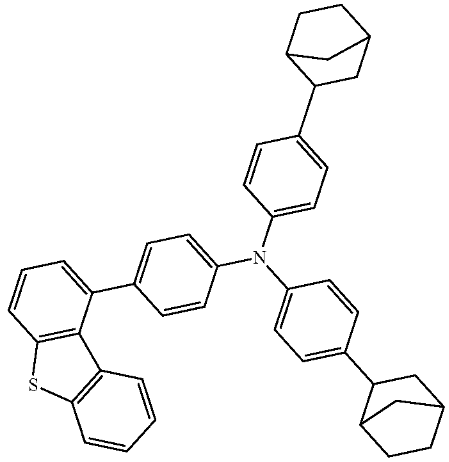

.

9. The light-emitting element of claim 1, wherein:

the at least one functional layer comprises: an emission layer; a first hole transport layer between the first electrode and the emission layer; a second hole transport layer between the first hole transport layer and the emission layer; and an electron transport region between the emission layer and the second electrode, and the first hole transport layer comprises the amine compound.

10. The light-emitting element of claim 9, wherein the second hole transport layer comprises an amine derivative compound represented by Formula 3:

Formula 3

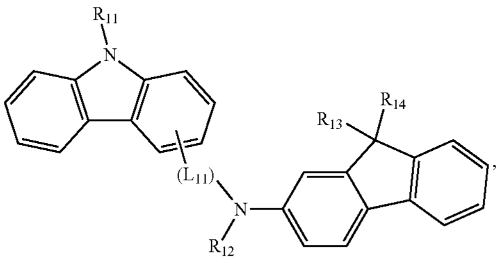

and wherein, in Formula 3, $L_{11}$ is a direct linkage, a substituted or unsubstituted arylene group having 6 to 30 ring-forming carbon atoms, or a substituted or unsubstituted heteroarylene group having 2 to 30 ring-forming carbon atoms, and $R_{11}$ to $R_{14}$ are each independently a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring.

11. The light-emitting element of claim 10, wherein the amine derivative compound represented by Formula 3 is represented by Formula 3-1 or Formula 3-2:

Formula 3-1

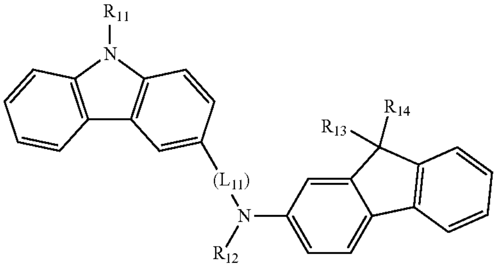

Formula 3-2

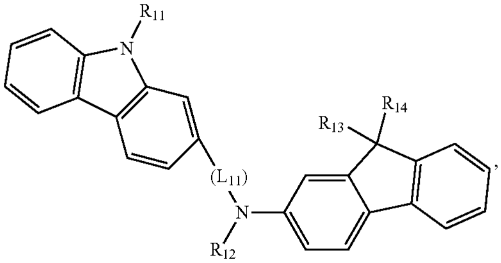

, and wherein, in Formula 3-1 and Formula 3-2, $L_{11}$, and $R_{11}$ to $R_{14}$ are each independently the same as defined in Formula 3.

12. The light-emitting element of claim 11, wherein the amine derivative compound represented by Formula 3-1 is represented by any one of compounds represented in Compound Group 2-1:

Compound Group 2-1

73

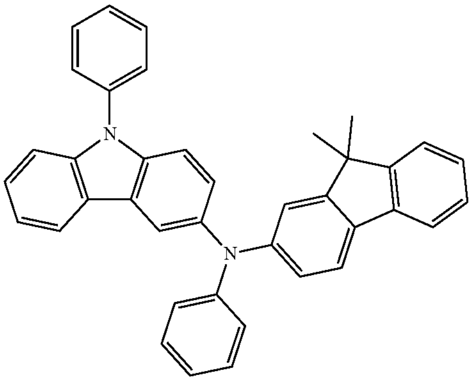

-continued

74

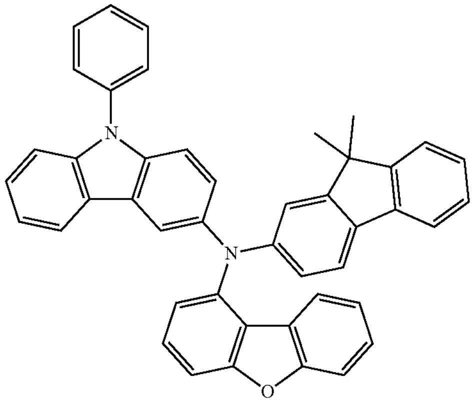

75

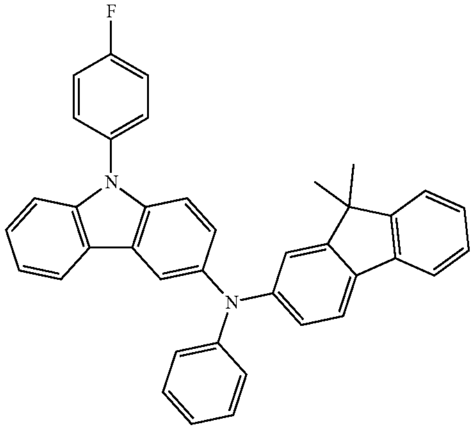

76

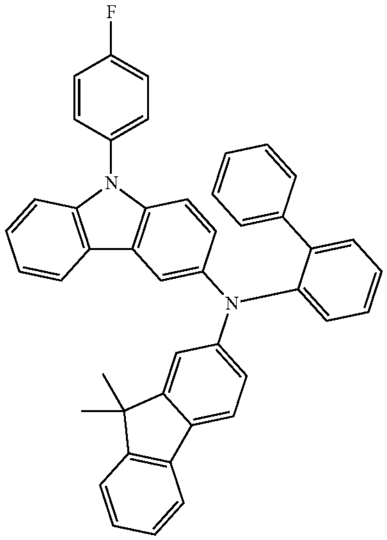

-continued
77
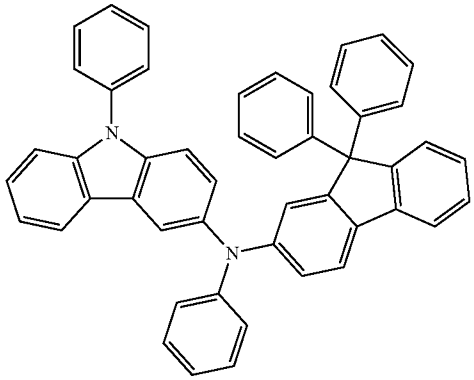
78
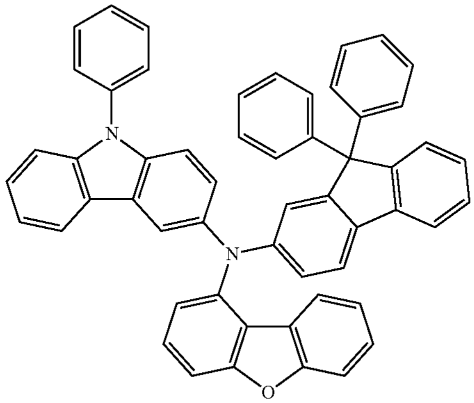
79
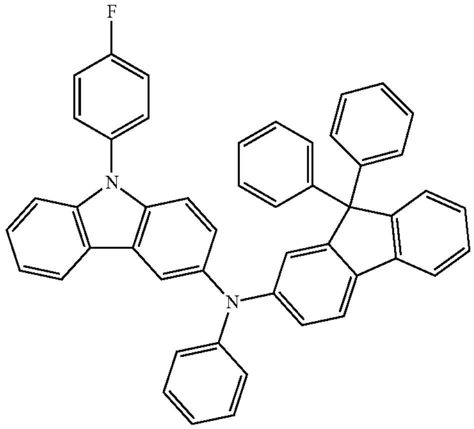
-continued
80
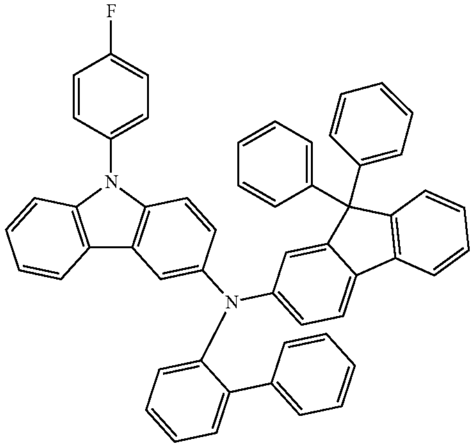
81
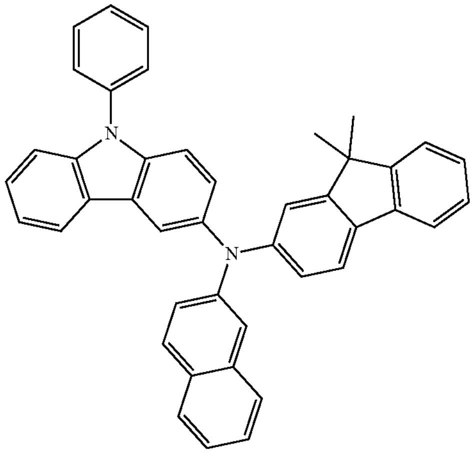
82
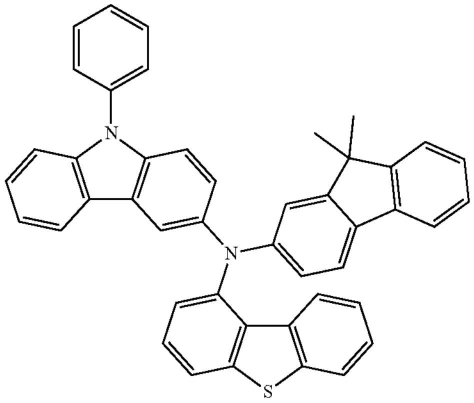

-continued
83
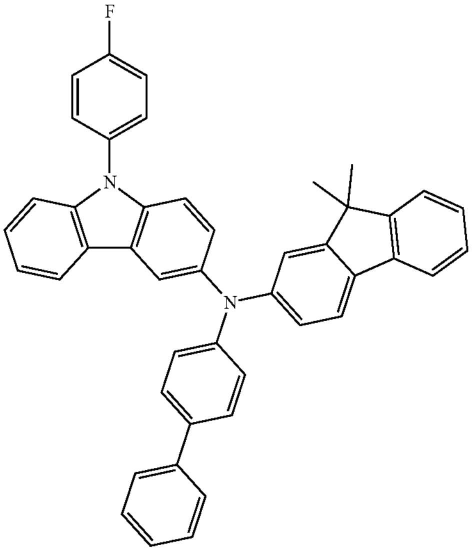
84
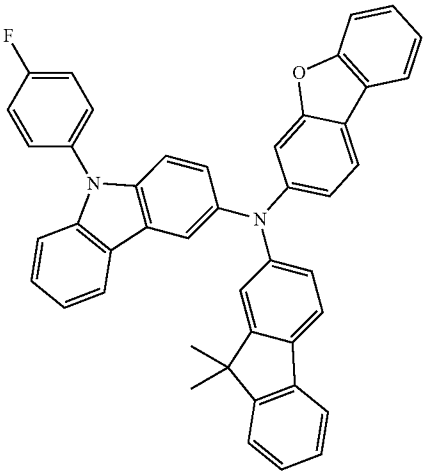
85
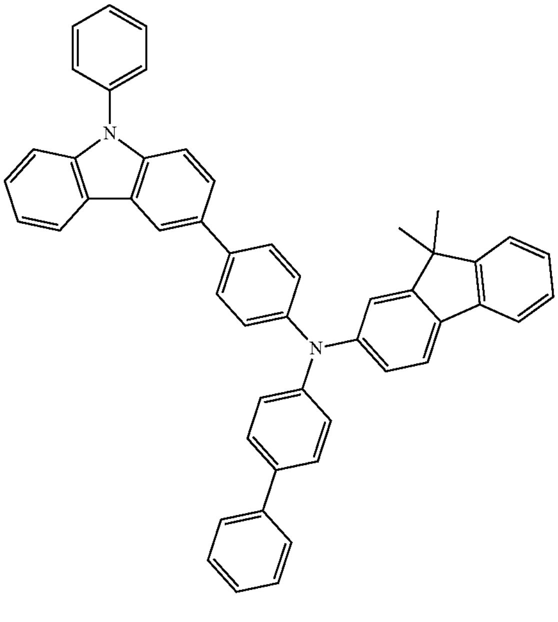
-continued
86
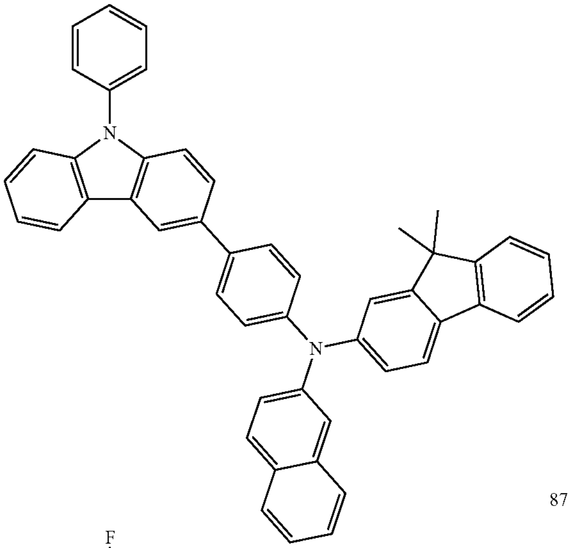
87
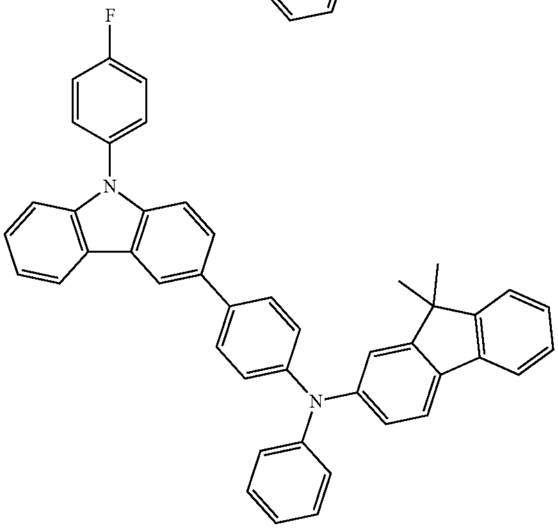
88
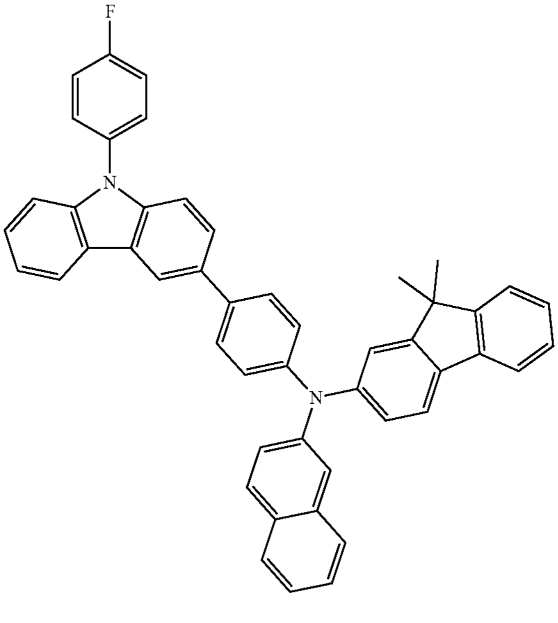

89
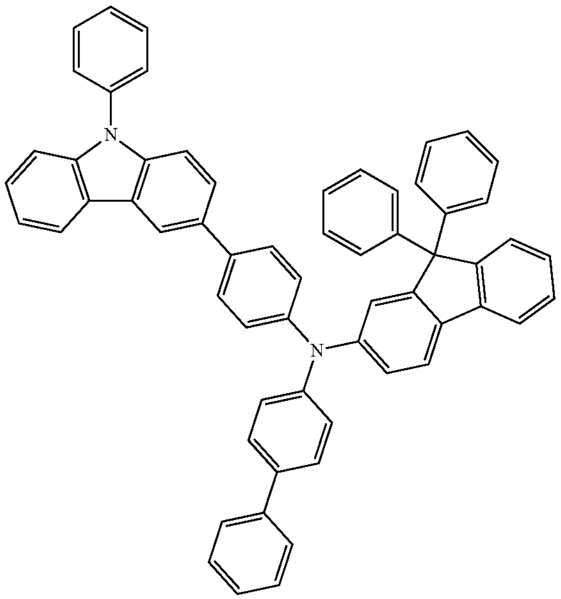
90
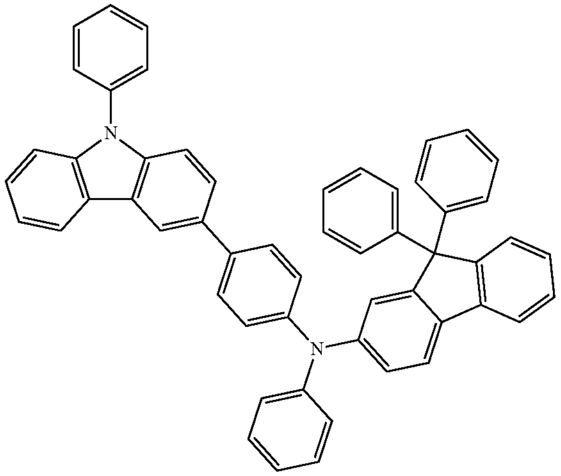
91
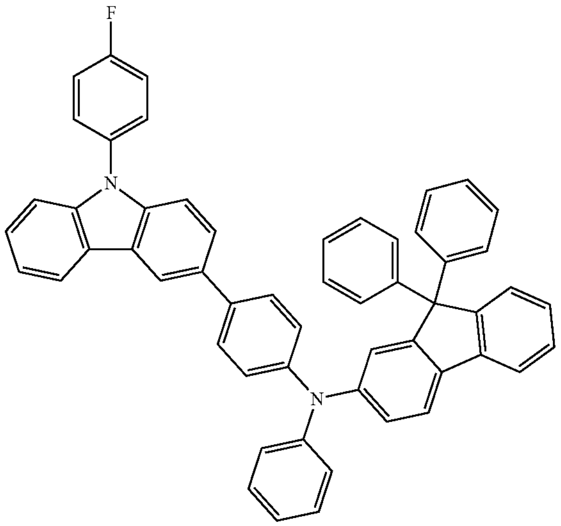
92
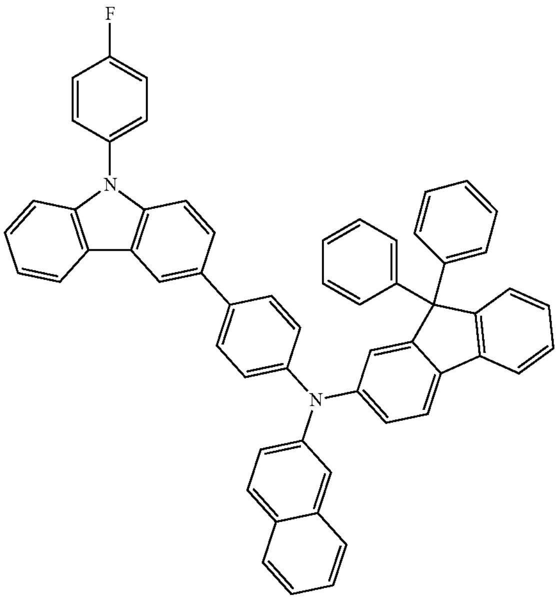
.
13. The light-emitting element of claim 11, wherein the amine derivative compound represented by Formula 3-2 is represented by any one of compounds represented in Compound Group 2-2:
Compound Group 2-2
93
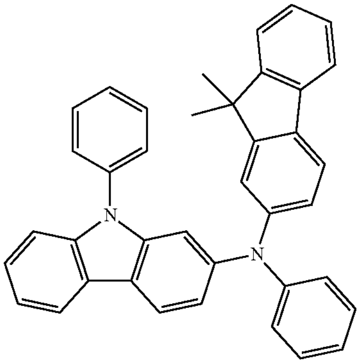
94
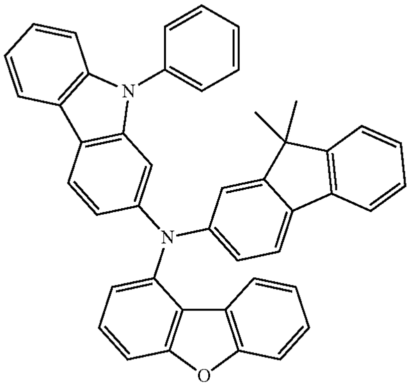

-continued
95
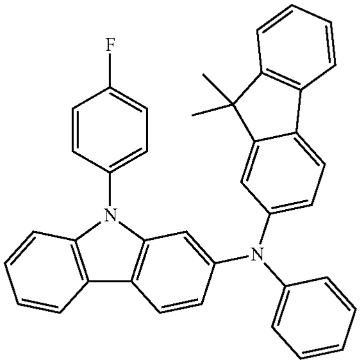
96
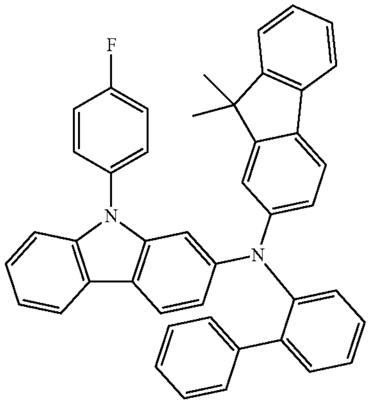
97
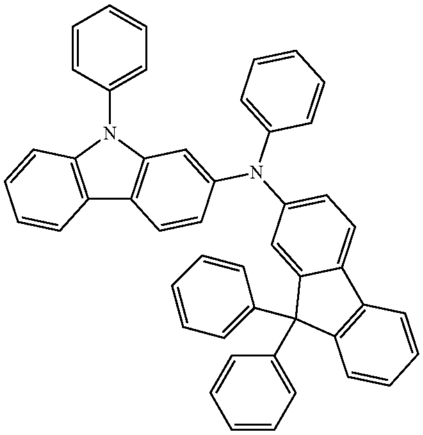
98
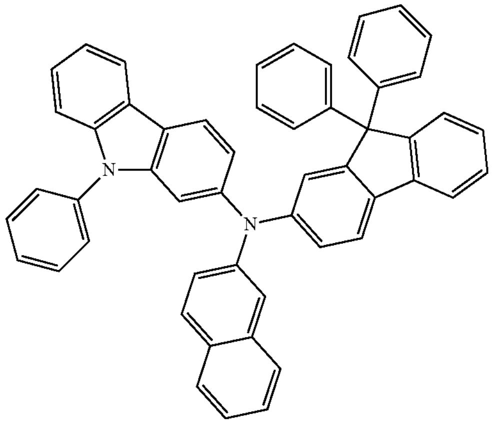
-continued
99
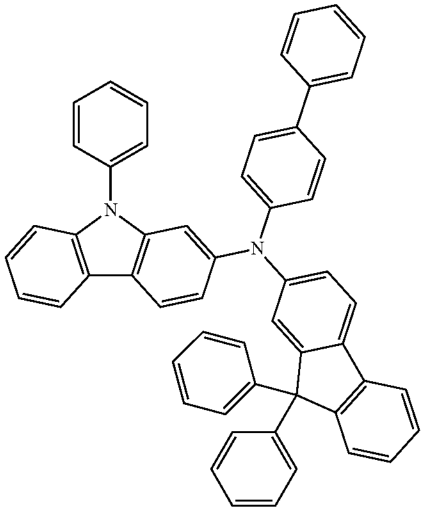
100
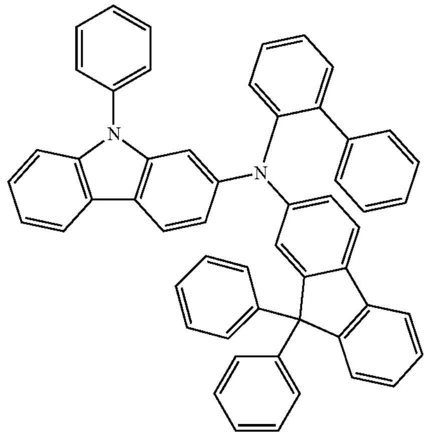
101
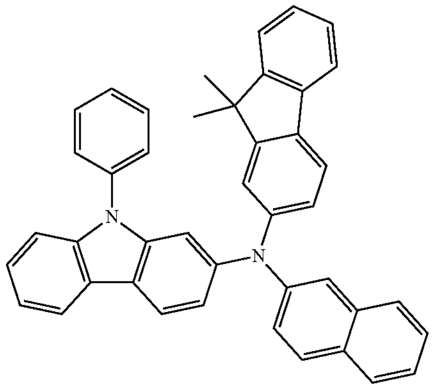

-continued
102
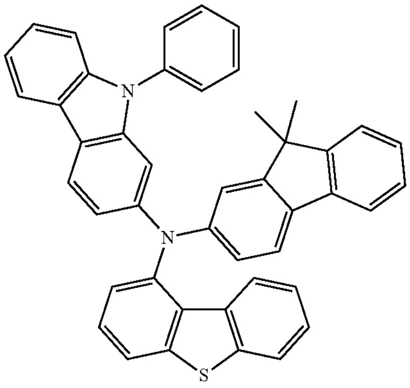
103
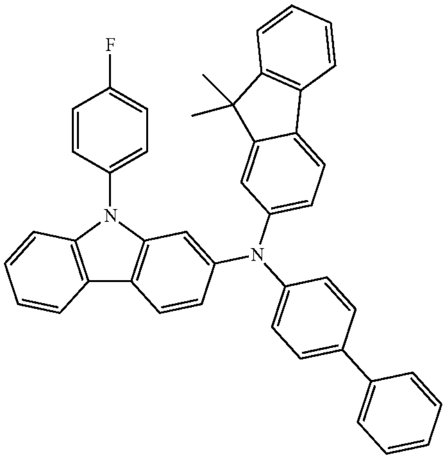
104
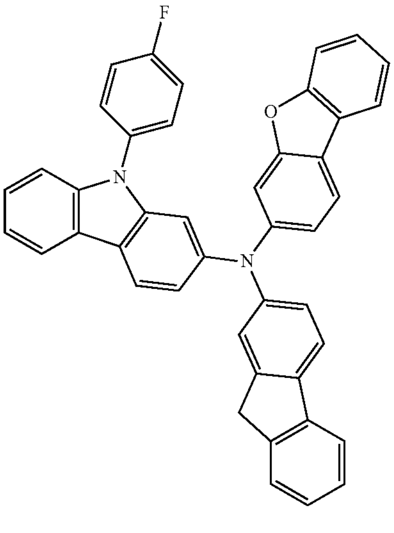
-continued
105
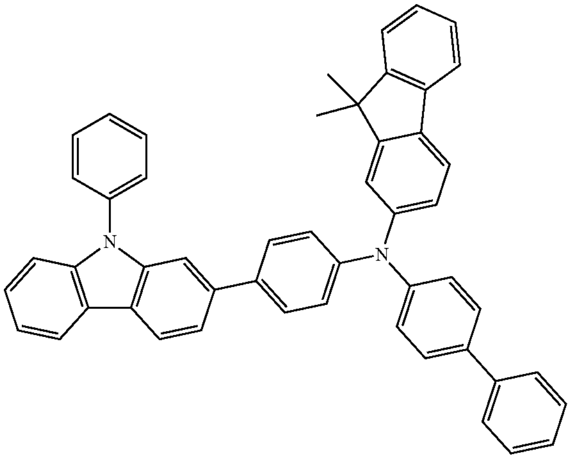
106
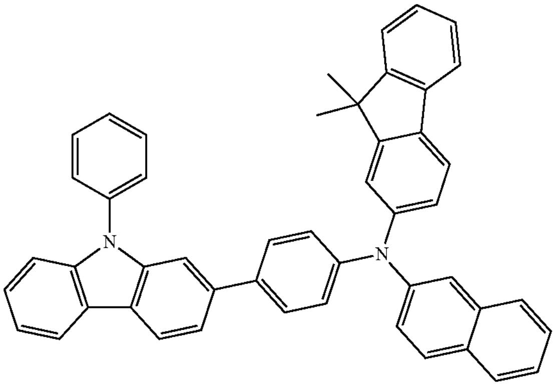
107
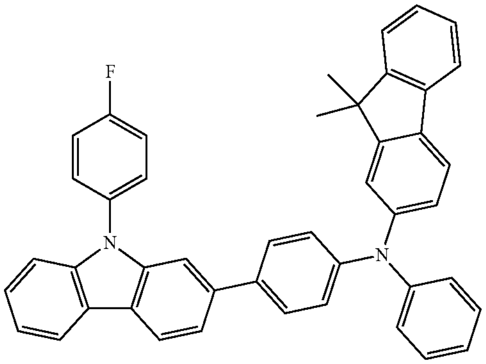

-continued

108

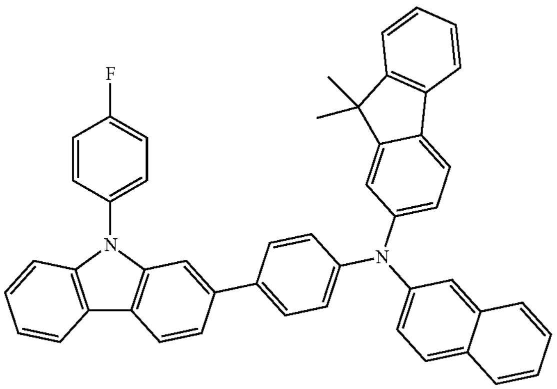

109

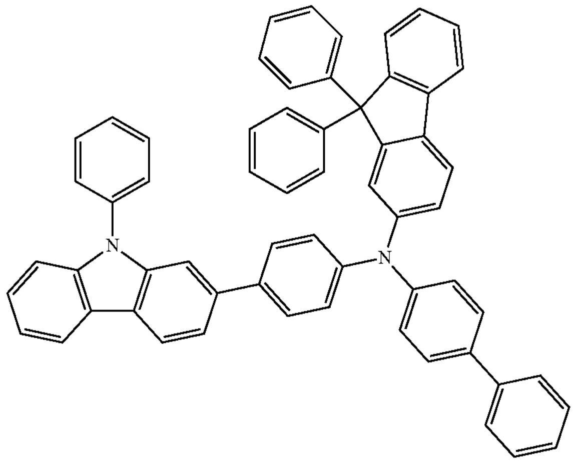

110

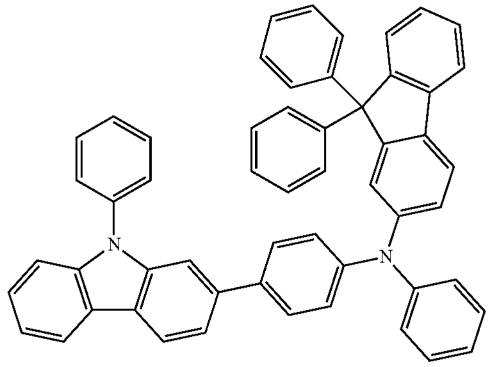

111

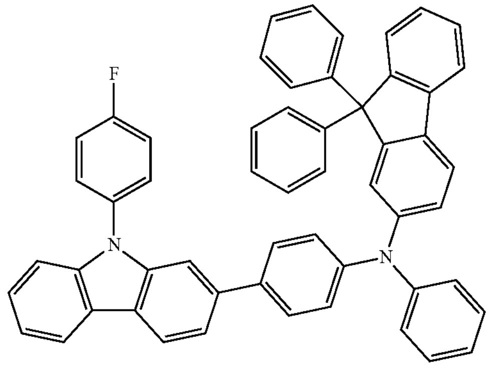

-continued

112

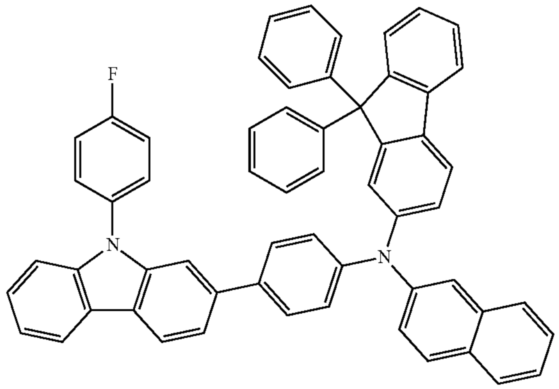

.

14. An amine compound represented by Formula 1:

Formula 1

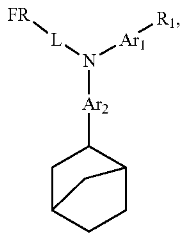

wherein, in Formula 1, $R_1$ is an adamantyl group, a cyclohexyl group, or a bicycloheptyl group, $Ar_1$ and $Ar_2$ are each independently a substituted or unsubstituted arylene group having 6 to 30 ring-forming carbon atoms, L is a direct linkage, a substituted or unsubstituted arylene group having 6 to 30 ring-forming carbon atoms, or a substituted or unsubstituted heteroarylene group having 2 to 30 ring-forming carbon atoms, and FR is represented by Formula 2:

Formula 2

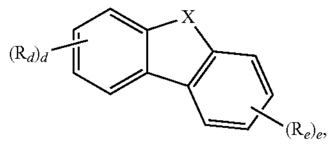

wherein, in Formula 2,

X is $CR_aR_b$, N, $NR_c$, O, or S, $R_a$ to $R_c$ are each independently a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring, d and e are each independently an integer of 0 to 4, and $R_d$ and $R_e$ are each independently a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or bonded to an adjacent group to form a ring, and wherein when $R_1$ is a bicycloheptyl group, then at least one of $Ar_1$ or $Ar_2$ is a substituted or unsubstituted phenylene group.

15. The amine compound of claim 14, wherein the amine compound represented by Formula 1 is represented by Formula 1-1 or Formula 1-2:

Formula 1-1

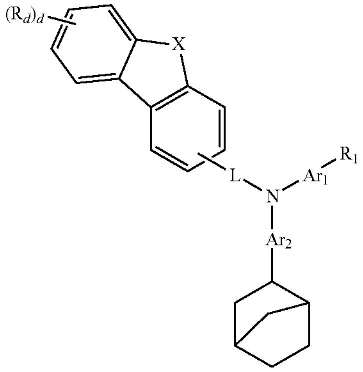

Formula 1-2

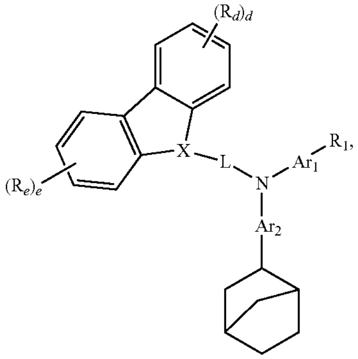

and wherein, in Formula 1-1 and Formula 1-2, $R_1$, L, $Ar_1$, and $Ar_2$ are each independently the same as defined in Formula 1, and X, $R_d$, $R_e$, d, and e are each independently the same as defined in Formula 2.

16. The amine compound of claim 15, wherein the amine compound represented by Formula 1-2 is represented by Formula 1-2A:

Formula 1-2A

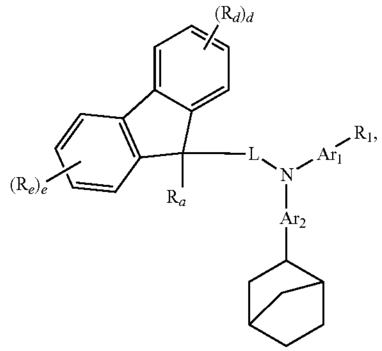

and wherein, in Formula 1-2A, $R_1$, L, $Ar_1$, and $Ar_2$ are each independently the same as defined in Formula 1, and $R_a$, $R_d$, $R_e$, d, and e are each independently the same as defined in Formula 2.

17. The amine compound of claim 14, wherein in Formula 1, $Ar_1$ and $Ar_2$ are a substituted or unsubstituted phenylene group.

18. The amine compound of claim 14, wherein the amine compound represented by Formula 1 is represented by Formula 1A:

Formula 1A

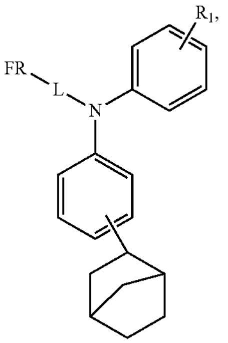

and wherein in Formula 1A, $R_1$, L, and FR are each independently the same as defined in Formula 1.

19. The amine compound of claim 18, wherein the amine compound represented by Formula 1A is represented by Formula 1A-1:

Formula 1A-1
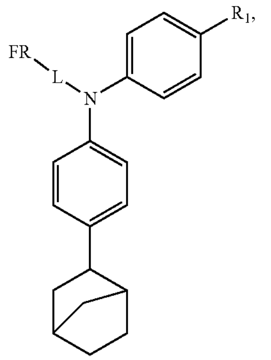
and
wherein in Formula 1A-1, $R_1$, L, and FR are each independently the same as defined in Formula 1.
20. An amine compound represented by any one of compounds in Compound Group 1:
Compound Group 1
1
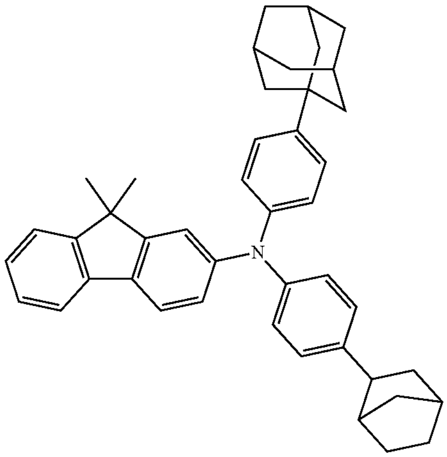
2
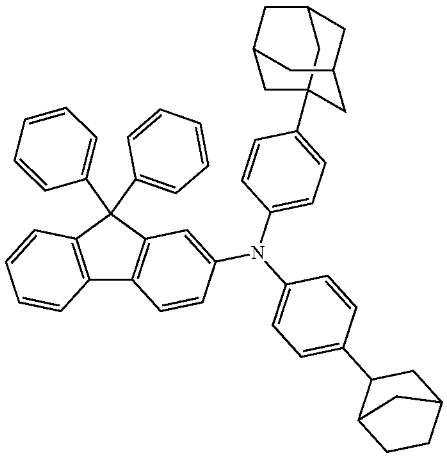
-continued
3
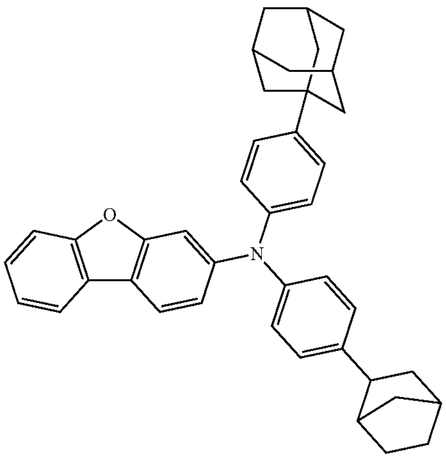
4
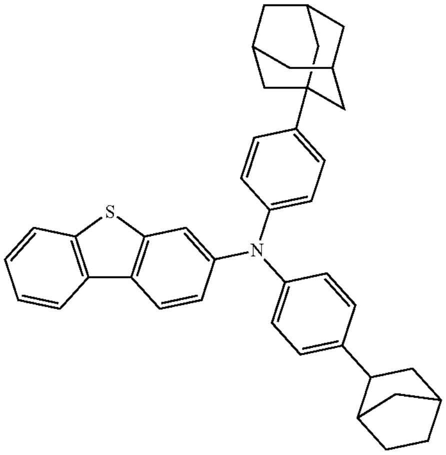
5
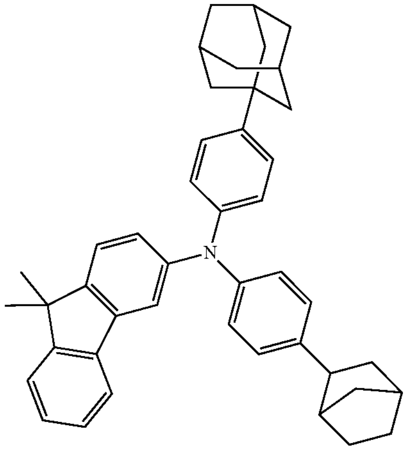

-continued
6
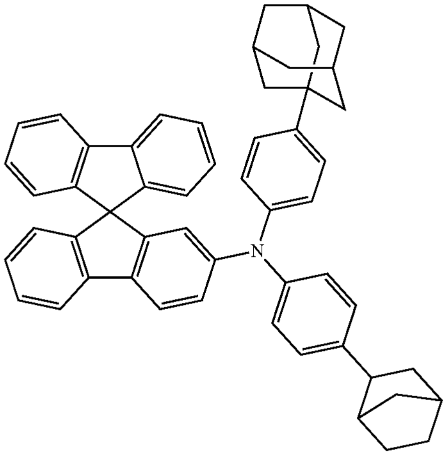
7
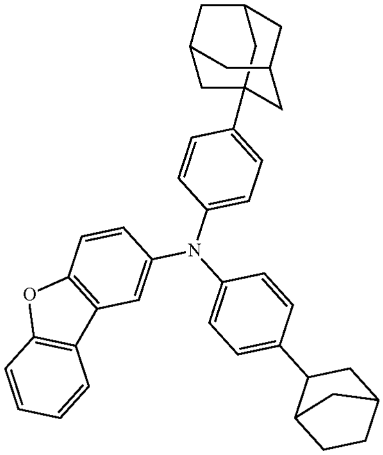
8
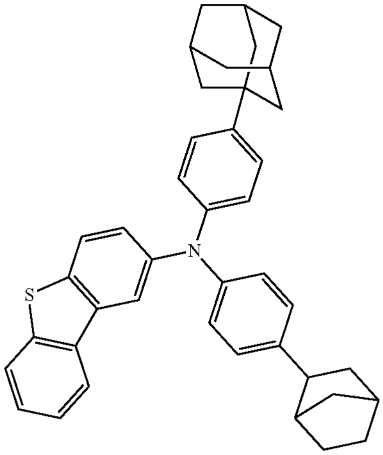
-continued
9
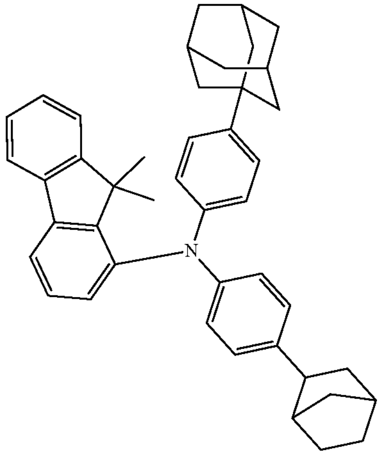
10
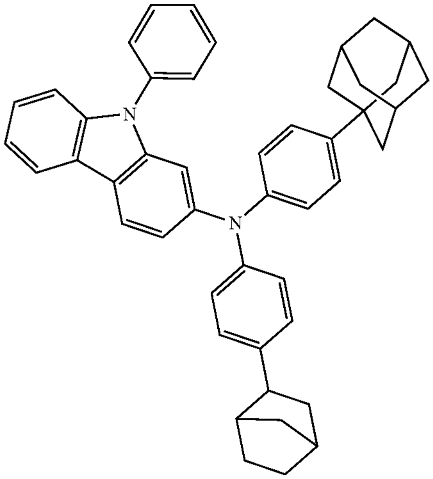
11
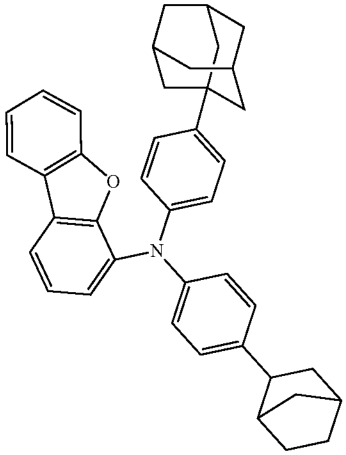

-continued
12
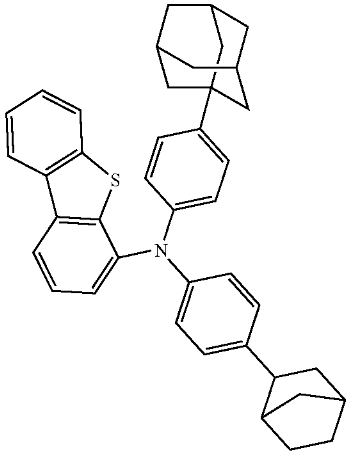
13
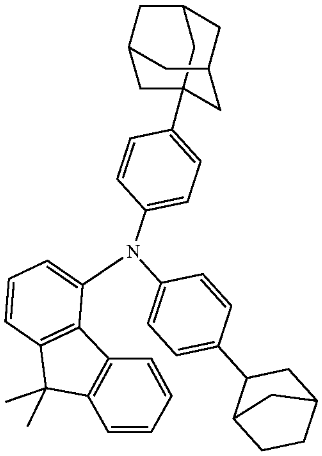
14
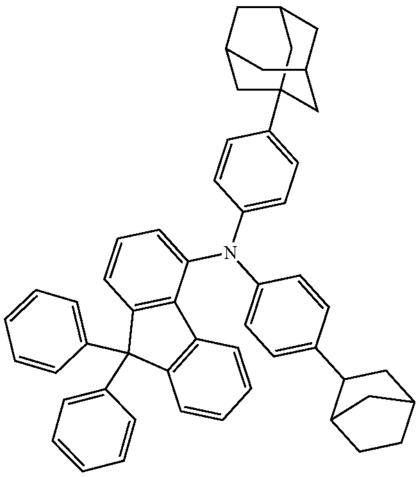
-continued
15
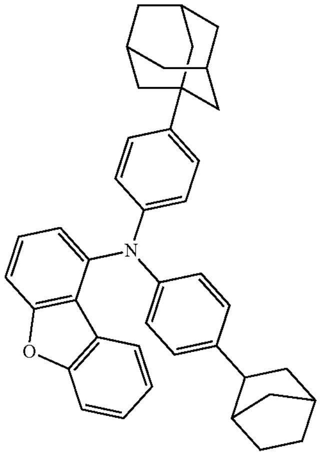
16
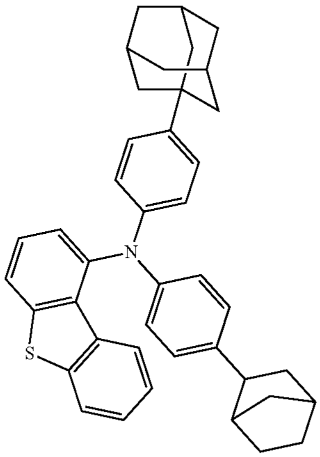
17
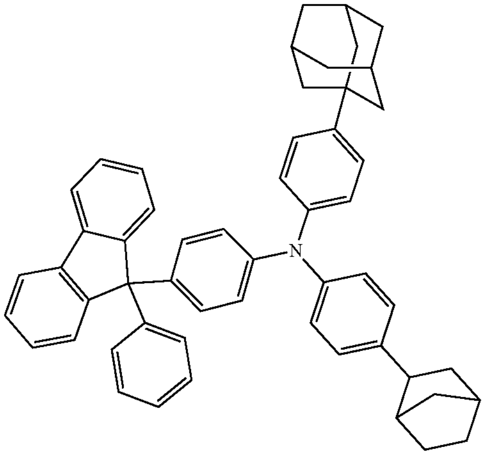

-continued
18
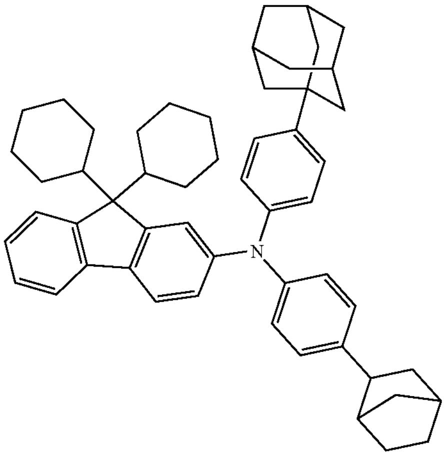
19
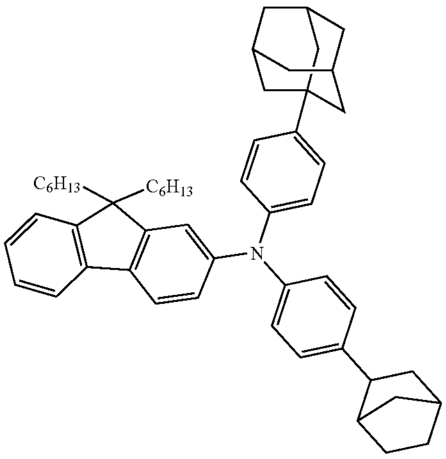
20
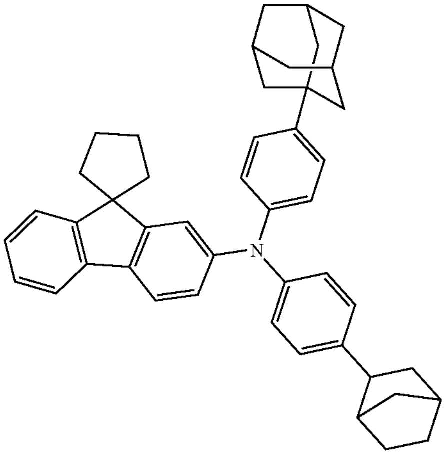
-continued
21
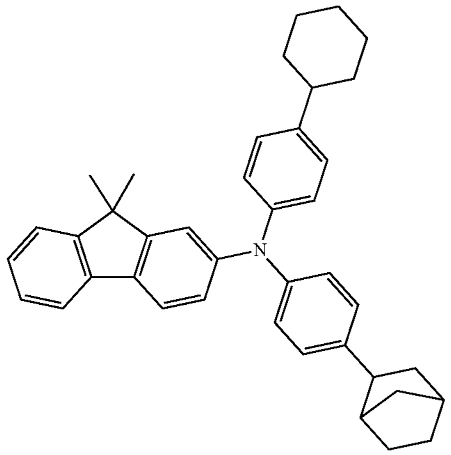
22
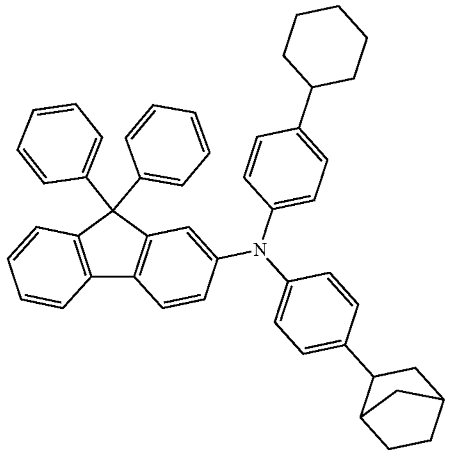
23
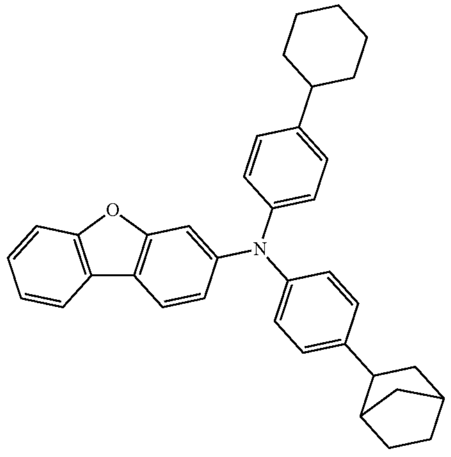

-continued
24
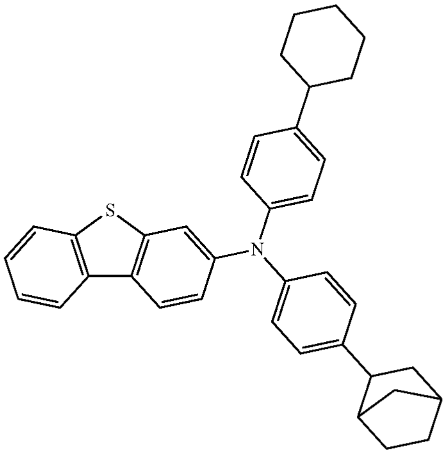
25
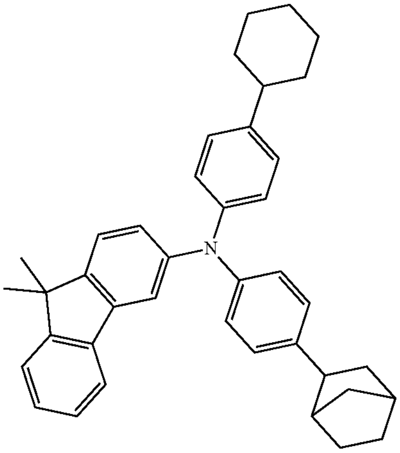
26
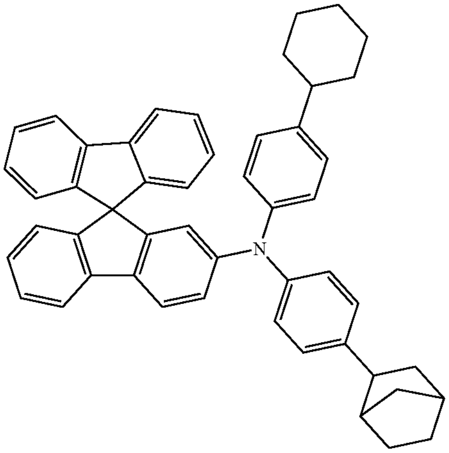
-continued
27
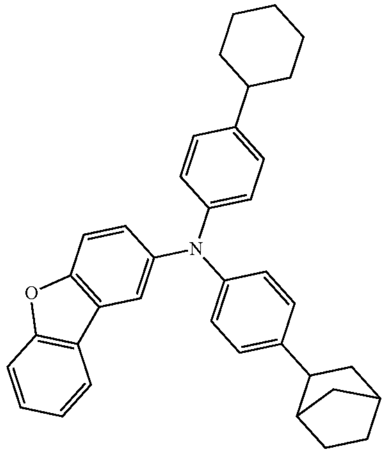
28
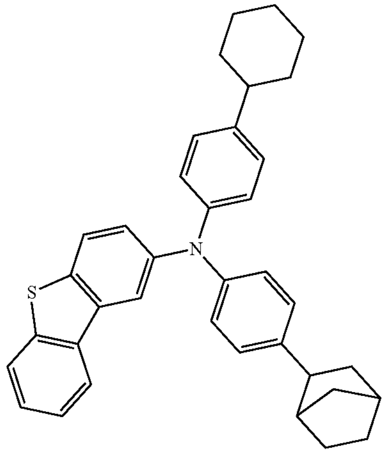
29
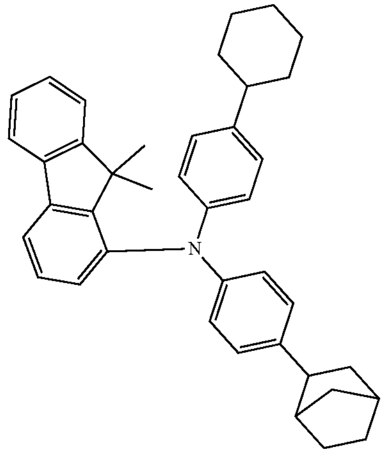

-continued
30
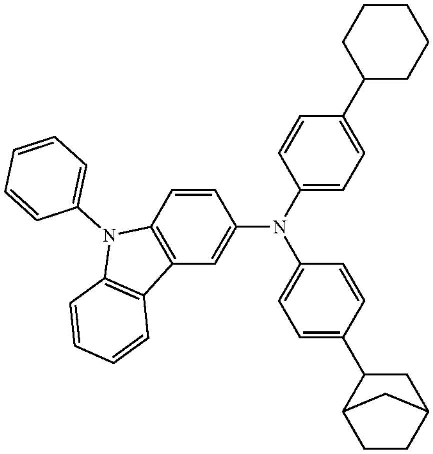
31
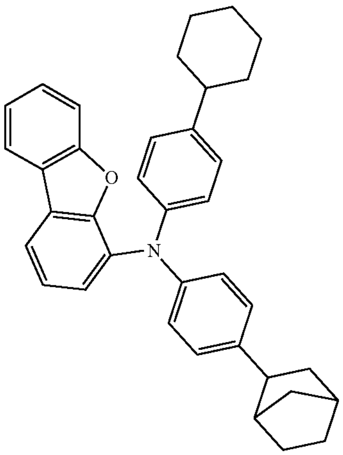
32
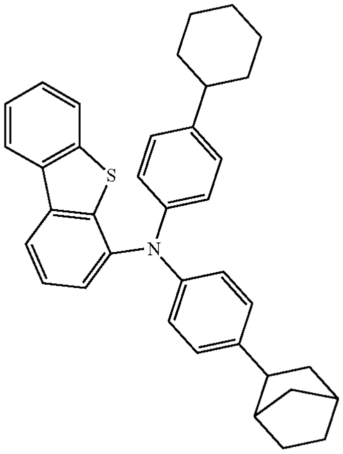
-continued
33
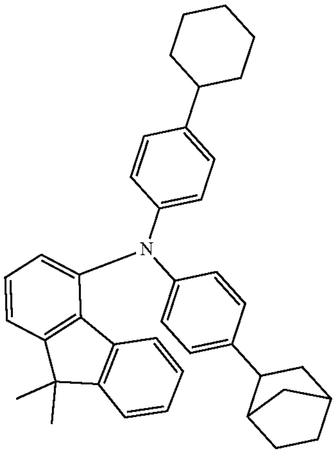
34
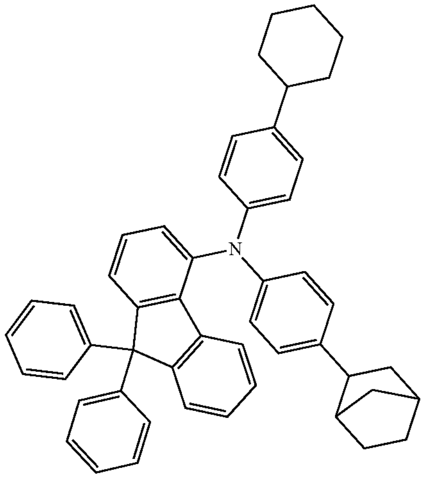
35
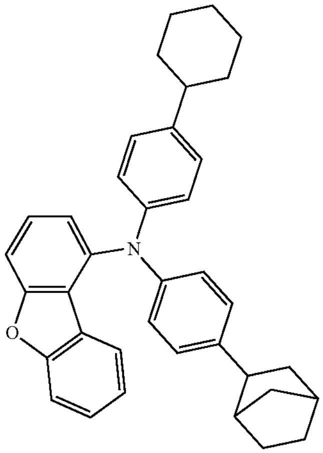

-continued
36
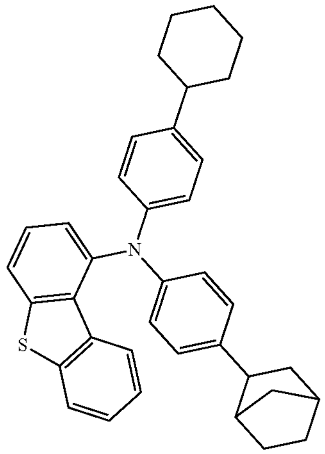
37
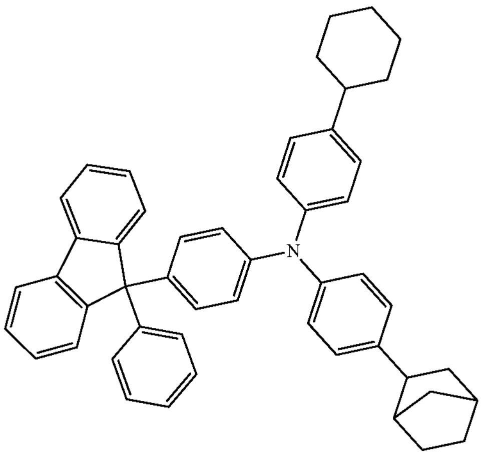
38
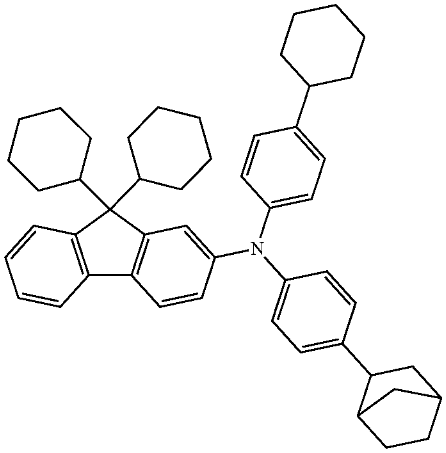
-continued
39
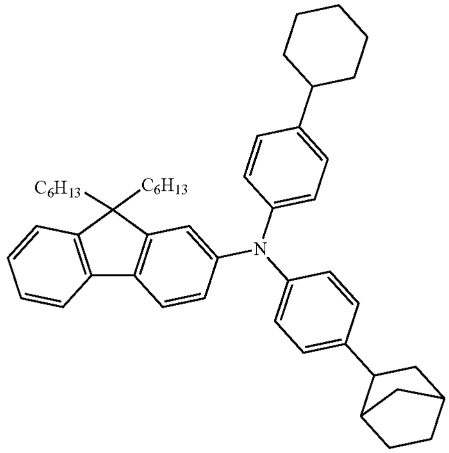
40
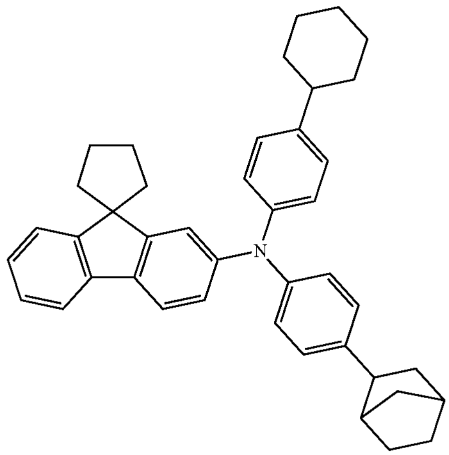
41
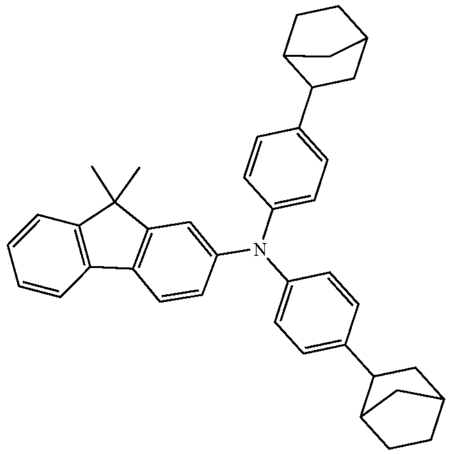

-continued
42
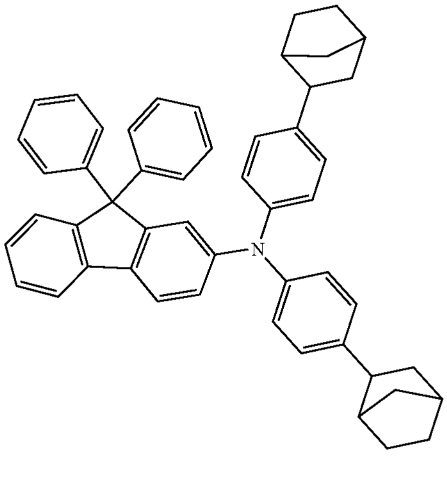
43
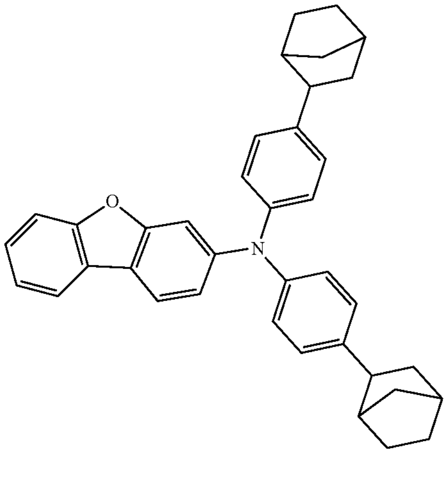
44
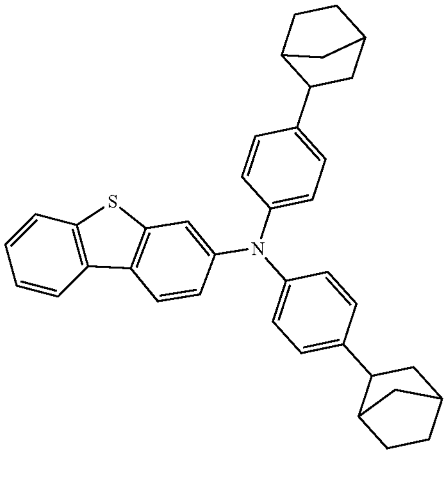
-continued
45
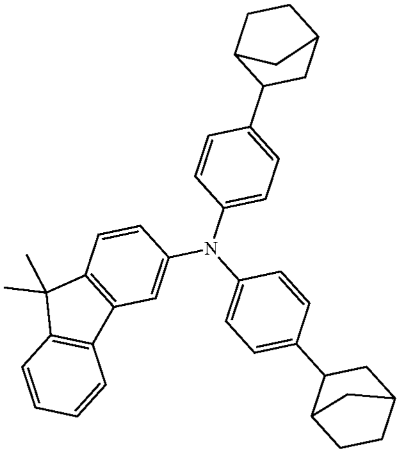
46
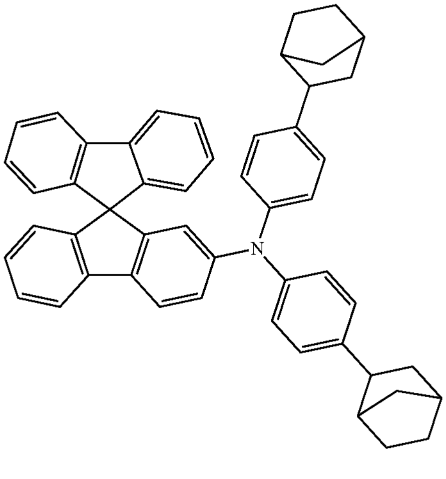
47
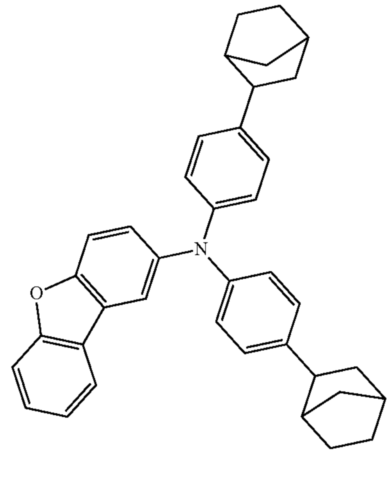

48
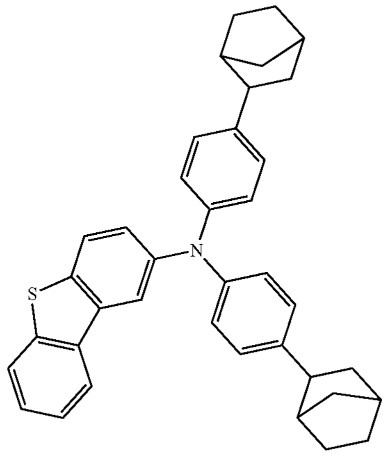
49
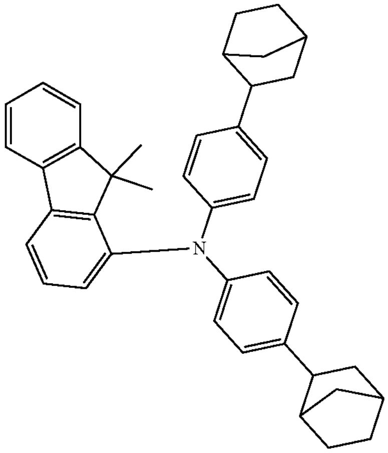
50
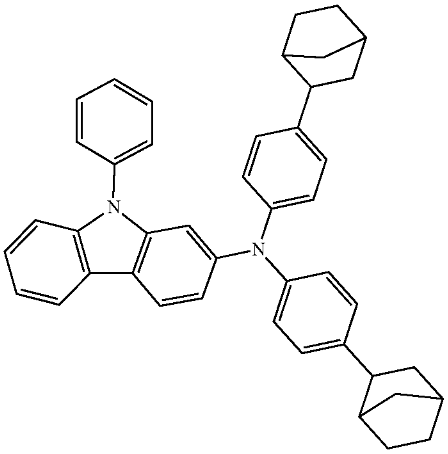
51
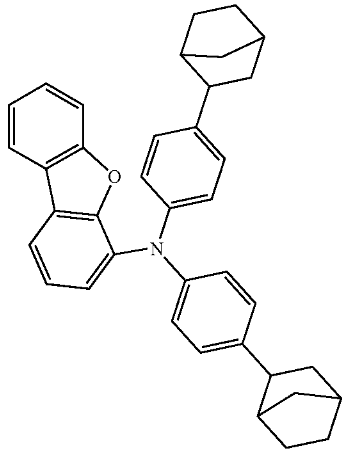
52
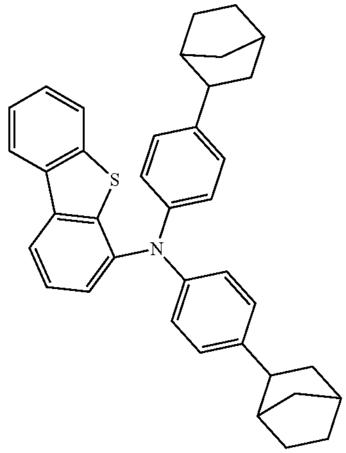
53
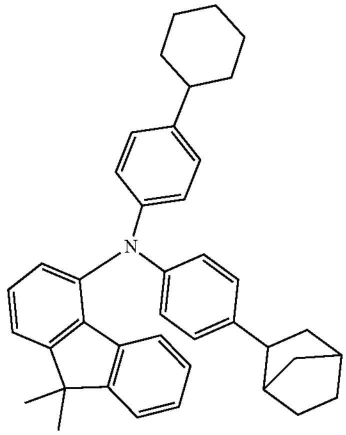

-continued
54
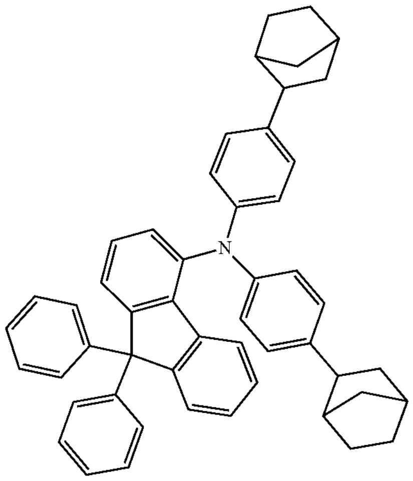
55
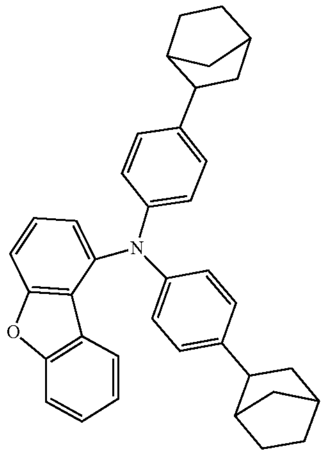
56
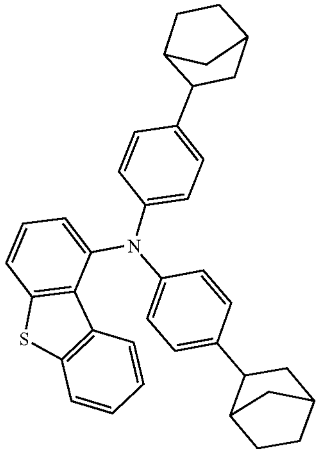
-continued
57
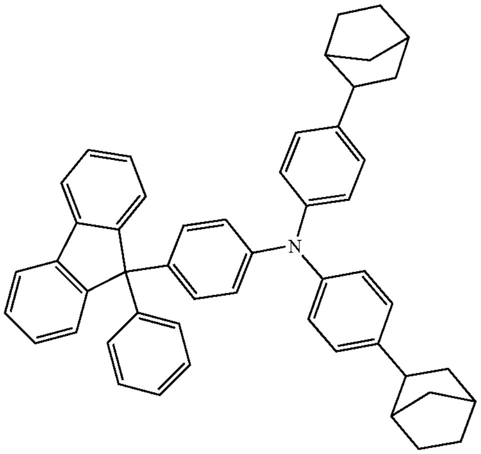
58
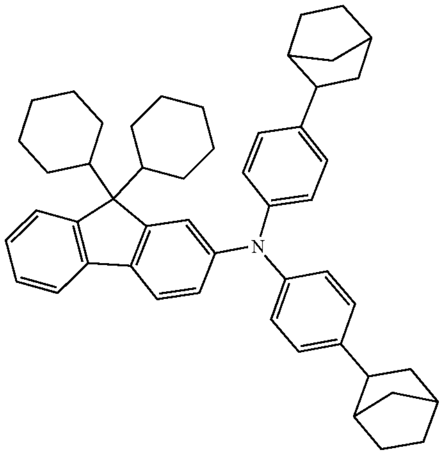
59
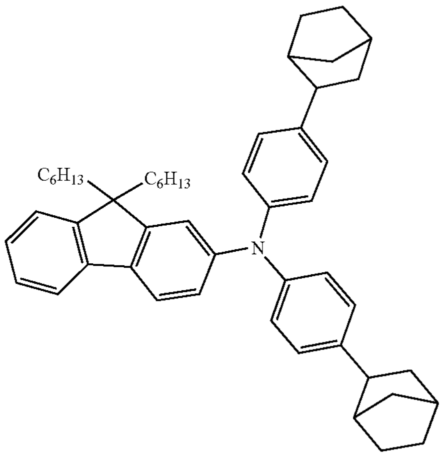

-continued
60
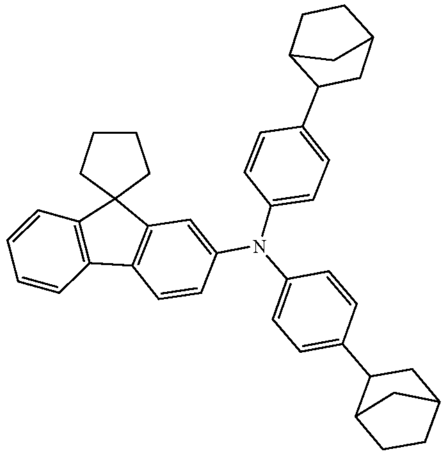
61
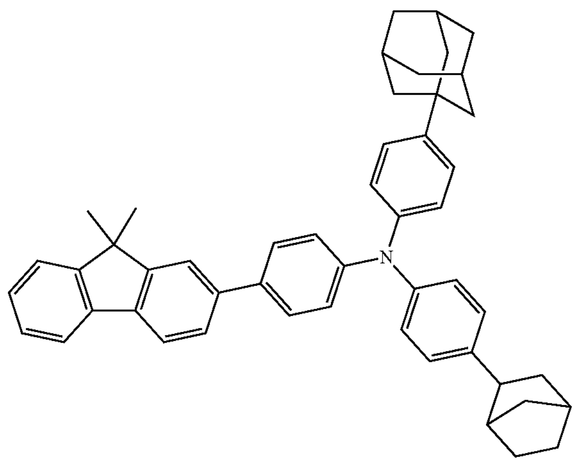
62
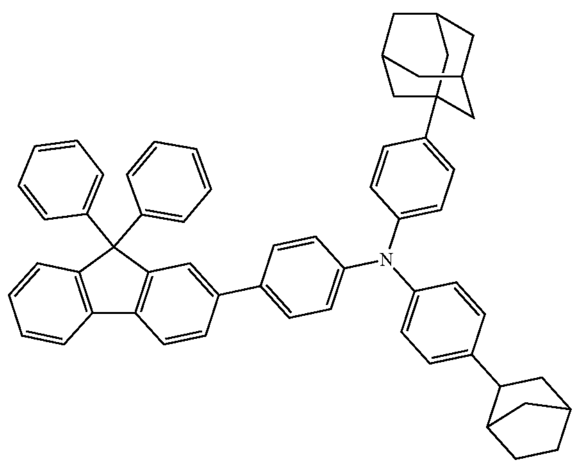
-continued
63
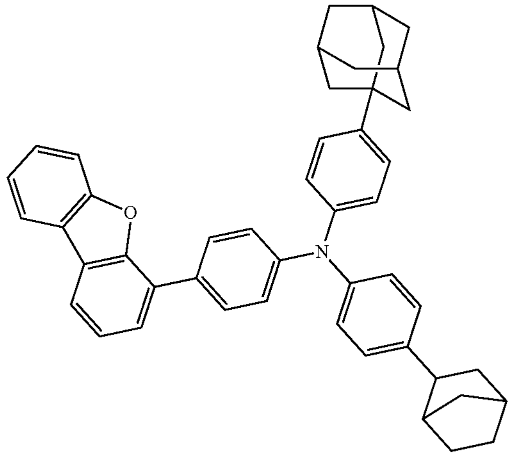
64
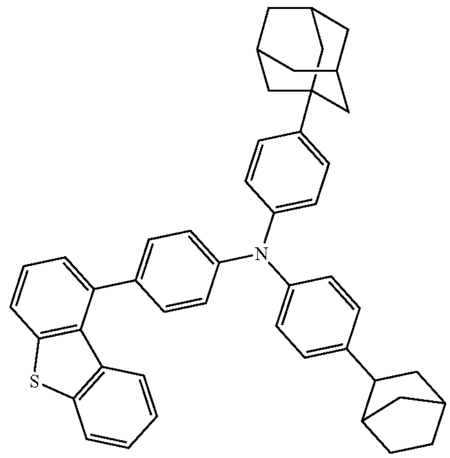
65
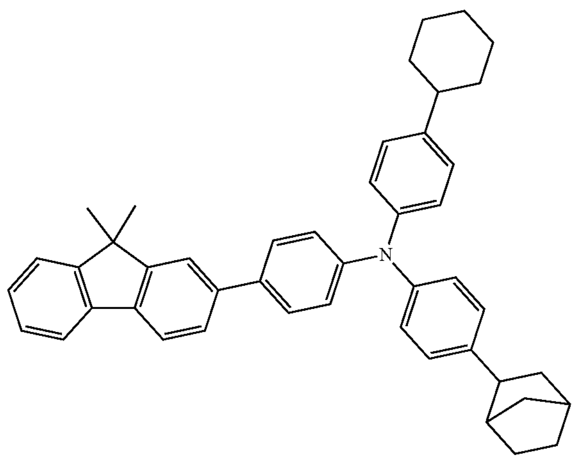

-continued
66
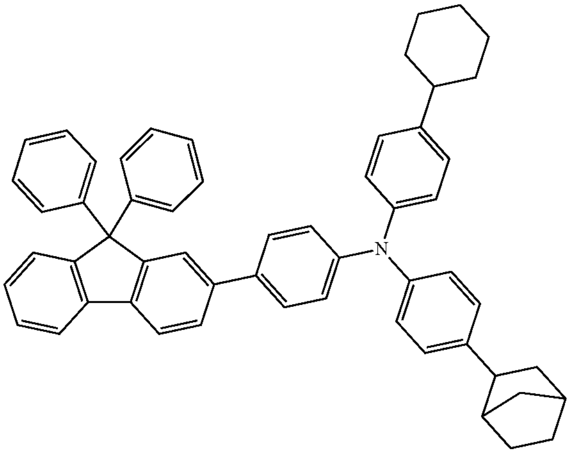
67
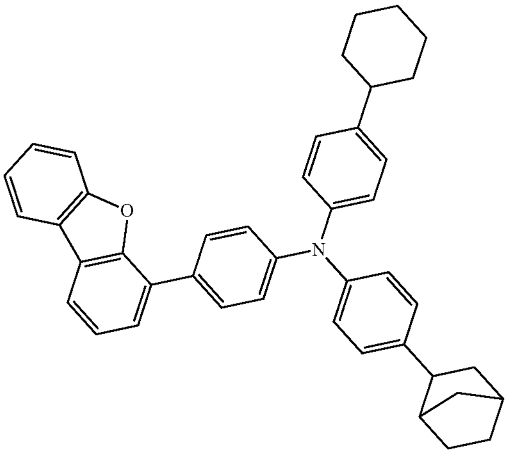
68
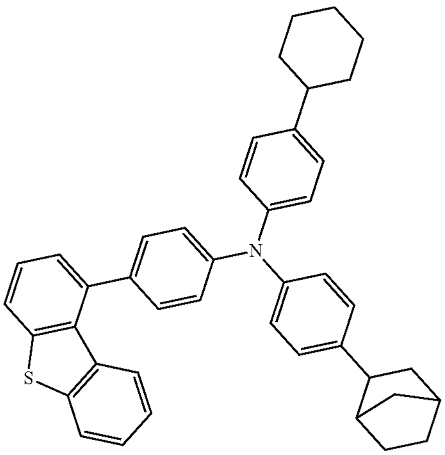
-continued
69
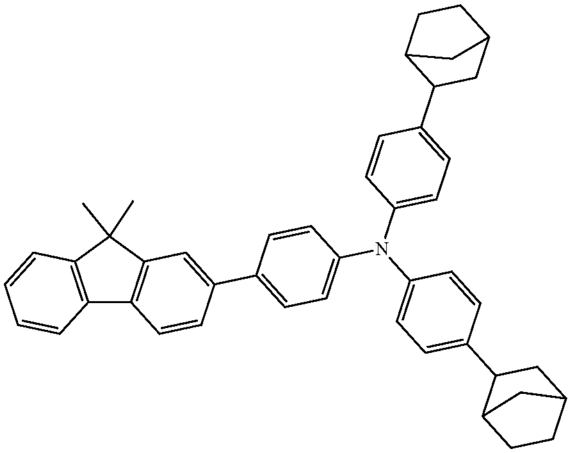
70
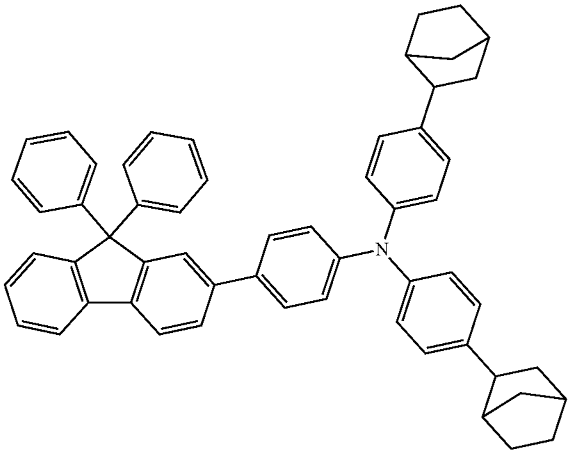
71
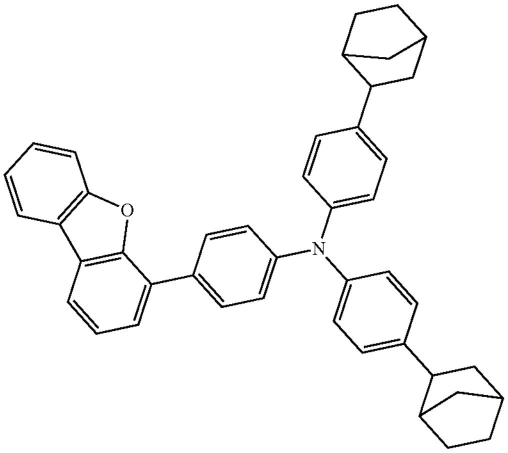

-continued
72
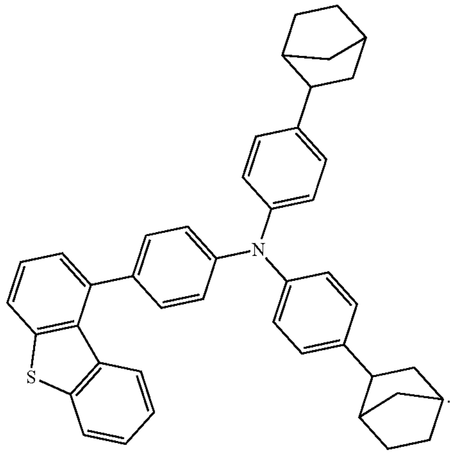
* * * * *